(12) United States Patent
Sas et al.

(10) Patent No.: US 7,534,871 B2
(45) Date of Patent: May 19, 2009

(54) PREPARATION AND USE OF CARBOHYDRATE-BASED BICYCLIC RING STRUCTURES WITH ANTIMICROBIAL AND CYTOSTATIC ACTIVITY

(75) Inventors: Benedikt Sas, Ghent (BE); Johan van der Eycken, Ninove (BE); Johan Van hemel, Antwerp (BE); Petra Blom, Sint-Amandsberg (BE); Jan Vandenkerckhove, Scherpenheuvel-Zichem (BE); Bart Ruttens, Ghent (BE)

(73) Assignee: Kemin Pharma B.V.B.A., Des Moines, IA (US)

( * ) Notice: Subject to any disclaimer, the term of this patent is extended or adjusted under 35 U.S.C. 154(b) by 402 days.

(21) Appl. No.: 10/861,768

(22) Filed: Jun. 4, 2004

(65) Prior Publication Data

US 2004/0224904 A1  Nov. 11, 2004

(51) Int. Cl.
*C07H 1/00* (2006.01)
*C07H 17/02* (2006.01)
(52) U.S. Cl. ............... 536/17.5; 536/1.11; 536/4.1; 536/17.2
(58) Field of Classification Search ............... 536/4.1, 536/6, 1.11, 17.2, 17.5
See application file for complete search history.

(56) References Cited

FOREIGN PATENT DOCUMENTS

WO      WO 03027148 A1 *  4/2003

OTHER PUBLICATIONS

Boyer et al. Ready Protease-Catalyzed Synthesis of Carbohydrate-Amino Acid Conjugates. Sep. 12, 2001. Chem Commun., 2001, pp. 1908-1909.*

* cited by examiner

*Primary Examiner*—Elli Peselev
(74) *Attorney, Agent, or Firm*—Kent A. Herink; Emily E. Harris

(57) ABSTRACT

Novel carbohydrate-based compounds with an attached ring system that have antimicrobial or cytostatic activity. The compounds are administered to humans and animals for the treatment or amelioration of bacterial, fungal, viral or protozoal infections or tumors. The compounds are of the general formula:

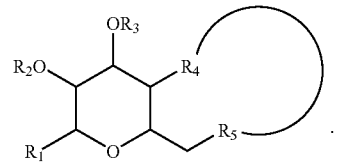

4 Claims, 14 Drawing Sheets a) pyridine, DMAP, CH$_2$Cl$_2$, r.t., 18 h; b) Grubb's cat. 10 mol%, CH$_2$Cl$_2$, r.t., 48 h;
c) OsO$_4$, NMMO, t.BuOH, actone/H$_2$O, 2.5/1, r.t., 1 h; d) Raney-Ni, EtOH, r.t., 1 h;
e) Raney-Ni, H$_2$, EtOH, r.t., 1 h.

a) DIC, HOBt, DMAP, CH$_2$Cl$_2$, r.t., 120 h; b) Grubb's cat. 10 mol%, CH$_2$Cl$_2$, r.t., 95 h;

a) NaH, TBAI, THF, 0°C to r.t., 42 h; b) Grubb's cat. 20 mol%, CH$_2$Cl$_2$, r.t., 48 h;

a) DIC, HOBt, DMAP, CH₂Cl₂, r.t., 72h; b) Grubbs' cat. 10 mol%, CH₂Cl₂, r.t., 46h.

a) pyridine, DMAP, CH$_2$Cl$_2$, r.t., 24 h; b) PPh$_3$ (polystyrene carrier), THF/H2O, 100/1, r.t., 48 h;
c) Et$_3$N, CH$_2$Cl$_2$, r.t., 24 h; d) Grubb's cat. 30 mol%, CH$_2$Cl$_2$, reflux, 16 h;

a) NaH, TBAI, THF, 0°C to r.t., 24 h; b) PPh₃, THF/H₂O, 100/1, r.t., 48 h; c) DIPEA, CH₂Cl₂, r.t., 19 h; d) pyridine, DMAP, CH₂Cl₂, 0°C to r.t., 2 h; e) Grubb's cat 20 mol%, CH₂Cl₂, r.t., 18 h;

a) NaH, TBAI, THF, 0°C to r.t., 18 h; b) Grubb's cat 10 mol%, CH₂Cl₂, r.t., 48 h;

a) pyridine, DMF, 90°C, 2 h; b) Grubb's cat. 10 mol%, CH$_2$Cl$_2$, r.t., 72 h;

a) pyridine, DMAP, CH$_2$Cl$_2$, 0°C, 22 h; b) Grubb's cat. 12 mol%, CH$_2$Cl$_2$, r.t., 48 h;

a) pyridine, DMAP, CH$_2$Cl$_2$, 0°C to r.t., 18 h; b) Grubb's cat. 10 mol%, CH$_2$Cl$_2$, r.t., 46 h;

a) mCPBA, CH$_2$Cl$_2$, r.t., 72 h a) pyridine, DMAP, CH$_2$Cl$_2$, 0°C to r.t., 18 h; b) Grubb's cat. 10 mol%, CH$_2$Cl$_2$, r.t., 18 h;

PREPARATION AND USE OF CARBOHYDRATE-BASED BICYCLIC RING STRUCTURES WITH ANTIMICROBIAL AND CYTOSTATIC ACTIVITY

This application claims priority to U.S. patent application Ser. No. 09/977,478, filed Oct. 15, 2001 now U.S. Pat. No. 7,138,531.

BACKGROUND OF THE INVENTION

The invention relates generally to the synthesis and use of molecules that contain a carbohydrate scaffold and an attached ring structure with various functional groups that are designed to meet some currently unmet medical needs and, more specifically to such molecules that are designed to have anti-bacterial, anti-fungal, anti-viral, anti-protozoal, or cytostatic or anti-tumor activities.

The medical community is constantly seeking new drugs with which to treat a variety of diseases, infections, and other health issues. Principal areas of focus include products which have anti-bacterial, anti-fungal, anti-viral, anti-protozoal, or anti-tumor activities. Each of these areas face challenges that could be met or alleviated by the new class of drugs that is the subject of the present application.

Anti-Bacterial Products

Although the anti-bacterial market includes many marketed products that are efficacious, increasing bacterial drug-resistance is driving a greater focus on the resistance profiles of new products under development. Resistant strains of serious infections are emerging that cannot be satisfactorily eradicated by currently marketed antibiotics. As early as half a century ago—just a few years after penicillin was put on the market—scientists began noticing the emergence of a penicillin-resistant strain of *Staphylococcus aureus*, a common bacterium that claims membership among the human body's normal bacterial flora. Resistant strains of gonorrhea, dysentery-causing shigella (a major cause of premature death in developing countries) and salmonella followed in the wake of staphylococcus 20 to 25 years later. Since then, the problem of antimicrobial resistance has become a serious public health concern with economic, social and political implications that are global in scope and cross all environmental and ethnic boundaries. Multi drug-resistant tuberculosis (MDR-TB) is no longer confined to any one country or to those co-infected with HIV, but has appeared in locations as diverse as eastern Europe, Africa and Asia among health care workers and in the general population. Penicillin-resistant pneumococci are likewise spreading rapidly, while resistant malaria is on the rise, disabling and killing millions of children and adults each year. In 1990, almost all cholera isolates gathered around New Delhi (India) were sensitive to cheap, first-line drugs furazolidone, ampicillin, co-trimoxazole and nalidixic acid. Now, 10 years later, formerly effective drugs are largely useless in the battle to contain cholera epidemics.

In some areas of the world—most notably South-East Asia—98% of all gonorrhoea cases are multi drug-resistant which in turn contributes to the sexual transmission of HIV. In India, 60% of all cases of visceral leishmaniasis—a sandfly-borne parasitic infection—no longer respond to an increasingly limited cache of first-line drugs; while in the industrialized world, as many as 60% of hospital-acquired infections are caused by drug-resistant microbes. These infections—the most recent of which are vancomycin-resistant Enterococcus (VRE) and methicillin-resistant *Staphylococcus aureus* (MRSA), are now no longer confined to hospital wards but have entered the community at large. So far, the only drug available to treat MRSA is vancomycin—itself faltering in the face of a renewed attack by vancomycin-intermediate *Staphylococcus aureus*, otherwise known as VISA.

Although most drugs are still active, the increasing incidence of resistance means that many of them may not be for long. In the case of tuberculosis, the emergence of multi drug-resistant bacteria means that medications that once cost as little as US$ 20 must now be replaced with drugs a hundred times more expensive. Other diseases are likewise becoming increasingly impervious as currently effective drugs continue to be underused by patients who do not complete courses, and misused through indiscriminate and over-prescribing.

Researchers soon discovered that pathogens develop resistance to antimicrobials through a process known as natural selection. When a microbial population is exposed to an antibiotic, more susceptible organisms will succumb, leaving behind only those resistant to the antimicrobial onslaught. These organisms can then either pass on their resistance genes to their offspring by replication, or to other related bacteria through "conjugation" whereby plasmids carrying the genes "jump" from one organism to another. This process is a natural, unstoppable phenomenon exacerbated by the abuse, overuse and misuse of antimicrobials in the treatment of human illness and in animal husbandry, aquaculture and agriculture. Disease—and therefore resistance—also thrives in conditions of civil unrest, poverty, mass migration and environmental degradation where large numbers of people are exposed to infectious diseases with little in the way of the most basic health care.

Methicillin-resistant *Staphylococcus aureus* (MRSA) micro-organisms quickly appeared after the introduction of isoxazolyl antibiotics like; methicillin, oxacillin, and cloxacillin. They became a nosocomial problem at the end of the 1980's, with a peak in the period 1993-1995. Recently another increase in MRSA infection was noticed; about 30% of the isolated *S. aureus* species were methicillin resistant. These resistance properties were not limited to the methicillin group only; a lot of *S. aureus* were often resistant to several antibiotics with only the glycopeptides remaining e.g. vancomycin and teicopanine.

The increasing number of anti-biotic resistant gram-positive organisms has reached epidemic proportions in hospitals; up to 40% of the staphylococci were methicillin (oxacillin resistant). Among all hospitals the incidence of MRSA rose from 2.4% in 1975 to 29% in 1991. In many nursing homes and chronic care facilities, the rate of MRSA colonization exceeds 50%.

The most disturbing recent trend in nosocomial infections has been the emergence of vancomycin-resistant enterococci (VRE). These bacteria were nonexistent in the U.S. until 1989 and now account for nearly 10% of the enterococci isolated from hospitalized patients. For many isolates of VRE there is no effective therapy. VRE can be spread from patient to patient and have the propensity to survive for prolonged periods on hands and environmental surfaces. The concern is that this resistance may be transferred to organisms such as *Staphylococcus aureus* and *Clostridium difficile*, which are even greater pathogenic potential to less compromised patients.

Anti-Fungal Products

In the field of fungal infections, there are two primary diseases, superficial and systemic diseases. Although historically the smaller of the two anti-fungal markets, systemic diseases are emerging as a key area within anti-infectives and is set to expand in terms of both market size and patient potential over the next several years. Systemic fungal infections are opportunistic, affecting immuno-compromised patients with HIV and those undergoing cytoxic therapy and transplant operations. They are commonly fatal, and almost always highly debilitating to the sufferer, affecting a number of organs and proving challenging to treat. Of patients treated for aspergillosis in 1999, 90% did not respond to drug therapy, and over 50% of these died due to the infection.

Anti-Viral Products

In the area of viral infections, the report focuses on herpes, influenza, human papillomavirus, rhinovirus and respiratory syncytial virus. Although over 70% of R&D in the area of anti-virals occurs in the treatment of HIV and hepatitis, these are also markets with substantial opportunity, and ones undergoing change. The emergence of cytokines and immuno-modulatory drugs in the treatment of these infections is heralding a new era of treatment, and is set to revolutionize the structure of the market. The possibility of curative anti-viral therapy in the treatment of influenza and rhinovirus, the common cold, is drawing closer, and companies are beginning to realize the substantial potential that exists in these underserved markets. These areas are, with the exception of HIV and hepatitis, the anti-virals within which change is currently most apparent, and within which the principal new anti-viral drugs are emerging.

Cytomegalovirus Infection: (Cytomegalic Inclusion Disease)

Various infections caused by cytomegalovirus, occurring congenitally, postnatally, or at any age, ranging from inconsequential silent infection to disease manifested by fever, hepatitis, pneumonitis, and, in newborns, severe brain damage, stillbirth, or perinatal death.

Transmission of cytomegalovirus (CMV) is through blood, body fluids, or transplanted organs. Infection may be acquired transplacentally or during birth. Cytomegalic inclusion disease refers to the intranuclear inclusions found in enlarged infected cells. Prevalence in the general population increases gradually with age; 60 to 90% of adults have had CMV infection. Lower socio-economic groups tend to have a higher prevalence.

Congenital infection may be manifested only by cytomegaloviruria in an otherwise apparently normal infant. At the other extreme, CMV infection may cause abortion, stillbirth, or postnatal death from hemorrhage, anemia, or extensive hepatic or CNS damage.

Acquired infections are often asymptomatic, whether acquired postnatally or later in life. An acute febrile illness, termed cytomegalovirus mononucleosis or cytomegalovirus hepatitis, may occur.

In immunosuppressed patients, CMV is a major cause of morbidity and mortality. Disease often results from reactivation of latent virus infection. Patients may have pulmonary, GI, or CNS involvement. In the terminal phase of AIDS, CMV infection commonly causes retinitis and ulcerative disease of the colon or esophagus.

Postperfusion/posttransfusion syndrome can develop in a normal host 2 to 4 wk after transfusion with fresh blood containing CMV. It is characterized by fever lasting 2 to 3 wk, hepatitis of variable degree, splenomegaly, and a characteristic atypical lymphocytosis resembling that of infectious mononucleosis. Disease generally resembles spontaneous CMV mononucleosis, although splenomegaly is more common.

Products used up to now to treat CMV infections, are nucleoside analogs such as DHPG (ganciclovir) and (S)—HPMPC:

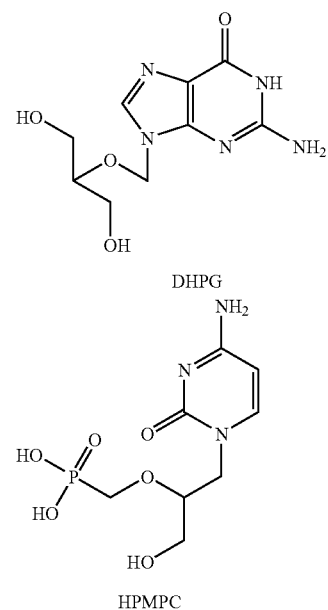

After some time, resistance is been built up against these products. Since the described products are no nucleoside analogs, it is highly possible that a different mechanism is followed to stop the virus. This makes the products interesting for treating (nucleoside resistant) CMV viruses. Moreover our identified anti-CMV products seem to be selectively active against CMV, and not against other viruses, bacteria, fingi or cancer cell lines. Such selectivity is highly demanded for pharmaceutical purposes.

Additional disadvantages of molecules such as DHPG and HPMPC are toxicity (DHPG) and difficulties to enter the cell for polar structures (HPMPC).

Herpes Zoster: (Shingles; Zona; Acute Posterior Ganglionitis)

An infection with varicella-zoster virus primarily involving the dorsal root ganglia and characterized by vesicular eruption and neuralgic pain in the dermatome of the affected root ganglia.

Herpes zoster is caused by varicella-zoster virus, the same virus that causes chickenpox. Herpes zoster occurs when the virus is reactivated from its latent state in the posterior root ganglia. Inflammatory changes occur in the sensory root ganglia and in the skin of the associated dermatome. The inflammation sometimes involves the posterior and anterior horns of the gray matter, the meninges, and the dorsal and ventral roots. Herpes zoster frequently occurs in HIV-infected patients and is more severe in immunosuppressed patients.

Geniculate zoster (Ramsay Hunt's syndrome) results from involvement of the geniculate ganglion. Pain in the ear and facial paralysis occur on the involved side. A vesicular eruption occurs in the external auditory canal, and taste may be lost in the anterior two thirds of the tongue.

Ophthalmic herpes zoster follows involvement of the gasserian ganglion, with pain and a vesicular eruption in the distribution of the ophthalmic division of the 5th nerve. Vesicles on the tip of the nose indicate involvement of the nasociliary branch of the 5th nerve and may predict the occurrence of corneal lesions. However, eye involvement may occur in the absence of lesions on the tip of the nose. An ophthalmologist should be consulted to help evaluate and prevent invasive eye disease.

Anti-Tumor Products

Cancer risk has changed over time. Some once common cancers have become rare. For example, cancer of the stomach was four times more prevalent in the United States in 1930 than it is today, probably because people today consume much less smoked, pickled, and spoiled food. On the other hand, lung cancer occurrence in the United States increased from 5 people per 100,000 in 1930 to 114 people per 100,000 in 1990, and the rate of lung cancer in women has skyrocketed. These changes are almost certainly the result of increased cigarette smoking. Cigarette smoking has also led to an increase in cancers of the mouth.

Age is an important factor in the development of cancer. Some cancers, such as Wilms' tumor, acute lymphocytic leukemia, and Burkitt's lymphoma, occur almost exclusively in young people. Why these cancers occur in the young is not well understood, but genetic predisposition is one factor. However, most cancers are more common in older people. Many cancers, including those of the prostate, stomach, and colon, are most likely to occur after age 60. Over 60 percent of the cancers diagnosed in the United States are in people over 65 years of age. Overall, the risk of developing cancer in the United States doubles every 5 years after age 25. The increased cancer rate is probably a combination of increased and prolonged exposure to carcinogens and weakening of the body's immune system, all associated with a longer life span Cancer cells develop from normal cells in a complex process called transformation. The first step in the process is initiation, in which a change in the cell's genetic material primes the cell to become cancerous. An agent called a carcinogen such as a chemical, virus, radiation, or sunlight brings about the change in the cell's genetic material. However, not all cells are equally susceptible to carcinogens. A genetic flaw in the cell or another agent, called a promoter, may make it more susceptible. Even chronic physical irritation may make cells more susceptible to becoming cancerous. In the next step, promotion, a cell that has been initiated becomes cancerous. Promotion has no effect on non-initiated cells. Thus, several factors, often the combination of a susceptible cell and a carcinogen, are needed to cause cancer.

While many drugs have demonstrated anti-tumor activities, new, more effective drugs are constantly being sought.

Anti-Protozoal Products

Malaria is by far the world's most important tropical parasitic disease, and kills more people than any other communicable disease except tuberculosis. In many developing countries, and in Africa especially, malaria exacts an enormous toll in lives, in medical costs, and in days of labour lost. The causative agents in humans are four species of *Plasmodium* protozoa (single-celled parasites)—*P. falciparum, P. vivax, P. ovale* and *P. malariae*. Of these, *P. falciparum* accounts for the majority of infections and is the most lethal. Malaria is a curable disease if promptly diagnosed and adequately treated.

The need exists for new compounds that have anti-bacterial, anti-fungal, anti-viral, anti-protozoal, or anti-tumor activities.

SUMMARY OF THE INVENTION

This patent describes the synthesis and use of new molecules with a carbohydrate scaffold and an attached ring system and thus can be considered to belong to the class of compounds general known as macrolides and ketolides. Macrolide and ketolide antimicrobials are all chemically related in that they consist of a macrocyclic lactone, the majority of them also containing amino sugar and/or neutral sugar moieties. The macrolides can be divided in two major groups: the non-polyene anti-bacterial macrolides and the polyene anti-fungal macrolides.

The macrolides are all obtained by fermentation (erythromycin, oleandomycin, josamycine, spiramycine, etc.) or by chemical modification of the natural ones (azithromycine, clarithromycine, rokitamycine, ketolides, etc.).

Non-Polyene Macrolides

The non-polyene macrolides are of great interest because their anti-bacterial activity. In general, macrolides are active mainly against gram-positive bacteria (*Staphylococcus, Streptococcus* and *Diplococcus*) and possess only limited activity against gram-negative bacteria (e.g. *Neisseria gonorrhoea, N. Meningitis*, etc.). In general, polyene macrolides have very low or no impact on eukaryotic cells. Because of the intensive use of these macrolides, resistant strains of bacteria have developed, and cross-resistance to different macrolides has been generally observed. Some bacteria have become resistant to all the macrolides: Methicillin resistant *Staphylococcus aureus*, eneterobacteria, *Acinetobacter, Pseudomonas*. Resistance to macrolides can be determined by lack of antibiotic penetration, which makes most gram-negative bacteria resistant at neutral pH, by efflux pumps, receptor alteration and biochemical inactivation. Biochemical inactivation of erythromycin and oleandomycin is widespread in enterobacteria highly resistant to these antibiotics and result from hydrolysis of the lactone ring in the antibiotics by plasmid encoded erythromycin esterases.

Polyene Macrolides

The polyene macrolides are characterized by large (20-to 44-membered) lactone rings containing three to eight conjugated double bonds, usually combined with one sugar moiety. Typical polyene macrolides show excellent anti-fungal activity. They are substantially ineffective against bacteria. The anti-fungal spectrum differs with structures to a small extent. Because of their potent anti-fungal and anti-protozoal activity, they are useful practically. Several heptaenes (Amphotericin B) and tetraenes (Pimaricin) are used in medicine. Different types of changes in the lipid composition of resistant mutants have been found. Phenotypic resistance has also been described for polyene macrolides. This phenotypic resistance is due to a cell wall component, probably a long-chain β-glucan.

The molecules of the present invention have a general structure as shown below.

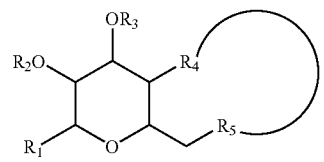

The molecules consist of a carbohydrate scaffold, carrying two side chains, which can form a macrocyclic ring. As a scaffold, pyranose sugars are used. Also other sugars (pentoses or hexoses) can be used. As the orientation of the side chains plays an important role in macrocyclizations, one of the synthetic functions of the scaffold is to keep the side chains in the correct orientation. Moreover, carbohydrate substructures often occur in natural macrolides, and can contribute importantly to the biological activity of macrolide compounds. There is a wide range of possible variations of the different substituents $R_1$, R2 and R3, such as H, alkyl, aryl, O-aryl, S-aryl, OH, OR, halogens, —OOCR, COOR, —COR etc. Of course, other scaffolds derived from a glycopyranose or a glycofuranose or other sugars can too be used, as well as scaffolds derived from a substituted (hetero) aromatic ring. The side chains can be coupled to the scaffold via a range of functionalities such as an ether bond, an ester bond, an amide bond, an amine bond, a thioether bond, etc. The side chains can be cyclisized by an alkane or an alkene bond. The macrocycle can vary in length and can be functionalised with groups such as OH, O-alkyl, O-aryl, O-aroyl, —NHR, epoxides or O-glycosil. The macrocycle may contain none, one or multiple double bonds. Also molecules with a carbohydrate scaffold with an open ring structures have been tested.

These molecules have been found to have anti-bacterial, anti-fungal, anti-viral, anti-protozoal, or anti-tumor activities, and particularly anti-viral activity, when used in assays known in the art.

An object of the invention is to provide new, synthesized macrolide and ketolide compounds that have anti-bacterial, anti-fungal, anti-viral, anti-protozoal, or anti-tumor activities.

Another object of the invention is to provide new, synthesized macrolide and ketolide compounds which can be administered to humans and animals for the treatment or amelioration of bacterial, fungal, viral or protozoal infections or tumors.

These and other objects of the invention will be apparent to those skilled in the art upon a review of this specification, the associated drawings, and the appended claims.

BRIEF DESCRIPTION OF THE DRWAINGS

DETAILED DESCRIPTION OF THE PREFERRED EMBODIMENTS

Figure 1:
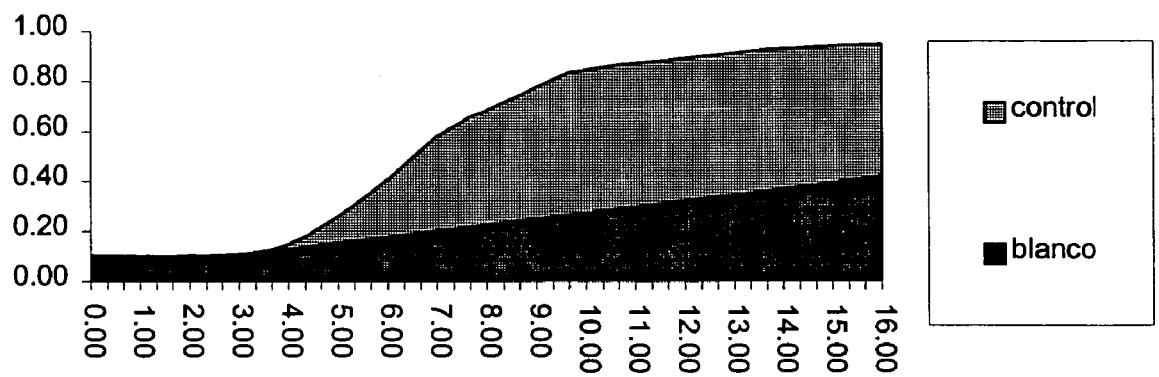
FIG. 1 is a diagrammatical representation of the inhibition of bacterial growth exhibited by the present invention.

Examples of some new synthesized macrolide and ketolide compounds of the present invention are listed in Table 1.

TABLE 1

Examples of Described Molecules

| Code | Structure | $R_1$ | $R_2$ | $R_3$ | $R_4$ | $R_5$ |
|---|---|---|---|---|---|---|
| KPE00001056 | 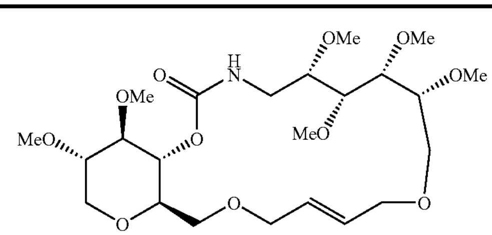 | —H | —Me | —Me | | -carbamate-C6-alkyl-ether-C4-alkenyl-ether- |

TABLE 1-continued

Examples of Described Molecules

| Code | Structure | R₁ | R₂ | R₃ | R₄ | R₅ |
|---|---|---|---|---|---|---|
| KPE00001002 | 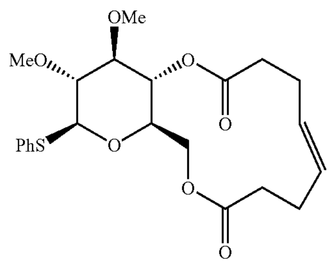 | —SPh | —Me | —Me | | -ester-C6-alkenyl-ester- |
| KPE00001007 | 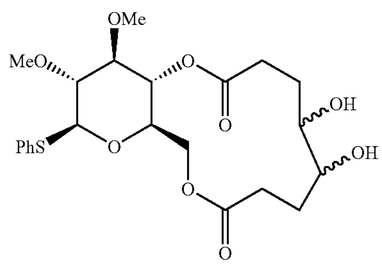 | —SPh | —Me | —Me | | -ester-C6-alkyl-ester- |
| KPE00001010 | 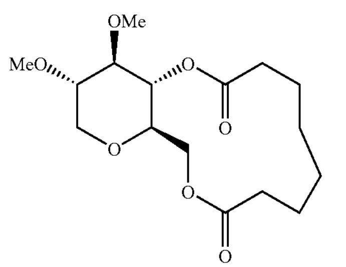 | —H | —Me | —Me | | -ester-C6-alkyl-ester- |
| KPE00001006 | 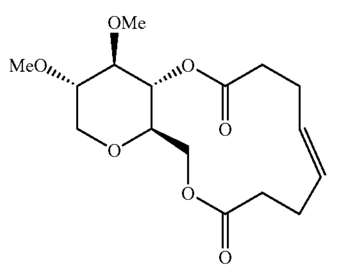 | —H | —Me | —Me | | -ester-C6-alkenyl-ester- |
| KPE00001037 | 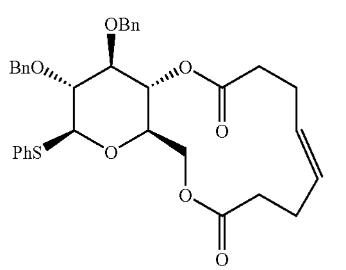 | —SPh | —Bn | —Bn | | -ester-C6-alkenyl-ester- |
| KPE00001009.1 | 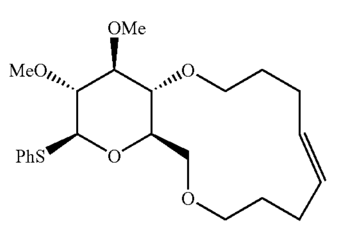 | —SPh | —Me | —Me | | -ether-C8-alkenyl-ether- |

TABLE 1-continued
Examples of Described Molecules
| Code | Structure | R₁ | R₂ | R₃ | R₄ | R₅ |
|---|---|---|---|---|---|---|
| KPE00001009.2 | 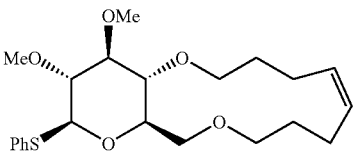 | —SPh | —Me | —Me | | -ether-C8-alkenyl-ether- |
| KPE00001041 | 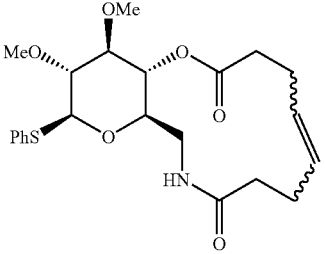 | —SPh | —Me | —Me | | -ester-C6-alkenyl-amide- |
| KPE00001042 | 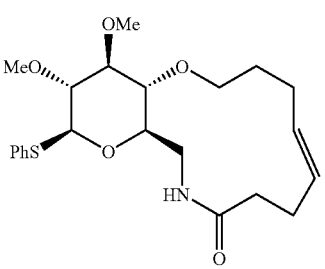 | —SPh | —Me | —Me | | -ether-C7-alkenyl-amide- |
| KPE00001014 | 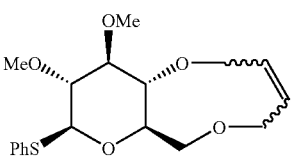 | —SPh | —Me | —Me | | -ether-C4-alkenyl-ether- |
| KPE00001018 | 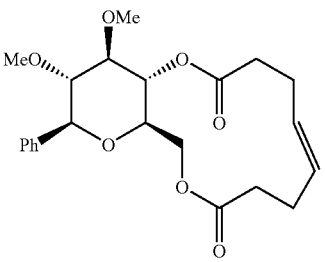 | —Ph | —Me | —Me | | -ester-C6-alkenyl-ester- |
| KPE00001022 | 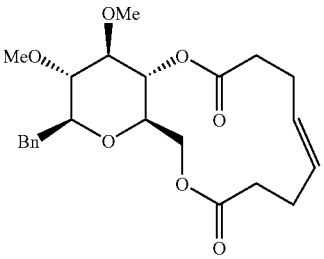 | —Bn | —Me | —Me | | -ester-C6-alkenyl-ester- |

TABLE 1-continued

Examples of Described Molecules

| Code | Structure | $R_1$ | $R_2$ | $R_3$ | $R_4$ | $R_5$ |
|---|---|---|---|---|---|---|
| KPE00001040(E + Z) | 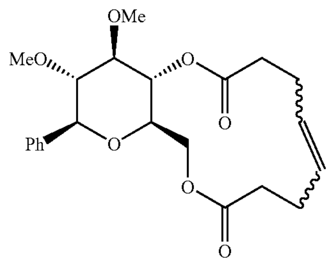 | —Ph | —Me | —Me | | -ester-C10-alkenyl-ester- |
| KPE00001039 | 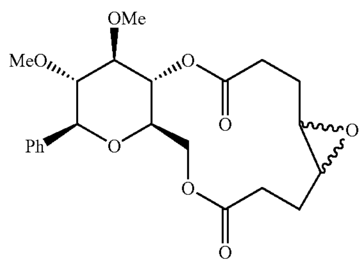 | —Ph | —Me | —Me | | -ester-C6-alkyl-ester- |
| KPE00001031E | 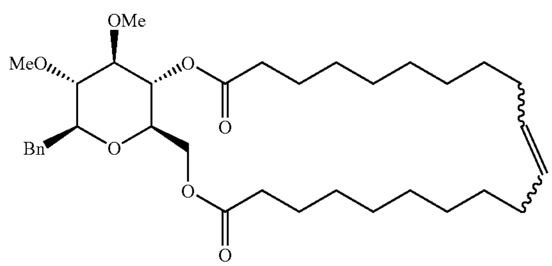 | —Bn | —Me | —Me | | -ester-C18-alkenyl-ester- |
| KPE00001016.1 | 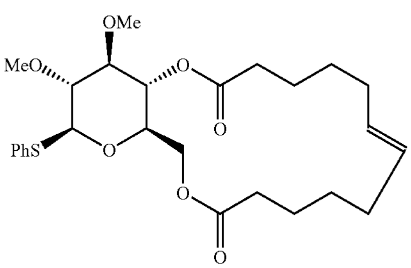 | —PhS | —Me | —Me | | -ester-C10-alkenyl-ester- |
| KPE00001016.2 | 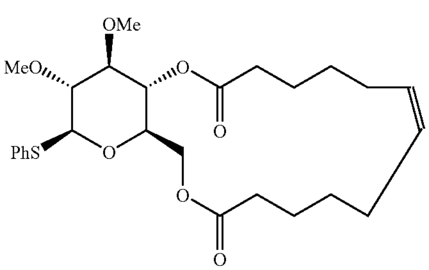 | —PhS | —Me | —Me | | -ester-C10-alkenyl-ester- |
| KPE00001011 | 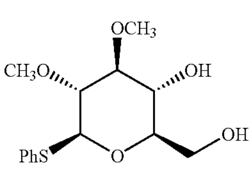 | —SPh | —Me | —Me | —OH | —OH |

TABLE 1-continued

Examples of Described Molecules

| Code | Structure | R₁ | R₂ | R₃ | R₄ | R₅ |
|---|---|---|---|---|---|---|
| KPE00001015 | 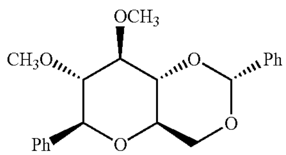 | —Ph | —Me | —Me | | —OCH(Ph)CH₂O— |
| KPE00001019 | 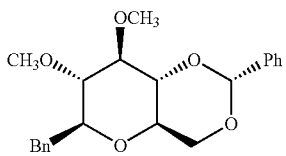 | —Bn | —Me | —Me | | —OCH(Ph)CH₂O— |
| KPE00001020 | 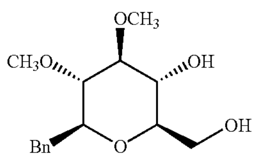 | —Bn | —Me | —Me | —OH | —OH |
| KPE00001044 | 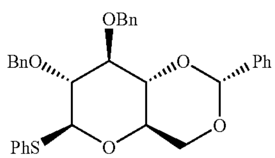 | —SPh | —Bn | —Bn | | —OCH(Ph)CH₂O— |
| KPE00001045 | 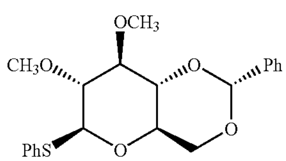 | —SPh | —Me | —Me | | —OCH(Ph)CH₂O— |
| KPE00001046 | 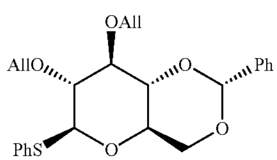 | —SPh | —All | —All | | —OCH(Ph)CH₂O— |
| KPE00001048 | 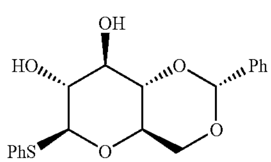 | —SPh | —H | —H | | —OCH(Ph)CH₂O— |
| KPE00001049 | 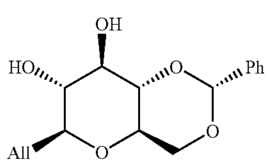 | —All | —H | —H | | —OCH(Ph)CH₂O— |
| KPE00001050 | 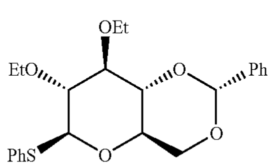 | —SPh | —Et | —Et | | —OCH(Ph)CH₂O— |

TABLE 1-continued

Examples of Described Molecules

| Code | Structure | R₁ | R₂ | R₃ | R₄ | R₅ |
|------|-----------|------|------|------|------|--------------|
| KPE00001051 | (structure with OMe, MeO, All, Ph, O) | —All | —Me | —Me | | —OCH(Ph)CH₂O— |
| KPE00001052 | (structure with OH, HO, Ph, O, Ph) | —Ph | —H | —H | | —OCH(Ph)CH₂O— |
| KPE00001053 | (structure with OH, HO, Bn, O, Ph) | —Bn | —H | —H | | —OCH(Ph)CH₂O— |
| KPE00001015 | (structure with OCH₃, CH₃O, Ph, O, Ph) | —Ph | —Me | —Me | | —OCH(Ph)CH₂O— |

Depending on the structure and functionality of these new synthesised molecules, a different and also selective biological activity can be observed. This structured modification also allows overcoming of the resistance of some micro-organisms to antimicrobial products, e.g., using a lactam bond instead of a lacton bond to close the macrocyclic ring (KPE00001041). The biological activity, synthesis, purification, analytical and spectral data of the mentioned compounds are further described below.

Also included are pharmaceutically acceptable derivatives of the foregoing compounds, i.e., any pharmaceutically acceptable salt, ester, or salt of such ester of such compound, or any other adduct or derivative which, upon administration to a patient, is capable of providing (either directly or indirectly) a compound as described herein, or a metabolite or residue thereof. Pharmaceutically acceptable derivatives thus include, among others, pro-drugs of the compounds. A pro-drug is a derivative of a compound usually with significantly reduced pharmacological activity, which contains and additional moiety which is susceptible to removal in vivo yielding the parent molecule as the pharmacologically active species.

BIOLOGICAL ACTIVITY

Anti-Viral Activity

The new compounds were screened against various pathogenic viruses such as the human immunodefeciency virus (HIV), herpes simplex virus (HSV), vaccinia virus (VV), the varicella zoster virus (VZV) and the human cytomegalovirus (CMV). For determination of antiviral activity against CMV, human embryonic lung fibroblast (HEL) cells grown in 96-well microplates were infected with 20 PFU virus/well. After 2 h of incubation at 37° C., the infected cells were replenished with 0.1 ml of medium containing serial dilutions of the test compound. On day 7 the plaques were counted microscopically after staining the cells with Giemsa's solution. The minimum antiviral concentration was expressed as the dose required to inhibit virus-induced plaque formation by 50%.

The results are presented in Table 2 (the CMV data for the compounds with no table entries are presented in Table 6).

TABLE 2

Anti-viral Activity

| | EC$_{50}$(μg/ml)$^a$ | | | | | IC$_{50}$ (μg/ml)$^b$ | | | |
| | | | | | | VZV (HEL) | | CMV | |
| Compound | HIV-1 (III$_B$) (CEM) | HIV-2 (ROD) (CEM) | HSV-1 (KOS) (E$_6$SM) | HSV-2 (G) (E$_6$SM) | VV (E$_6$SM) | OKA | YS | AD-169 Strain | David strain |
|---|---|---|---|---|---|---|---|---|---|
| KPE00001002 | >100 | >20 | >16 | >16 | >16 | >20 | >50 | >20 | ND |
| KPE00001014 | >100 | >100 | >400 | 240 | >400 | >50 | >50 | >50 | ND |
| KPE00001016.1 | >4 | >4 | >3.2 | >3.2 | >3.2 | 5 | 22 | 10 | 10 |
| KPE00001016.2 | >100 | >100 | >3.2 | >3.2 | >3.2 | >50 | >50 | >20 | >20 |
| KPE00001018 | >20 | >100 | >16 | >16 | >16 | >50 | >50 | >20 | ND |
| KPE00001022 | >20 | >20 | >80 | 80 | 80 | >20 | >20 | >5 | ND |
| KPE00001031(E) | >100 | >20 | ≧400 | >400 | >400 | >5 | 15 | >5 | ND |
| KPE00001044 | N.D.$^b$ | N.D. | >3.2 | >3.2 | >3.2 | >2 | >2 | | |
| KPE00001045 | N.D. | N.D. | >3.2 | >3.2 | >3.2 | >2 | >2 | | |
| KPE00001048 | N.D. | N.D. | >80 | >80 | >80 | >50 | >50 | | |
| KPE00001046 | N.D. | N.D. | >3.2 | >3.2 | >3.2 | >2 | >2 | | |
| KPE00001047 | N.D. | N.D. | >3.2 | >3.2 | >3.2 | >2 | >2 | | |
| KPE00001049 | N.D. | N.D. | >400 | 240 | >400 | >50 | >50 | | |
| KPE00001050 | N.D. | N.D. | >3.2 | >3.2 | >3.2 | >5 | >5 | | |
| KPE00001051 | N.D. | N.D. | >16 | >16 | >16 | >20 | >20 | | |
| KPE00001015 | >4 | >4 | >80 | >80 | >80 | 13 | 14 | | |
| KPE00001019 | >100 | >100 | >80 | >80 | >80 | >5 | >5 | | |
| KPE00001044 | N.D.$^b$ | N.D. | >3.2 | >3.2 | >3.2 | >2 | >2 | | |

$^a$50% effective concentration or compound concentration required to inhibit HIV-induced cytopathicity in human CEM cell cultures, HSV- and VV-induced cytopathicity in human embryo fibroblast E$_6$SM cell cultures, and VZV-induced plaque formation in human embryonic lung HEL cell cultures by 50%
$^b$Inhibitory concentration required to reduce virus plaque formation by 50%. Virus input was 100 plaque forming units (PFU)
ND: not determined Studies on the anti-viral activity of the compounds clearly showed an anti-viral activity for compound KPE00001016.1. In addition, a good selectivity was observed: KPE00001016.1 was especially active against VZV and CMV, compared to other viruses.

Anti-Tumor Activity

The compounds were tested for anti-tumor activity via the inhibitory effects on the proliferation of murine leukemia cells (L1210/0), murine mammary carcinoma cells (FM3A), human T-lymphocyte cells (Molt4/C8, CEM/0) and human cervix carcinoma cells (HeLa).

Cytotoxicity measurements were based upon the inhibition of HEL cell growth: HEL cells were seeded at a rate of 3×10$^3$ cells per well into 96-well microplates and allowed to proliferate for 24 h in Eagle's minimum essential medium (MEM) containing 10% inactivated fetal calf serum. The medium was then replaced by MEM containing various concentrations of the test compound. After three days incubation at 37° C., when the cell monolayer was 70% confluent, the cell number was determined with the Coulter counter. The minimum cytotoxic concentration was defined as the concentration required to reduce cell growth by 50%.

The results are presented in Table 3.

TABLE 3

Cytostatic activity of the compounds

| | IC$_{50}$ (μg/ml)$^a$ | | | | |
| Compound | L1210/0 | FM3A/0 | Molt4/C8 | CEM/0 | HeLa |
|---|---|---|---|---|---|
| KPE00001002 | >200 | >200 | >200 | >200 | >200 |
| KPE00001014 | >200 | >200 | >200 | >200 | >200 |
| KPE00001016.1 | 20 ± 7 | 108 ± 9 | 39 ± 1 | 23 ± 0.5 | 19 ± 5 |
| KPE00001016.2 | 158 ± 10 | >200 | 78 ± 53 | 36 ± 16 | 169 ± 44 |
| KPE00001018 | >200 | >200 | >200 | 132 ± 13 | >200 |
| KPE00001022 | 80 ± 0 | 82 ± 14 | 69 ± 6 | 48 ± 15 | ±167 ± 47 |
| KPE00001031(E) | >200 | ≧200 | ≧200 | ≧200 | >200 |
| KPE00001044 | >200 | 130 ± 61 | >200 | >200 | N.D. |
| KPE00001045 | >200 | >200 | >200 | >200 | N.D. |
| KPE00001048 | 103 ± 10 | 171 ± 41 | 78 ± 12 | 75 ± 31 | N.D. |
| KPE00001046 | >200 | 137 ± 60 | >200 | >200 | N.D. |
| KPE00001047 | >200 | >200 | >200 | >200 | >200 |
| KPE00001049 | >200 | >200 | >200 | >200 | >200 |
| KPE00001050 | >200 | >200 | >200 | >200 | >200 |
| KPE00001051 | >200 | >200 | >200 | >200 | >200 |

TABLE 3-continued

Cytostatic activity of the compounds $IC_{50}$ (µg/ml)[a]

| Compound | L1210/0 | FM3A/0 | Molt4/C8 | CEM/0 | HeLa |
|---|---|---|---|---|---|
| KPE00001015 | ≧200 | >200 | 62 ± 3 | 81 ± 10 | 104 ± 65 |
| KPE00001019 | >200 | >200 | ≧200 | ≧200 | >200 |

[a]50% inhibitory concentration
N.D.—not determined

From the cytostatic studies can be concluded that compound KPE00001016.1 and KPE00001022 showed good cytostatic activity.

Anti-Bacterial and Anti-fungal Activity

For the determination of the anti-bacterial and anti-fungal activity the Bioscreen C Analyser Labsystems, Finland, was used. This is an automated reader-incubator. It measures growth continuously by vertical photometry (optical density), processes the data and provides a print out of the results. The area under the growth curve is automatically determined via the Biolink software.

The inoculum size of the bacteria is standardized to approximately $5 \times 10^5$ CFU/ml.

The inoculum size of the yeast is standardized to $0.5$-$2.5 \times 10^3$ CFU/ml.

The inoculum size of the mould is standardized to $0.4$-$5.0 \times 10^4$ CFU/ml.

For bacteria, the 100-honey-well plates containing test chemical, Mueller-Hinton broth and inoculum (=sample) are incubated at 35° C. for 16 hours. Also wells without inoculum are incubated (=blanco). Yeasts are incubated 35° C. for 24 hours in RPMI 1640+MOPS buffer at 165 mM. Moulds also in RPMI 1640+MOPS buffer at 165 mM are incubated 25° C. for 5 days. All micro-organisms are screened against a known concentration of the reference antibiotics or antimycotics such as vancomycin, penicillin G, gentamicin or amphotericin B. The growth curve and the area under the growth curve can be determined using the Biolink software; this is illustrated in FIG. 1.

Figure 2:
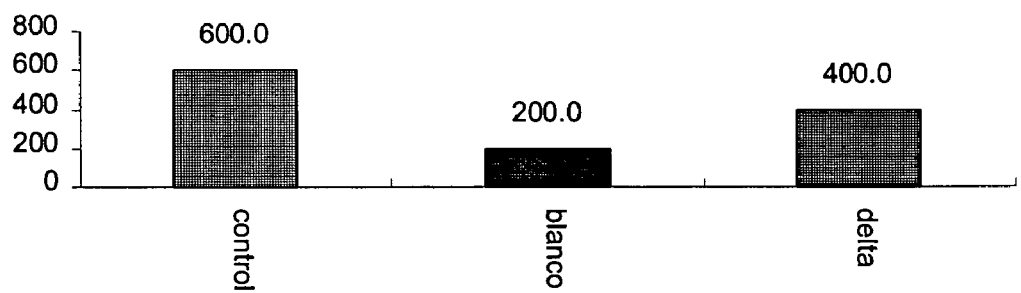
FIG. 2 is a diagrammatical representation of the bacterial growth in samples treated and untreated by the present invention.

The area of the blanco is subtracted from the area of the sample, this number (delta) gives us an indication of the biological activity of the molecules tested and can be expressed as a % of growth at a specific dose compared to a negative control that has a value of 100, illustrated in FIG. 2. Screening of each dose of a specific compound is repeated 5 times. The dose used for all new molecules in all tests is 25 PPM or 25 µg/ml.

Anti-Bacterial Activity

In Table 4 the results of the anti-bacterial activity is given for the new molecules. The micro-organisms used are *Staphylococcus aureus*, MRSA, VRE, *Enterococcus faecalis*, *Salmonella typhimurium* and *Pseudomonas aeruginosa*.

TABLE 4

Anti-bacterial activity of the compounds

% of growth at 25 PPM compared to the negative control

| Compound | E. faecalis ATTC29212 LMG 8222 | VRE ATCC700221 | S. aureus ATTC29213 LMG10147 | MRSA ATCC33591 LMG10147 | P. aeruginosa ATCC27853 LMG16217 | S. typhimurium ATTC700408 LMG16217 |
|---|---|---|---|---|---|---|
| Negative control | 100 | 100 | 100 | 100 | 100 | 100 |
| KPE00001002 | 94.9 | 94 | 93.2 | 100 | 92.2 | 93.7 |
| KPE00001006 | 92.5 | 96.5 | 94.7 | 99.7 | 87.3 | 94.6 |
| KPE00001007 | 97 | 93.0 | 94.9 | 97.8 | 86.2 | 89.7 |
| KPE00001009.1 | 87.5 | 82 | 98.3 | 107.3 | 91.6 | 90.1 |
| KPE00001009.2 | 85.5 | 86.4 | 100.4 | 110.8 | 67.6 | 90.1 |
| KPE00001010 | 90.6 | 93 | 101.5 | 110.5 | 80.7 | 88.8 |
| KPE00001014 | 95 | 88.4 | 105 | 112.7 | 96.7 | 87.2 |
| KPE00001016.1 | 76.5 | 61.8 | 102.8 | 114.6 | 29 | 76.4 |
| KPE00001016.2 | 98.4 | 81 | 97 | 104.1 | 79.8 | 87 |
| KPE00001018 | 94.9 | 94.5 | 100.4 | 100 | 59.8 | 96.6 |
| KPE00001022 | 96.1 | 87 | 102.3 | 109.8 | 90.9 | 94 |
| KPE00001031E | 85.5 | 85.4 | 100 | 103.5 | 89.6 | 91.7 |
| KPE00001037 | 97.6 | 90 | 98.5 | 107.3 | 89.3 | 91 |
| KPE00001039 | 94.1 | 93 | 97.7 | 102.2 | 91.3 | 97 |
| KPE00001040[a] | 85.1 | 83.4 | 94 | 99.7 | 78.5 | 89 |
| KPE00001041 | 68.2 | 93 | 56.7 | 75.6 | 83.3 | 96.6 |
| KPE00001042 | 93.3 | 96 | 97 | 103.5 | 94.7 | 98 |
| KPE00001056 | 111 | 91 | 104.7 | 113 | 106.2 | 93.7 |
| KPE00001011 | 89.0 | 79.0 | 89.0 | 90.5 | 85.0 | 92.1 |
| KPE00001015 | 86.0 | 67.8 | 103.8 | 116.8 | 90.4 | 87.2 |
| KPE00001019 | 104.3 | 97.0 | 109.2 | 104.4 | 104.9 | 94.3 |
| KPE00001020 | 98.4 | 99.0 | 97.9 | 99.0 | 94.4 | 92.3 |

[a]E + Z

From the anti-bacterial studies it can be concluded that KPE00001016.1 has a good anti-bacterial activity especially against *P. aeruginosa* and to a lesser extent the resistant bacteria VRE.KPE00001041 has a good anti-bacterial activity against gram-positive bacteria including resistant strains such as MRSA.

Anti-Fungal Activity

In Table 5 the anti-fungal activity is given for the new molecules. The micro-organisms used were *Candida albicans* (a typical yeast) and *Microsporum gypseum* (a typical mold).

Also for the determination of the anti-fungal activity the Bioscreen C Analyser Labsystems Oy, Finland was used. It measures growth continuously by vertical photometry (optical density), processes the data and provides a print out of the results. The area under the growth curve is automatically determined via the Biolink software.

The inoculum size of the yeast is standardized to 0.5-2.5×$10^3$ CFU/ml. The inoculum size of the mould is standardized to 0.4-5.0×$10^4$ CFU/ml. Yeasts are incubated 35° C. for 24 hours in RPMI 1640+MOPS buffer at 165 mM. Moulds also in RPMI 1640+MOPS buffer at 165 mM are incubated 25° C. for 5 days.

As a control, all micro-organisms are screened against some reference antibiotics with known MIC. Screening of each dose of a specific compound is repeated 5 times.

TABLE 5

Anti-fungal activity of the compounds

| | % of growth at a dose of 25 PPM compared to the negative control | |
| --- | --- | --- |
| Compound | Candida albicans IHEM 10284 - ATCC 24433 | Microsporum gypseum IHEM 3999 - ATCC 14683 |
| Negative control | 100 | 100 |
| KPE00001002 | 105.3 | 64 |
| KPE00001006 | 93.1 | 62 |
| KPE00001007 | 94.7 | 76 |
| KPE00001009.1 | 93.9 | 60 |
| KPE00001009.2 | 103.2 | 54 |
| KPE00001010 | 95.5 | 60 |
| KPE00001014 | 96.0 | 69 |
| KPE00001016.1 | 98.4 | 74 |
| KPE00001016.2 | 85 | 58 |
| KPE00001018 | 93.5 | 79 |
| KPE00001022 | 91.5 | 67 |
| KPE00001031E | 88.3 | 62 |
| KPE00001037 | 87.4 | 73 |
| KPE00001039 | 96.4 | 77 |
| KPE00001040(E + Z) | 101.2 | 64 |
| KPE00001041 | 78.1 | 81 |
| KPE00001042 | 90.3 | 79 |
| KPE00001056 | 101.0 | 77 |
| KPE00001011 | 79.3 | 76.4 |
| KPE00001015 | 66.6 | 66.0 |
| KPE00001019 | 98.5 | 66.0 |
| KPE00001020 | 91.0 | 78.0 |

KPE00001015 had the best activity against a yeast and compound KPE00001009.2 had the best anti-mold activity of the tested compounds. Again, a nice selectivity is observed.

Anti-CMV Activity and Cytotoxicity Measurements

For determination of antiviral activity against CMV, human embryonic lung fibroblast (HEL) cells grown in 96-well microplates were infected with 20 PFU virus/well. After 2 h of incubation at 37° C., the infected cells were replenished with 0.1 ml of medium containing serial dilutions of the test compound. On day 7 the plaques were counted microscopically after staining the cells with Giemsa's solution. The minimum antiviral concentration was expressed as the dose required to inhibit virus-induced plaque formation by 50%.

Cytotoxicity measurements were based upon the inhibition of HEL cell growth: HEL cells were seeded at a rate of 3×$10^3$ cells per well into 96-well microplates and allowed to proliferate for 24 h in Eagle's minimum essential medium (MEM) containing 10% inactivated fetal calf serum. The medium was then replaced by MEM containing various concentrations of the test compound. After three days incubation at 37° C., when the cell monolayer was 70% confluent, the cell number was determined with the Coulter counter. The minimum cytotoxic concentration was defined as the concentration required to reduce cell growth by 50%. The results of the cytotoxic screening are presented in Table 6.

TABLE 6

Cytotoxicity and activity against cytomegalovirus (CMV)

| | Anti-CMV activity | | Cytotoxicity (µg/ml) | |
| --- | --- | --- | --- | --- |
| | $IC_{50}$ (µg/ml)[a] | | Cell | |
| Compound | AD-169 strain | Davis strain | morphology (MCC)[b] | Cell growth $(CC_{50})$[c] |
| KPE00001044 | >2 | >2 | 5 | >50 |
| KPE00001045 | >5 | >5 | 20 | 50 |
| KPE00001048 | 33 | 35 | >50 | >50 |
| KPE00001046 | >5 | >5 | 20 | >50 |
| KPE00001047 | >20 | >20 | 50 | >50 |
| KPE00001049 | >50 | >50 | >50 | >50 |
| KPE00001050 | >50 | >50 | >50 | >50 |
| KPE00001051 | >50 | >50 | >50 | >50 |
| KPE00001015 | 2.0 | 2.7 | 50 | >50 |
| KPE00001019 | 20 | 5 | 20 | >50 |

[a]Inhibitory concentration required to reduce virus plaque formation by 50%. Virus input was 100 plaque forming units (PFU).
[b]Minimum cytotoxic concentration that causes a microscopically detectable alteration of cell morphology.
[c]Cytotoxic concentration required to reduce cell growth by 50%.

Pharmaceutical Compositions

The present invention also pertain to,pharmaceutical compositions containing at least one macrolide as described above and a pharmaceutically acceptable carrier forming a macrolide pharmaceutical composition. The macrolide will be present in an effective amount to prevent or treat pathogenic infections or tumor formation when administered to a subject in need thereof. The pharmaceutical composition also can contain other additives which do not detrimentally affect the ability of the macrolide to perform its intended function, numerous examples of which are known in the art.

The compounds can exist in free form or, where appropriate or desired, in the form of a pharmaceutically acceptable derivative, including an ester, salt, etc. Pharmaceutically acceptable salts and their preparation are well-known to those of skill in the art. The pharmaceutically acceptable salts of such compounds include the conventional non-toxic salts or the quaternary ammonium salts of such compounds which are formed, for example, from inorganic or organic acids of bases. The compound of this invention may form hydrates or solvates. It is known to those of skill in the art that charged compounds form hydrated species when lypholized with water, or form solvated species when concentrated in a solution with an appropriate organic solvent.

The amount of the macrolide which will be effective in the treatment or prevention of a condition or disease will depend in part on the characteristics of the condition or disease and can be determined by standard clinical techniques. In vitro or in vivo assays may optionally be employed to help identify optimal dosage ranges. Effective doses may be extrapolated from dose-response curves, derived from in vitro analysis, or preferably from animal models. The precise dosage levels should be determined by the attending physician or other health care provider and will depend upon well-known factors, including the route of administration, and the age, body weight, sex, and general health of the individual; the nature, severity and clinical stage of the condition or disease; and the use or lack of concomitant therapies.

The effective dose of the macrolide will typically be in the range of about 0.01 to about 50 mg/kg, and preferably about 0.1 to 10 mg/kg of mammalian body weight per day, administered in single or multiple doses. Generally, the compound may be administered in a daily dose range of about 1 to about 2000 mg per patient.

Synthesis

All reactions were carried out in dry solvents under inert atmosphere (argon or nitrogen) in dry glassware, unless stated otherwise. The reactions were monitored by thin layer chromatography (Merck silicagel 60F254 0.25 mm thickness).

Tetrahydrofuran, diethylether, dimethyl ethylene glycol and toluene were distilled from sodium/benzofenon. Methylene chloride was distilled from phosphorpentoxide. Triethylamine, diisopropylethylamine and pyridine were distilled from calciumhydride. Dimethylformamide was distilled from calciumhydride and stored on molecular sieves (4 Å). The Grubbs' catalyst was used from Strem Chemicals and stored under argon atmosphere.

All products were purified by flash chromatography on silicagel (Merck silicagel 60F254) or by HPLC on an Rsil-phase with RI detection, unless stated otherwise. Melting points were measured with a melting microscope and are not corrected. $R_f$ values are referring to Merck silica 60F254. Optical rotation values of homochiral products were measured with a Perkin-Elmer 241 polarimeter. IR spectra were recorded on a Perkin-Elmer 1600 series FTIR. Mass spectra were recorded on an "atmospheric pressure electroyspray-ionization" Hewlett-Packered 1100 MSD massdetector. $^1$H-NMR spectra were recorded at 500 MHz (Brücker AN-500). $^{13}$C-NMR spectra were recorded at 125 MHz (Brücker AN-500).

EXAMPLE 1

Synthesis of penta-acetate (Molecule 1.2)

A solution of $NaN_3$ (5.975 g, 91.9 mmol) in 15 ml of $H_2O$ was cooled in an ice bath and treated with 25 ml of $CH_2Cl_2$. The resulting biphasic mixture was stirred vigorously and treated with $Tf_2O$ (3.09 ml, 5.186 g, 18.38 mmol) over a period of 5 minutes. The reaction was stirred at ice bath temperature for 2 h, the organic phase was separated and the aqueous phase was extracted twice with $CH_2Cl_2$. The total volume of the reagent solution was 50 ml. The organics were extracted once with 50 ml of a saturated $Na_2CO_3$ solution and used without further purification.

Figure 3:
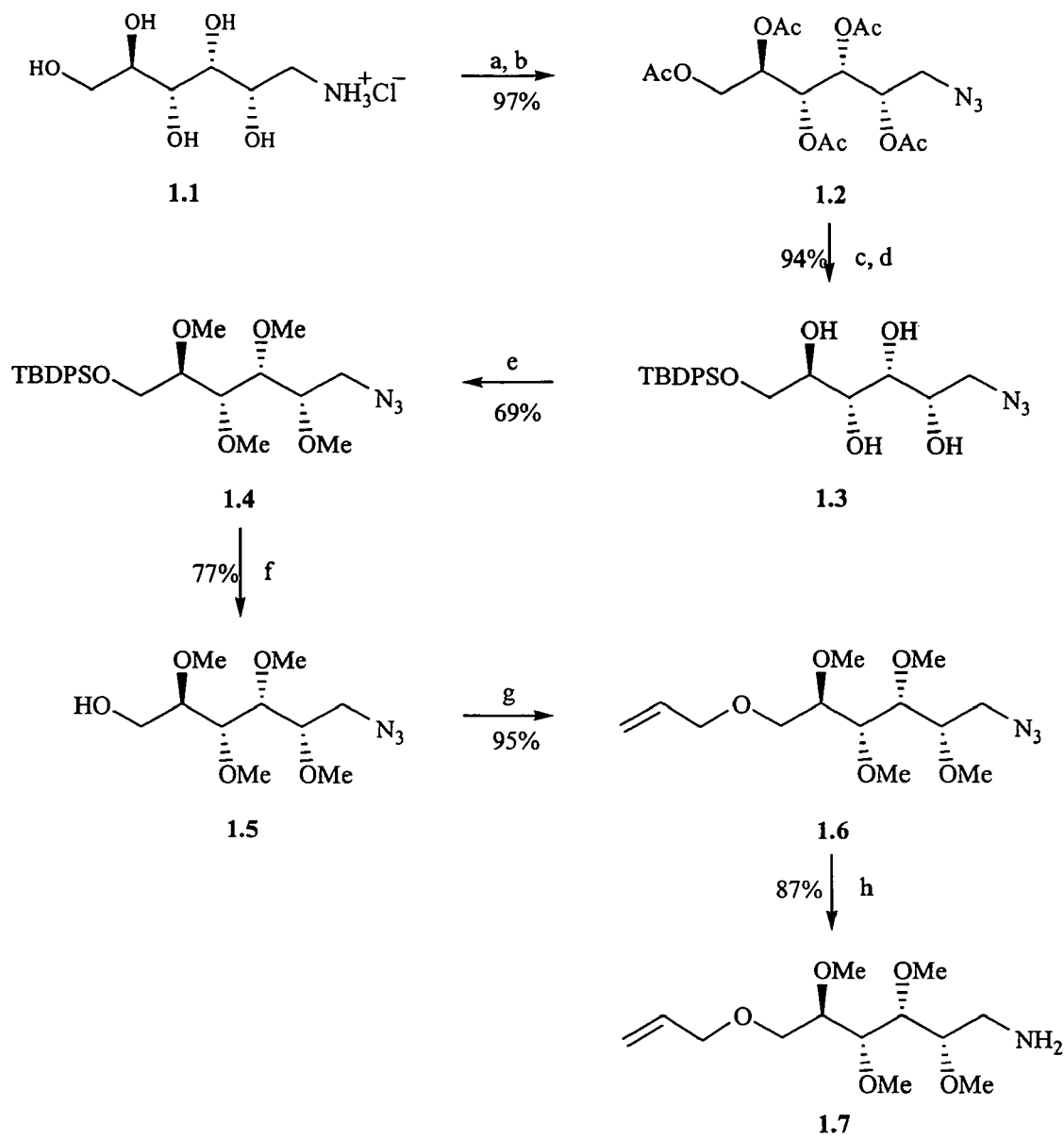
FIG. 3 is a diagrammatical representation of the synthesis scheme of side-chain Molecule 1.7 of the present invention.

Two grams of the resulting compound, Molecule 1.1 (FIG. 3), (9.19 mmol) was dissolved in 30 ml of $H_2O$ and treated with $K_2CO_3$ (1.905 g, 13.79 mmol) and $CuSO_4$ hydrate (0.023 g, 0.92 mmol). To this solution was added 60 ml of MeOH and the $TfN_3$ solution. Then, more MeOH was added to homogeneity. The reaction was allowed to stir for 18 h and the solvent was removed in vacuo. The residue was acetylated using 45 ml of $Ac_2O$ and 75 ml of pyridine with a catalytic amount of DMAP (0.1 g, 0.82 mmol) and worked up after 3 h by removal of solvent and extraction with $H_2O$ (3×100 ml) from EtOAc (200 ml). Column chromatography of the residue over silica gel (cyclohexane/ethyl acetate: 65/35) afforded the per acetylated 1-azido-1-deoxy-D-sorbitol (Molecule 1.2; FIG. 3) as white crystals (3.704 g, 8.87 mmol, 97%).

Formula: $C_{16}H_{23}N_3O_{10}$ (MM=417.4)
$R_f$: (cyclohexane/ethyl acetate: 65/35): 0.26
mp=70° C.
$\{\alpha\}_D^{20}$+7.27° (c 1.045, $CHCl_3$)
IR (film): 2962, 2107, 1748, 1434, 1372, 1216, 1033, 952 $cm^{-1}$
MS (m/z): 43 (100)
$^1$H-NMR (500 MHz, $CDCl_3$) 2.06 (3H, s), 2.07 (3H, s), 2.07 (3H, s), 2.10 (3H, s), 2.13 (3H, s), 3.47 (1H, dd, J=13.5 Hz, J=5.3 Hz), 3.54 (1H, dd, J=13.5 Hz, J=3.9 Hz), 4.12 (1H, dd, J=12.5 Hz, J=5.0 Hz), 4.23 (1H, dd, J=12.5 Hz, J=3.2 Hz), 5.03-5.11 (2H, m), 5.34 (1H, dd, J=7.7 Hz, J=3.5 Hz), 5.46 (1H, dd, J=7.2 Hz, J=3.5 Hz)
$^{13}$C-NMR (500 Hz, $CDCl_3$) 20.5 ($CH_3$), 20.8 ($CH_3$), 20.8 ($CH_3$), 50.6 ($CH_2$), 61.4 ($CH_2$), 68.4 (CH), 68.4 (CH), 68.6 (CH), 70.3 (CH), 169.8 (C), 169.9 (C), 170.0 (C), 170.6 (C)

EXAMPLE 2

Synthesis of TBDPS-ether (Molecule 1.3)

A solution of petaacetate (Molecule 1.2) (3.688 g, 8.84 mmol) in 75 ml of MeOH was treated with $K_2CO_3$ (0.305 g, 2.21 mmol) and stirred for 4 h at room temperature. After azeotropic removal of the solvent with $CH_3CN$ (3×40 ml) the residue was dissolved in 40 ml of dry pyridine and TBDPS-Cl (2.9 ml, 11.05 mmol) was added. After 33 h the reaction was worked up by azeotropic removal of the solvent with toluene (40 ml). Purification of the residue by column chromatography over silica gel (dichloromethane/methanol: 97/3) afforded Molecule 1.3 as a yellow oil (3.722 g, 8.35 mmol, 94%).

Formula: $C_{22}H_{31}N_3O_5Si$ (MM=445.6)
$R_f$: (dichloromethane/methanol: 97/3): 0.18
$\{\alpha\}_D^{20}$−8.48° (c 1.085, $CHCl_3$)
IR (film): 3414, 3069, 3036, 2931, 2891, 2847, 2104, 1474, 1462, 1428, 1390, 1276, 1113, 823, 740, 702, 614, 504 $cm^{-1}$
MS (m/z): 57 (100), 77 (68), 139 (41), 163 (94), 199 (75), 223 (14)
$^1$H-NMR (500 MHz, $CDCl_3$) 1.07 (9H, s), 2.96 (1H, br s), 3.25 (1H, br s), 3.34 (2H, br s), 3.41 (1H, dd, J=12.6 Hz, J=4.8 Hz), 3.47 (1H, dd, J=12.6 Hz, J=7.0 Hz), 3.74 (1H, m), 3.83 (4H, m), 3.93 (1H, m), 7.38-7.48 (6H, m), 7.66 (4H, m)
$^{13}$C-NMR (500 MHz, $CDCl_3$) 19.3 (C), 26.9 ($CH_3$), 53.6 ($CH_2$), 65.2 ($CH_2$), 69.8 (CH), 71.6 (CH), 72.9 (CH), 74.1 (CH), 128.0 (CH), 130.1 (CH), 132.6 (C), 135.6 (CH)

EXAMPLE 3

Synthesis of tetra-methyl ether (Molecule 1.4)

To a suspension of NaH (1.665 g, 65.84 mmol) in 20 ml of DMF was added a solution of Molecule 1.3 (3.668 g, 8.23 mmol) in 70 ml of DMF. This mixture was treated with 10 ml of MeI and stirred for 16 h at room temperature. The reaction was worked up by addition of $H_2O$ (1000 ml) and extraction with toluene (3×300 ml). The combined organics were washed once with brine (500 ml) and dried over MgSO$_4$. Column chromatography over silica gel (cyclohexane/ethyl acetate: 9/1) afforded Molecule 1.4 (FIG. 3) as a yellow oil (2.834 g, 5.65 mmol, 69%).

Formula: C$_{26}$H$_{39}$N$_3$O$_5$Si (MM=501.7)

R$_f$: (cyclohexane/ethyl acetate: 9/1): 0.19

IR (film): 3070, 2932, 2857, 2828, 2099, 1472, 1428, 1286, 1187, 1113, 824, 740, 703, 613 cm$^{-1}$ $^1$H-NMR (500 MHz, CDCl$_3$) 1.08 (9H, s), 3.27 (3H, s), 3.44 (3H, s), 3.48 (3H, s), 3.51 (3H, s), 3.27-3.62 (6H, m), 3.79 (1H, dd, J=11.4 Hz, J=4.1 Hz), 3.91 (1H, dd, J=11.4 Hz, J=2.8 Hz), 7.35-7.45 (6H, m), 7.71 (4H, m)

EXAMPLE 4

Synthesis of Primary Alcohol (Molecule 1.5)

A solution of TBDPS ether (Molecule 1.4) (2.92 g, 5.65 mmol) in 50 ml of dry THF was treated with TBAF (IM in THF, 8.75 ml, 8.75 mmol). After 22 h the solvent was removed in vacuo and the residue was purified by column chromatography over silica gel (dichloromethane/methanol: 98/2). An alcohol (Molecule 1.5; FIG. 3) was obtained as a slightly yellow oil (1.149 g, 4.36 mmol, 77%).

Formula: C$_{10}$H$_2$N$_3$O$_5$ (MM=263.3)

R$_f$: (dichloromethane/methanol: 98/2): 0.21

$^1$H-NMR (500 MHz, CDCl$_3$) 3.42 (3H, s), 3.48 (3H, s), 3.51 (3H, s), 3.52 (3H, s), 3.35-3.72 (8H, m)

EXAMPLE 5

Synthesis of allyl ether (Molecule 1.6)

To a suspension of NaH (0.22 g, 8.74 mmol) in 5 ml of DMF was added a solution of Molecule 1.5 (1.15 g, 4.37 mmol) in 15 ml of DMF. This mixture was treated with allyl bromide (0.756 ml, 8.74 mmol) and stirred for 4 h at room temperature. The reaction was worked up by addition of H$_2$O (200 ml) followed by extraction with toluene (3×100 ml). The combined organics were washed once with brine (100 ml) and dried over MgSO$_4$. Column chromatography over silica gel (cyclohexane/ethyl acetate: 8/2) afforded Molecule 1.6 (FIG. 3) as a slightly yellow oil (1.26 g, 4.15 mmol, 95%).

Formula: C$_{13}$H$_{25}$N$_3$O$_5$ (MM=303.4)

R$_f$: (cyclohexane/ethyl acetate: 8/2): 0.22

$^1$H-NMR (500 MHz, CDCl$_3$) 3.44 (3H, s), 3.45 (3H, s), 3.52 (6H, s), 3.35-3.55 (6H, m), 3.61 (1H, m), 3.77 (1H, dd, J=10.6 Hz, J=2.9 Hz), 4.04 (2H, dd, J=1.2 Hz, J=5.7 Hz), 5.19 (1H, br d, J=10.4 Hz), 5.29 (1H, br d, J=17.2 Hz), 5.93 (1H, ddt, J=5.7 Hz, J=10.4 Hz, J=17.2 Hz)

EXAMPLE 6

Synthesis of amine (Molecule 1.7)

A solution of azide (Molecule 1.6) (1.26 g, 4.15 mmol) in 25 ml of dry THF was treated with Ph$_3$P (1.635 g, 6.23 mmol) and stirred for 24 h at room temperature. After addition of 2.5 ml of H$_2$O stirring was continued for another 15 h. Then, the solvent was removed in vacuo and the residue was purified by column chromatography over silica gel (dichloromethane/methanol: 9/1). An amine (Molecule 1.7; FIG. 3) was obtained as a yellow oil (1.002 g, 3.61 mmol, 87%).

Formula: C$_{13}$H$_{27}$NO$_5$ (MM=277.4)

R$_f$: (dichloromethane/methanol: 9/1): 0.25

ESMS (m/z): 278 {M+H}$^+$ $^1$H-NMR (500 MHz, CDCl$_3$) 2.75 (1H, br dd, J=13.1 Hz, J=7.2 Hz), 2.93 (1H, br d, J=13.1 Hz), 3.43 (3H, s), 3.45 (3H, s), 3.52 (3H, s), 3.53 (3H, s), 3.35-3.60 (7H, m), 3.74 (1H, m), 4.03 (2H, br d, J=5.7 Hz), 5.18 (1H, br d, J=10.4 Hz), 5.28 (1H, br d, J=16.7 Hz), 5.92 (1H, ddt, J=5.7 Hz, J=10.4 Hz, J=16.7 Hz)

$^{13}$C-NMR (500 MHz, CDCl$_3$) 42.4 (CH$_2$), 57.5 (CH$_3$), 59.3 (CH$_3$), 60.3 (CH$_3$), 60.7 (CH$_3$), 67.5 (CH$_2$), 72.4 (CH$_2$), 79.3 (CH), 79.9 (CH), 81.2 (CH), 83.5 (CH), 117.2 (CH$_2$), 134.8 (CH)

EXAMPLE 7

Synthesis of diol (Molecule 2.1)

Figure 4:
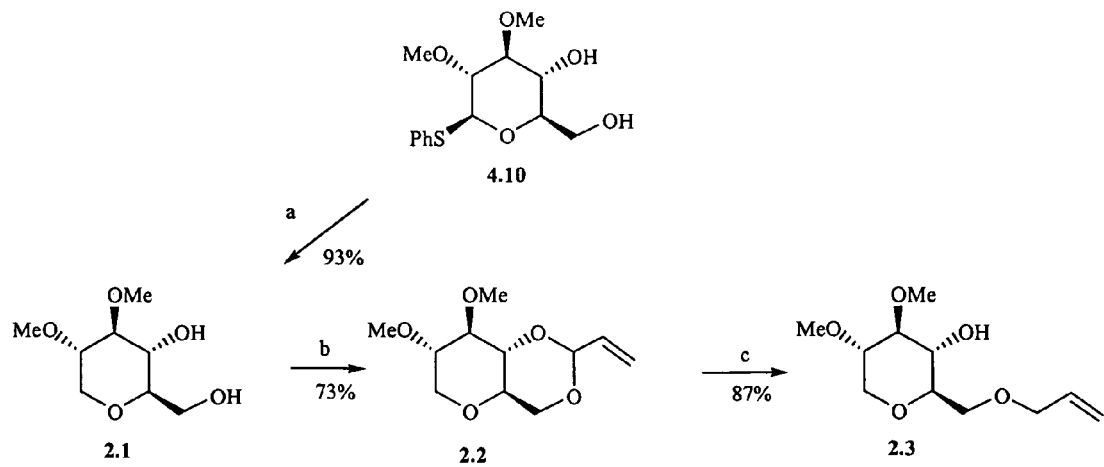
FIG. 4 is a diagrammatical representation of the synthesis scheme of scaffold Molecule 2.3 of the present invention.

Diol (Molecule 4.10 of FIG. 4) (6.191 g, 20.61 mmol) was added to a suspension of freshly prepared Raney Nickel W4 (50 g) in 400 ml of absolute EtOH. After stirring for 1 h at room temperature the reaction mixture was filtered through celite and washed several times with denaturated EtOH. The filtrate was concentrated in vacuo and purification of the residue by column chromatography over silica gel (ethyl acetate) afforded Molecule 2.1 (FIG. 4) as a white crystalline solid (3.696 g, 19.23 mmol, 93%).

Formula: C$_8$H$_{16}$O$_5$ (MM=192.2)

R$_f$: (ethyl acetate): 0.18

$^1$H-NMR (500 MHz, CDCl$_3$) 3.00-3.20 (3H, m), 3.25 (2H, m), 3.46 (3H, s), 3.45 (2H, m), 3.65 (3H, s), 3.74 (1H, m), 3.84 (1H, m), 4.08 (1H, dd, J=11.1 Hz, J=5.0 Hz)

EXAMPLE 8

Synthesis of acrolein acetal (Molecule 2.2)

A solution of diol (Molecule 2.1) (1.5 g, 7.8 mmol) in 7.5 ml of dry DMF was treated with acrolein dimethyl acetal (4.62 ml, 39 mmol) and PTSA.H$_2$O (0.371 g, 1.95 mmol). After stirring for 24 h at room temperature the reaction was stopped by addition of 1 ml of Et$_3$N and poured out in 200 ml of H$_2$O. The aqueous phase was extracted with toluene (3×100 ml) and the combined organics were washed once with brine (100 ml) and dried over MgSO$_4$. Column chromatography of the residue over silica gel (cyclohexane/ethyl acetate: 85/15) afforded Molecule 2.2 (FIG. 4) as white crystals (1.306 g, 5.67 mmol, 73%).

Formula: C$_{11}$H$_{18}$O$_5$ (MM=230.3)

R$_f$: (cyclohexane/ethyl acetate: 85/15): 0.16 mp=35° C.

$\{\alpha\}_D^{20}$+23.18° (c 1.005, CHCl$_3$)

IR (film): 3089, 2977, 2933, 2871, 2822, 1464, 1441, 1424, 1382, 1323, 1282, 1262, 1232, 1168, 1144, 1107, 1045, 1028, 1002, 942, 912 cm$^{-1}$ MS (m/z): 55 (83), 71 (100), 85 (38), 101 (31)

$^1$H-NMR (500 MHz, CDCl$_3$) 3.22 (2H, m), 3.31 (3H, m), 3.49 (3H, s), 3.50 (1H, t, J=10.2 Hz), 3.63 (3H, s), 4.06 (1H, dd, J=11.1 Hz, J=4.9 Hz), 4.18 (1H, dd, J=4.9 Hz, J=10.4 Hz), 4.97 (1H, d, J=4.1 Hz), 5.32 (1H, d, J=10.8 Hz), 5.48 (1H, d, J=17.4 Hz), 5.86 (1H, ddd, J=4.1 Hz, J=10.8 Hz, J=17.4 Hz)

$^{13}$C-NMR (500 MHz, CDCl$_3$) 59.2 (CH$_3$), 60.9 (CH$_3$), 68.5 (CH$_2$), 68.5 (CH$_2$), 71.3 (CH), 79.6 (CH), 81.5 (CH), 83.8 (CH), 100.5 (CH), 119.0 (CH$_2$), 133.7 (CH)

EXAMPLE 9

Synthesis of Alcohol (Molecule 2.3)

NaCNBH$_3$ (0.308 g, 4.88 mmol) and molecular sieves 3 Å (0.15 g) were added to a solution of acrolein acetal 2.2 (0.154 g, 0.67 mmol) in 6 ml of dry THF. This mixture was treated dropwise with TfOH (0.438 ml, 4.94 mmol) and stirred for 1 h at room temperature. After addition of 50 ml of $H_2O$ the aqueous phase was extracted with $CH_2Cl_2$ (3×50 ml). The combined organics were dried over $MgSO_4$ and the residue was purified by column chromatography over silica gel (cyclohexane/ethyl acetate: 1/1). Alcohol Molecule 2.3 (FIG. 4) was obtained as a colorless oil (0.134 g, 0.58 mmol, 87%).

Formula: $C_{11}H_{20}O_5$ (MM=232.3)

$R_f$: (cyclohexane/ethyl acetate: 1/1): 0.20

$\{\alpha\}_D^{20}$ +26.91°(c 1.085, $CHCl_3$)

IR (film): 3442, 2932, 2903, 2858, 1644, 1463, 1324, 1262, 1218, 1185, 1157, 1129, 1098, 996, 957, 928 $cm^{-1}$ MS (m/z): 41 (100), 58 (31), 74 (19), 101 (8)

$^1$H-NMR (500 MHz, $CDCl_3$) 2.92 (1H, br d, J=2.3 Hz), 3.08 (1H, t, J=8.8 Hz), 3.12 (1H, t, J=11.1 Hz), 3.27 (1H, m), 3.33 (1H, m), 3.43 (3H, s), 3.43 (1H, m), 3.60 (1H, dd, J=5.5 Hz, J=10.4 Hz), 3.63 (3H, s), 3.67 (1H, dd, J=3.2 Hz, J=10.4 Hz), 4.02 (1H, m), 4.07 (1H, dd, J=5.1 Hz, J=11.2 Hz), 5.17 (1H, d, J=10.4 Hz), 5.25 (1H, d, J=17.2 Hz), 5.88 (1H, ddt, J=5.7 Hz, J=10.4 Hz, J=17.2 Hz)

$^{13}$C-NMR (500 MHz, $CDCl_3$) 58.4 ($CH_3$), 60.8 ($CH_3$), 67.6 ($CH_2$), 70.1 ($CH_2$), 70.8 (CH), 72.7 ($CH_2$), 78.7 (CH), 79.8 (CH), 87.0 (CH), 117.6 ($CH_2$), 134.4 (CH)

EXAMPLE 10

Figure 5:
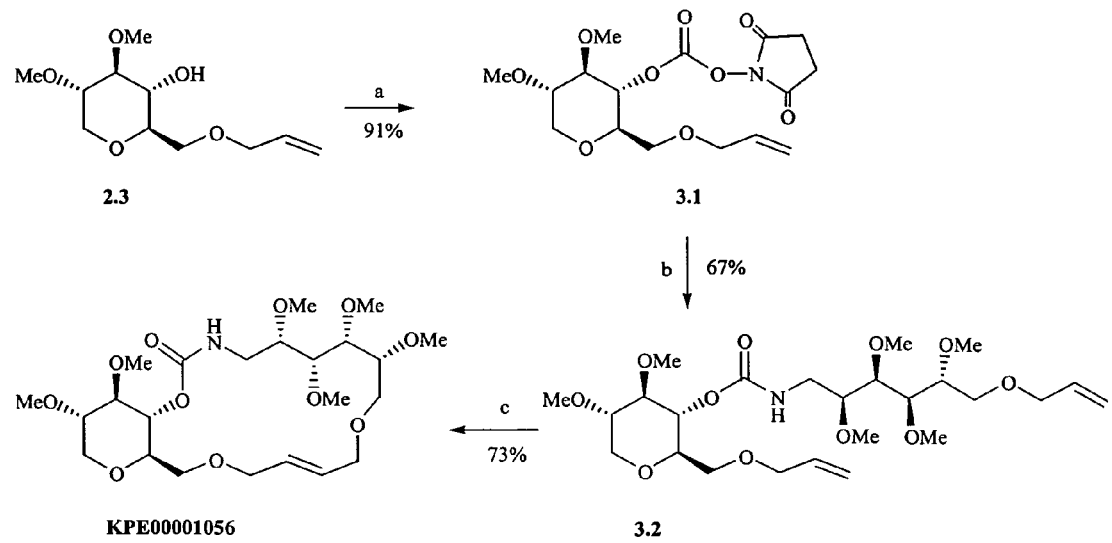
FIG. 5 is a diagrammatical representation of the synthesis scheme of macrolide KPE00001056 of the present invention.

Synthesis of Activated succinimidylcarbonate (Molecule 3.1—FIG. 5)

A solution of alcohol (Molecule 2.3) (0.794 g, 3.42 mmol) in 16 ml of dry DMF was treated with DMAP (0.42 g, 3.42 mmol) and N,N'-disuccinimidylcarbonate (2.63 g, 10.26 mmol). After stirring for 29 h at room temperature the reaction mixture was poured out in toluene (300 ml) and the organic phase was washed with $H_2O$ (3×100 ml) and brine (100 ml). The organics were dried over $MgSO_4$ and after removal of the solvent the residue was dissolved in EtOAc. The precipitate was filtered off and the filtrate was concentrated in vacuo. Column chromatography of the residue over silica gel (ether) afforded succinimidylcarbonate (Molecule 3.1; FIG. 5) (1.156 g, 3.1 mmol, 91%).

Formula: $C_{16}H_{23}NO_9$ (MM=373.4)

$R_f$: (ether): 0.35 mp=97° C.

$\{\alpha\}_D^{20}$ +38.27° (c 0.580, $CHCl_3$)

IR (film): 2940, 2873, 1817, 1791, 1744, 1462, 1430, 1370, 1259, 1233, 1204, 1159, 1098, 1012, 993, 972, 940 $cm^{-1}$ $^1$H-NMR (500 MHz, $CDCl_3$) 2.83 (4H, s), 3.15 (1H, dd, J=10.2 Hz, J=11.2 Hz), 3.30-3.38 (2H, m), 3.47 (3H, s), 3.49 (2H, m), 3.61 (1H, m), 3.62 (3H, s), 3.97 (1H, dd, J=5.9 Hz, J=12.7 Hz), 4.02 (1H, dd, J=5.9 Hz, J=12.7 Hz), 4.10 (1H, dd, J=5.0 Hz, J=11.3 Hz), 4.81 (1H, t, J=9.3 Hz), 5.19 (1H, d, J=10.3 Hz), 5.26 (1H, d, J=17.2 Hz), 5.87 (1H, ddt, J=5.9 Hz, J=10.3 Hz, J=17.2 Hz)

$^{13}$C-NMR (500 MHz, $CDCl_3$) 25.5 ($CH_2$), 59.1 ($CH_3$), 61.2 ($CH_3$), 67.9 ($CH_2$), 68.1 ($CH_2$), 72.8 ($CH_2$), 77.1 (CH), 78.0 (CH), 79.6 (CH), 85.1 (CH), 118.1 ($CH_2$), 134.2 (CH), 151.2 (C), 168.5 (C)

EXAMPLE 11

Synthesis of diene (Molecule 3.2)

A solution of succinimidylcarbonate (Molecule 3.1) (1.062 g, 2.84 mmol) in 10 ml of dry THF was treated with a solution of amine (Molecule 1.7) (0.789 g, 2.84 mmol) in 15 ml of THF. After stirring for 16 h at room temperature the reaction mixture was concentrated in vacuo and the residue was purified by column chromatography over silica gel (dichloromethane/methanol: 97.5/2.5) to yield a diene (Molecule 3.2; FIG. 5)) as a slightly yellow oil (1.02 g, 1.9 mmol, 67%).

Formula: $C_{25}H_{45}NO_{11}$ (MM=535.6)

$R_f$: (dichloromethane/methanol: 97.5/2.5): 0.18

$\{\alpha\}_D^{20}$ −6.76° (c 1.025, $CHCl_3$)

IR (film): 3347, 3083, 2933, 2828, 1728, 1647, 1531, 1464, 1375, 1347, 1248, 1192, 1099, 1019, 925 $cm^{-1}$ $^1$H-NMR (500 MHz, $CDCl_3$) 3.12 (2H, m), 3.20 (1H, t, J=9.1 Hz), 3.32 (1H, m), 3.42 (3H, s), 3.47 (6H, s), 3.48 (3H, s), 3.52 (3H, s), 3.54 (3H, s), 3.37-3.58 (8H, m), 3.65 (1H, m), 3.76 (1H, dd, J=2.7 Hz, J=10.6 Hz), 3.99 (1H, m), 4.02 (2H, br d, J=5.7 Hz), 4.09 (1H, dd, J=5.2 Hz, J=11.3 Hz), 4.63 (1H, m), 5.13-5.32 (5H, m), 5.90 (2H, m)

$^{13}$C-NMR (500 MHz, $CDCl_3$) 41.8 ($CH_2$), 57.5 ($CH_3$), 58.0 ($CH_3$), 59.2 ($CH_3$), 60.2 ($CH_3$), 60.3 ($CH_3$), 60.5 ($CH_3$), 67.4 ($CH_2$), 67.6 ($CH_2$), 69.8 ($CH_2$), 71.7 (CH), 72.2 ($CH_2$), 72.6 ($CH_2$), 78.3 (CH), 79.0 (CH), 79.4 (CH), 79.8 (CH), 81.5 (CH), 85.4 (CH), 117.3 ($CH_2$), 117.6 ($CH_2$), 134.5 (CH), 134.7 (CH), 155.7 (C)

EXAMPLE 12

Synthesis of macrolide KPE00001056

To 165 ml of dry and degassed $CH_2Cl_2$ were added dropwise and simultaneously a solution of diene (Molecule 3.2) (0.95 g, 1.77 mmol) in 95 ml of $CH_2Cl_2$ and a solution of the Grubb's catalyst (0.15 g, 0.18 mmol) in 95 ml of $CH_2Cl_2$. After stirring 21 h at room temperature a fresh solution of the catalyst (0.075 g, 0.09 mmol) in 50 ml of $CH_2Cl_2$ was added and stirring was continued for another 23 h. Then the reaction mixture was concentrated in vacuo and the residue was purified by column chromatography over silica gel (cyclohexane/acetone: 7/3) to afford macrolide KPE00001056 (FIG. 5) (0.662 g, 1.3 mmol, 73%).

Formula: $C_{23}H_{41}NO_{11}$ (MM=507.6)

$R_f$: (cyclohexane/acetone: 7/3): 0.18

$\{\alpha\}_D^{20}$ +46.78° (c 1.135, $CHCl_3$)

IR (film): 3344, 2933, 2833, 1720, 1527, 1459, 1374, 1256, 1189, 1098, 978 $cm^{-1}$ ESMS (m/z): 508 $\{M+H\}^+$, 530 $\{M+Na\}^+$ $^1$H-NMR (500 MHz, $CDCl_3$) 3.13 (1H, t, J=10.9 Hz), 3.18 (1H, t, J=9.0 Hz), 3.18 (1H, m), 3.35 (5H, m), 3.44 (3H, s), 3.45 (3H, s), 3.47 (3H, s), 3.53 (3H, s), 3.54 (3H, s), 3.56 (3H, s), 3.43-3.58 (3H, m), 3.68 (1H, dd, J=5.2 Hz, J=10.0 Hz), 3.75 (1H, ddd, J=3.5 Hz, J=8.2 Hz, J=12.8 Hz), 3.79 (1H, dd, J=2.8 Hz, 6.5 Hz), 3.92 (2H, m), 4.05 (1H, m), 4.12 (2H, m), 4.64 (1H, t, J=9.5 Hz), 4.83 (1H, dd, J=3.8 Hz, J=8.0 Hz), 5.69 (2H, m)

$^{13}$C-NMR (500 MHz, $CDCl_3$) 39.3 ($CH_2$), 57.6 ($CH_3$), 57.8 ($CH_3$), 58.9 ($CH_3$), 60.2 ($CH_3$), 60.5 ($CH_3$), 60.6 ($CH_3$), 67.8 ($CH_2$), 68.4 ($CH_2$), 68.4 ($CH_2$), 70.6 ($CH_2$), 71.5 ($CH_2$), 71.6 (CH), 77.7 (CH), 79.3 (CH), 79.5 (CH), 80.0 (CH), 80.3 (CH), 81.2 (CH), 85.2 (CH), 128.7 (CH), 130.5 (CH), 155.8 (C)

$^1$H-NMR (500 MHz, $C_6D_6$) 3.07 (6H, s), 3.24 (3H, s), 3.44 (3H, s), 3.50 (3H, s), 3.54 (3H, s), 3.03-4.05 (19H, m), 4.73 (1H, dd, J=3.8 Hz, J=8.0 Hz), 5.17 (1H, t, J=9.5 Hz), 5.57 (1H, dt, J=15.6 Hz, J=5.0 Hz), 5.64 (1H, dt, J=15.6 Hz, J=5.4 Hz)

EXAMPLE 13

Figure 6:
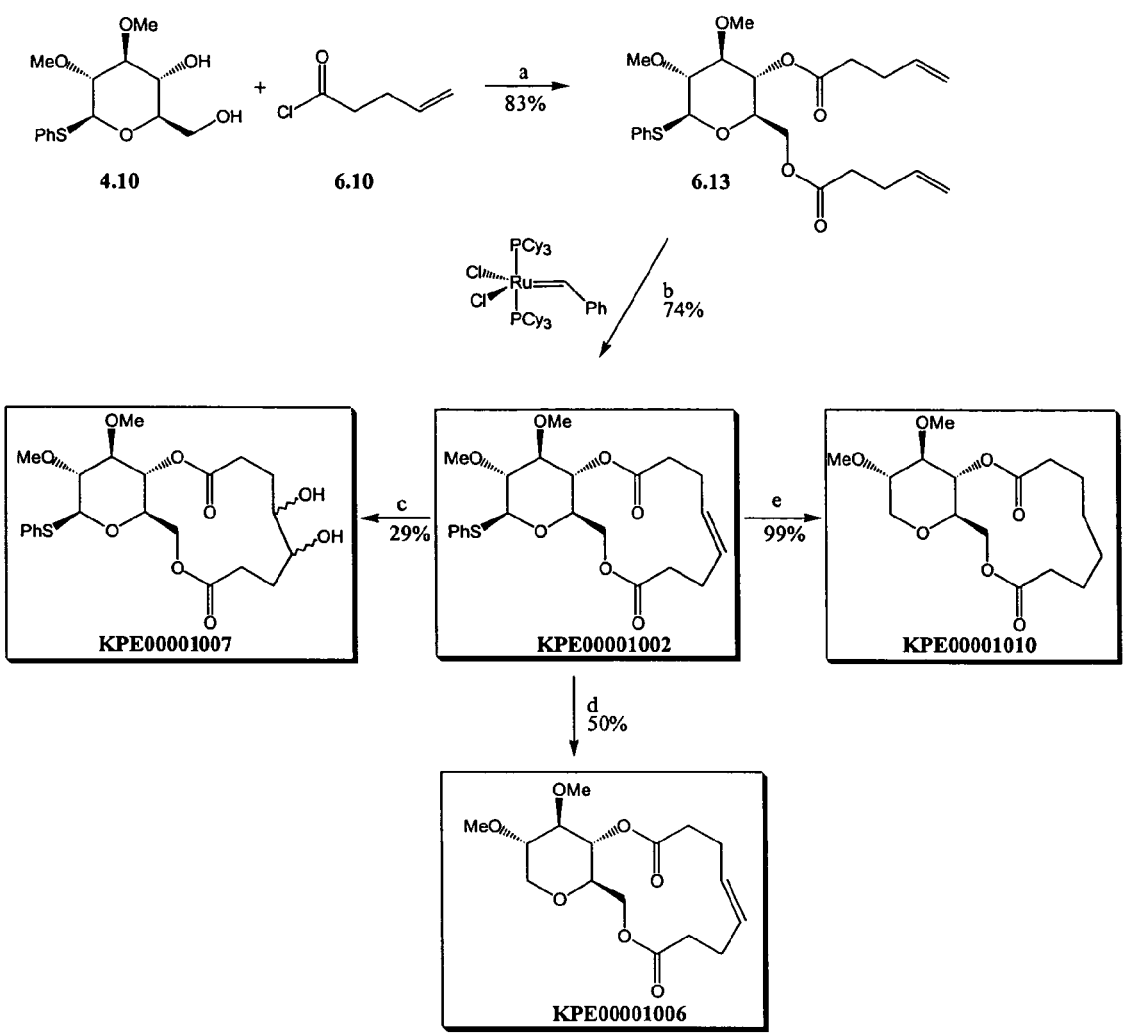
FIG. 6 is a diagrammatical representation of the synthesis scheme of macrolides KPE00001007, KPE00001002, KPE00001010 and KPE00001006 of the present invention.

Synthesis of the diester (Molecule 6.13; FIG. 6)

To a solution of diol (Molecule 4.10) (6.58 g, 21.910 mmol) in methylene chloride (220 ml) were added at room temperature pyridine (7.1 ml, 87.620 mmol), dimethylaminopyridine (20 mg) and 4-pentenoyl chloride (Molecule 6.10) (7.8 g, 65.720 mmol). The solution was stirred at room temperature for 18 hours. The mixture was then diluted with methylene chloride (280 ml), washed with a saturated sodium bicarbonate solution (3×500 ml) and brine (2×500 ml). The organic layer was dried ($MgSO_4$), filtered and the solvent was removed under reduced pressure. The crude product was purified by flash chromatography (eluent: cyclohexane/ethyl acetate 95/5) to yield a white solid (Molecule 6.13) (8.5 g, 83%).

Formula: $C_{24}H_{32}O_7S$
Molecular weight: 464.57
$R_f$: 0.60 (cyclohexane/ethyl acetate 1:1)
$[\alpha]_D^{20}$=−323.8, $[\alpha]_{365}^{20}$=−489.1 (c=0.34 in chloroform)
IR(KBr): 3396, 2934, 1743, 1642, 1584, 1480, 1440, 1369, 1241, 1153, 1067, 1041, 917, 821, 746, 692 $cm^{-1}$
ES-MS: 487=$[464+Na]^+$
$^1$H-NMR (500 MHz, $CDCl_3$): 7.55 (2H, m), 7.29 (3H, m), 5.84 (1H, m), 5.80 (1H, m), 5.08 (2H, m), 5.04 (2H, m), 4.91 (1H, dd, app. t, J=9.8 Hz), 4.51 (1H, d, J=9.6 Hz), 4.45 (2H, m), 4.43 (2H, m), 4.15 (2H, m), 3.60 (3H, s), 3.56 (1H, m), 3.53 (3H, s), 3.30 (1H, dd, app. t, J=9.7 Hz), 3.14 (1H, dd, app. t, J=9.7 Hz), 2.38 (2H, m), 2.36 (2H, m)
$^{13}$C-NMR (125 MHz, $CDCl_3$): 172.51, 171.54, 136.16, 132.96, 132.20, 128.74, 127.68, 115.72, 115.42, 87.13, 85.66, 81.93, 77.16, 75.74, 69.40, 62.53, 60.78, 33.33, 33.17, 28.57, 28.53
C,H-analysis: calculated: C 62.00%, H 6.90%
found: C 62.10%, H 7.21%

EXAMPLE 14

Synthesis of KPE00001002 via Metathesis Reaction

To methylene chloride (90 ml) were added slowly and simultaneously a solution of diene (Molecule 6.13) (700 mg, 1.500 mmol) in methylene chloride (90 ml) and a solution of the Grubbs' catalyst (150 mg, 0.18 mmol) in methylene chloride (270 ml). Addition took 6 hours and the mixture was then stirred for another 48 hours. The solvent was removed under reduced pressure. The crude product was purified by flash chromatography (gradient elution: cyclohexane/ethyl acetate 95/5 to 9:1), followed by recrystallization from diethylether and cyclohexane to yield KPE00001002 (FIG. 6) as a white solid (485 mg, 74%).

Formula: $C_{22}H_{28}O_7S$
Molecular weight: 436.52
$R_f$: 0.21 (cyclohexane/ethyl acetate 8:2)
Melting point: 111-112° C.
$[\alpha]_D^{20}$=−44.3, $[\alpha]_{365}^{20}$=−176.5 (c=1.03 in chloroform)
IR(KBr): 3440, 2927, 2834, 2360, 1732, 1643, 1478, 1441, 1352, 1232, 1171, 1086, 1066, 1045, 966, 820, 748, 692 $cm^{-1}$
ES-MS: 459=$[436+Na]^+$
$^1$H-NMR (500 MHz, CDCl3): 7.52 (2H, m), 7.30 (3H, m), 5.53 (1H, ddd, J=15.0, 7.3 Hz), 5.35 (1H, ddd, J=14.6, 8.5, 5.0 Hz), 5.06 (1H, t, J=9.8 Hz), 4.52 (1H, d, J=7.7 Hz), 4.25 (1H, dd, J=9.7, 2.9 Hz), 4.09 (1H, dd, J=9.8, 2.7 Hz), 3.62 (3H, s), 3.58 (1H, ddd, J=10.0, 7.6, 2.7 Hz), 3.51 (3H, s), 3.27 (1H, dd, app. t, J=9.6 Hz), 3.19 (1H, dd, app. t, J=9.6 Hz), 2.47 (2H, m), 2.40 (2H, m), 2.31 (2H, m), 2.28 (2H, m)
$^{13}$C-NMR (125 MHz, CDCl3): 173.49, 170.88, 132.69, 132.30, 131.67, 128.92, 128.64, 127.77, 88.14, 86.07, 82.22, 75.32, 70.02, 63.72, 60.88, 60.55, 34.64, 33.64, 28.77, 26.64
C,H-analysis: calculated: C 60.50%, H 6.50%, S 7.30%
found: C 60.11%, H 6.66%, S 7.54%

EXAMPLE 15

Synthesis of KPE00001007 via Dihydroxylation

To a solution of N-methylmorfoline oxide (55 mg, 0.412 mmol) in tert-butanol (1 ml), acetone (1 ml) and water (0.4 ml) was added a solution of osmiumtetroxide (10 mg, 0.03 mmol) in tert-butanol (1 ml). To this mixture a solution of diene (KPE00001002) (100 mg, 0.23 mmol) in tert-butanol (2 ml) was added. The reaction mixture was stirred at room temperature for 1 hour. The mixture was then diluted with acetone (20 ml) and active carbon was added. The mixture was again stirred at room temperature for 1 hour, filtered over celite and the residue was washed with acetone (3×20 ml). The solvent was removed under reduced pressure. The crude product was purified by flash chromatography (gradient elution: methylene chloride/methanol 1/0 to 95/5), followed by HPLC (eluent: methylene chloride/methanol 85/15) to yield 12 mg (29%) of KPE00001007 (FIG. 6).

Formula: $C_{22}H_{30}O_9S$
Molecular weight: 470.53
$R_f$: 0.09 (cyclohexane/ethyl acetate 1:1)
Melting point: 138-139° C.
IR(KBr): 3345, 2934, 2362, 1732, 1440, 1383, 1211, 1148, 1091, 1074, 1002, 962, 917, 871, 821, 750, 691, 570 $cm^{-1}$
ES-MS: 493=$[470+Na]^+$, 509=$[470+K]^+$
$^1$H-NMR (500 MHz, CDCl3): 7.52 (2H, m), 7.31 (3H, m), 4.93 (1H, dd, J=9.6 Hz), 4.54 (1H, d, J=9.8 Hz), 4.28 (1H, m), 4.20 (1H, m), 3.65 (1H, m), 3.62 (3H, s), 3.54 (3H, s), 3.34 (1H, dd, app. t, J=8.8 Hz), 3.30 (1H, dd, app. t, J=9.3 Hz), 3.14 (1H, m), 2.60 (1H, m), 2.51 (2H, m), 2.46 (2H, m), 2.40 (1H, m), 2.04 (2H, m), 1.85 (1H, m)
$^{13}$C-NMR (125 MHz, CDCl3): 173.27, 172.99, 135.60, 132.46, 128.83, 127.89, 87.75, 85.47, 82.08, 74.37, 73.60, 72.04, 70.08, 66.04, 60.86, 60.79, 30.45, 30.15, 28.79, 27.93

EXAMPLE 16

Synthesis of KPE00001006 via Desulfurization

Raney-Nickel (2 g) was washed with absolute ethanol (4×10 ml) and added as a suspension in absolute ethanol (9 ml) to thioglycoside KPE00001002 (100 mg, 0.230 mmol). The mixture was stirred at room temperature for 1 hour. The catalyst was allowed to settle and the solution was decanted. The catalyst was washed with absolute ethanol (3×20 ml). The combined ethanol fractions were filtered over celite, the filter was washed with absolute ethanol (3×10 ml) and the solvent was removed under reduced pressure. The crude product was purified by flash chromatography (gradient elution: cyclohexane/ethyl acetate 1/0 to 1/1) to yield 38 mg (50%) of product KPE00001006 (FIG. 6).

Formula: $C_{16}H_{24}O_7$
Molecular weight: 328.36
$R_f$: 0.46 (cyclohexane/ethyl acetate 1:1)
Melting point: 99-100° C.
$[\alpha]_D^{20}$=+16.0; $[\alpha]_{365}^{20}$=+52.7 (c=0.30 in chloroform)
IR(KBr): 2924, 2358, 1745, 1435, 1338, 1233, 1172, 1093, 1048, 994, 864, 668, 620 $cm^{-1}$
ES-MS: 351=$[328+Na]^+$ ¹H-NMR (500 MHz, CDCl3): 5.56 (1H, m), 5.36 (1H, m), 5.04 (1H, dd, app. t, J=9.8 Hz), 4.26 (1H, dd, J=12.5, 2.8 Hz), 4.13 (1H, dd, J=11.3, 5.6 Hz), 4.06 (1H, dd, J=12.5, 2.6 Hz), 3.54 (1H, m), 3.52 (3H, s), 3.50 (3H, s), 3.46 (1H, m), 3.23 (1H, dd, app. t, J=9.3 Hz), 3.19 (1H, dd, app. t, J=11.0 Hz), 2.49 (2H, m), 2.37 (2H, m), 2.30 (2H, m), 2.15 (2H, m)

¹³C-NMR (125 MHz, CDCl3): 173.52, 170.89, 131.77, 128.94, 85.27, 79.34, 75.41, 70.10, 68.58, 63.85, 59.99, 59.01, 34.53, 33.53, 28.78, 26.68

C,H-analysis: calculated: C 58.53%, H 7.37%
found: C 58.80%, H 7.48%

EXAMPLE 17

Synthesis of KPE00001010 via Desulfurization and Reduction Double Bond

Raney-Nickel (6 g) was washed with absolute ethanol (3×20 ml) and added as a suspension in absolute ethanol (30 ml) to thioglycoside (KPE00001002) (100 mg, 0.230 mmol). The mixture was stirred at room temperature under hydrogen atmosphere (balloon) for 1 hour. The mixture was filtered over celite and the residue was washed with absolute ethanol (5×15 ml). A concentrated HCl solution (5 drops) was added and the solvent was removed under reduced pressure to yield 75 mg (99%) of product KPE00001010 (FIG. 6).

Formula: $C_{16}H_{26}O_7$
Molecular weight: 330.38
$R_f$: 0.48 (cyclohexane/ethyl acetate 1:1)
Melting point: 36-37° C.
$[\alpha]_D^{20}$=−40.4; $[\alpha]_{365}^{20}$32 −33.1 (c=0.90 in chloroform)
IR(KBr): 3452, 2934, 2360, 1739, 1463, 1354, 1209, 1140, 1103, 1036, 954, 591 cm$^{-1}$
ES-MS: 331=[330+H]$^+$, 353=[330+Na]$^+$ ¹H-NMR (500 MHz, CDCl3): 4.91 (1H, dd, app. t, J=9.5 Hz), 4.19 (1H, dd, J=11.7, 2.2 Hz), 4.09 (1H, ddd, J=11.2, 11.0, 4.1 Hz), 4.08 (1H, dd, J=11.8, 2.2 Hz), 3.56 (1H, m), 3.52 (3H, s), 3.48 (3H, s), 3.35 (1H, m), 3.25 (1H, dd, app. t, J=9.2 Hz), 3.16 (1H, dd, app. t, J=11.1 Hz), 2.40 (2H, m), 2.32 (2H, m), 1.72 (2H, m), 1.64 (2H, m), 1.36 (2H, m), 1.34 (2H, m)

¹³C-NMR (125 MHz, CDCl3): 173.59, 172.64, 84.77, 79.19, 75.35, 73.54, 67.93, 66.25, 60.29, 58.20, 33.89, 33.47, 26.58, 26.31, 23.86, 22.93

C,H-analysis: calculated: C 58.20%, H 7.90%
found: C 56.52%, H 8.26%

EXAMPLE 18

Synthesis of Molecule 7.3 by Means of Coupling of Sidechains

Figure 7:
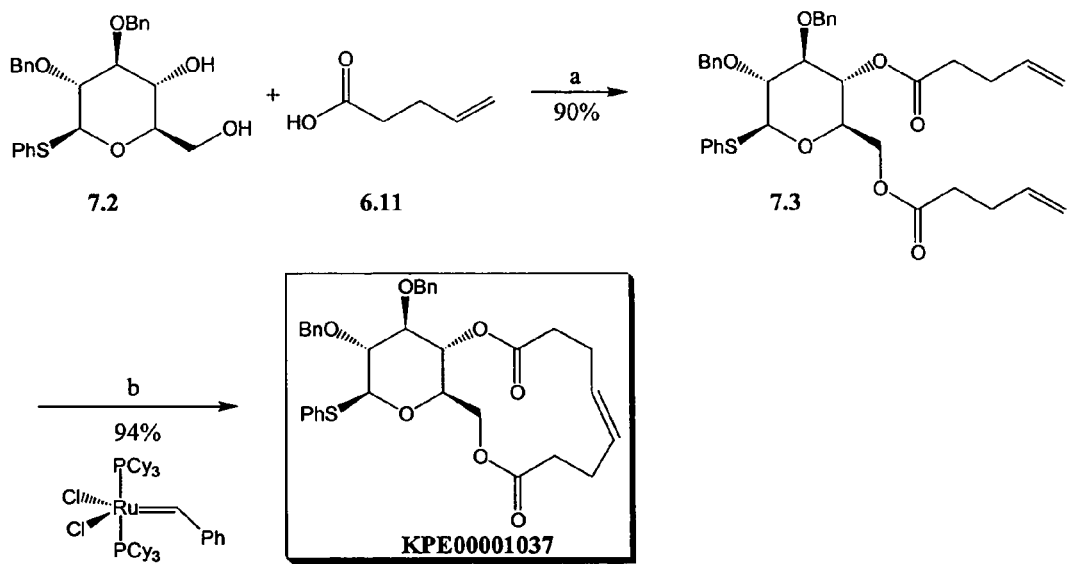
FIG. 7 is a diagrammatical representation of the synthesis scheme of macrolide KPE00001037 of the present invention.

To a solution of 4-pentenoic acid (Molecule 6.11) (0.07 ml, 0.66 mmol) in dry methylene chloride (5 ml) were added diisopropyl carbodiimide (0.105 ml, 0.66 mmol), hydroxybenzotriazole (90 mg, 0.66 mmol) and dimethylaminopyridine (10 mg). The mixture was stirred at room temperature for 1 hour and then diol (Molecule 7.2) (0.1 g, 0.22 mmol) was added. The mixture was stirred at room temperature for 120 hours. The reaction mixture was diluted with methylene chloride (45 ml), washed with a saturated sodium bicarbonate solution (3×50 ml) and brine (2×50 ml). The organic layer was dried (MgSO$_4$), filtered and the solvent was removed under reduced pressure. The crude product was purified by flash chromatography (gradient elution: cyclohexane/ethyl acetate 1/0 tot 7/3) to yield a white solid (Molecule 7.3; FIG. 7) (122 mg, 90%).

Formula: $C_{36}H_{40}O_7S$
Molecular weight: 616.77
$R_f$: 0.66 (cyclohexane/ethyl acetate 1:1)
$[\alpha]_D^{20}$=+99.0; $[\alpha]_{365}^{20}$=+69.8 (c=0.48 in chloroform)
IR(KBr): 3064, 2918, 2361, 1744, 1641, 1497, 1454, 1358, 1163, 1046, 915, 744, 698 cm$^{-1}$
ES-MS: 634=[616+NH$_4$]$^+$ ¹H-NMR (500 MHz, CDCl3): 7.58 (2H, m), 7.39 (2H, m), 7.35 (2H, m), 7.30 (3H, m), 7.26 (3H, m), 7.24 (3H, m), 5.82 (1H, m), 5.76 (1H, m), 5.07 (1H,), 5.05 (1H, dd, J=12.1, 2.3 Hz), 5.03 (1H, s), 5.00 (1H, s), 4.97 (1H, m), 4.89 (1H, m), 4.82 (1H, m), 4.71 (1H, m), 4.67 (1H, dd, app. t, J=9.1 Hz), 4.63 (1H, dd, J=14.3, 8.8 Hz), 4.17 (1H, m), 4.16 (1H, m), 3.68 (1H, dd, J=9.0, Hz), 3.60 (1H, m), 3.57 (1H,), 2.44 (2H, m), 2.39 (2H, m), 2.29 (2H, m), 2.22 (2H, m)

¹³C-NMR (125 MHz, CDCl3): 172.50, 171.48, 137.86, 137.62, 136.46, 136.16, 133.09, 132.14, 128.81, 128.33, 128.30, 128.17, 127.87, 127.70, 127.66, 127.58, 115.65, 115.42, 87.44, 83.74, 80.45, 75.88, 75.42, 75.32, 69.50, 62.50, 33.15, 33.10, 28.52, 28.37

C,H-analysis: calculated: C 70.11%, H 6.54%, S 5.20%
found: C 69.56%, H 6.34%, S 5.42%

EXAMPLE 19

Synthesis of KPE00001037 via Metathesis Reaction

To methylene chloride (4 ml) were added slowly and simultaneously a solution of diene (Molecule 7.3) (55 mg, 0.09 mmol) in methylene chloride (4 ml) and a solution of the Grubbs' catalyst (7.5 mg, 0.009 mmol) in methylene chloride (4 ml). The reaction mixture was stirred at room temperature for 95 hours. The solvent was removed under reduced pressure. The crude product was purified by flash chromatography (gradient elution: cyclohexane/ethyl acetate 1/0 to 9/1), followed by HPLC (eluent: cyclohexane/ethyl acetate 9/1) to yield 37 mg (70%) of KPE00001037 (FIG. 7).

Formula: $C_{34}H_{36}O_7S$
Molecular weight: 588.71
$R_f$: 0.17 (cyclohexane/ethyl acetate 9:1)
Melting point: 137-138° C.
$[\alpha]_D^{20}$=+165.1; $[\alpha]_{365}^{20}$=+109.4 (c=0.33 in chloroform)
IR(KBr): 2924, 1737, 1440, 1384, 1234, 1189, 1136, 1047, 918, 742, 698 cm$^{-1}$
ES-MS: 606=[588+NH$_4$]$^+$ ¹H-NMR (500 MHz, CDCl3): 7.53 (2H, m), 7.36 (3H, m), 7.33 (3H, m), 7.31 (3H, m), 7.29 (2H, m), 7.23 (2H, m), 5.53 (1H, ddd, J=14.0, 7.5 Hz), 5.32 (1H, ddd, J=14.8, 9.7, 5.9 Hz), 5.17 (1H, dd, app. t, J=9.8 Hz), 4.88 (1H, d, J=10.2Hz), 4.77 (1H, d, J=11.4 Hz), 4.71 (1H, d, J=10.2 H), 4.66 (1H, d, J=9.6 Hz), 4.62(1H, d, J=11.4 Hz), 4.23 (1H, dd, J=12.5, 2.8 Hz), 4.12 (1H, dd, J=12.5, 3.0 Hz), 3.63 (1H, dd, app. t, J=8.6 Hz), 3.60 (1H, m), 3.57 (1H, dd, app. t, J=8.6 Hz), 2.37 (2H, m), 2.28 (2H, m), 2.16 (2H, m), 2.08 (1H, m)

¹³C-NMR (125 MHz, CDCl3): 173.45, 170.80, 137.82, 137.57, 132.95, 132.20, 131.56, 128.88, 128.85, 128.26, 128.20, 128.15, 127.79, 127.75, 127.66, 127.54, 88.39, 83.84, 80.82, 75.49, 75.40, 75.09, 70.11, 63.76, 34.61, 33.56, 28.70, 26.55

C,H-analysis: calculated: C 69.40%, H 6.20%, S 5.40%
found: C 68.89%, H 6.26%, S 5.36%

EXAMPLE 20

Synthesis of the diester (Molecule 7.45)

To a solution of 6-heptenoic acid (Molecule 7.44) (5.0 ml, 36.90 mmol) in dry methylene chloride (80 ml) were added at 0° C. 1,3-diisopropylcarbodiimide (8.6 ml, 55.36 mmol), 1-hydroxybenzotriazole (7.48 g, 55.36 mmol) and 4-dimethylaminopyridine (565 mg, 4.62 mmol). The solution was stirred at room temperature for 2 hours. A solution of the diol (Molecule 4.10) (2.78 g, 9.23 mmol) in a mixture of methylene chloride (40 ml) and dimethylformamide (10 ml) was added at 0° C. The mixture was then stirred at room temperature for 72 hours. The mixture was then diluted with methylene chloride (80 ml), washed with a 1M HCl solution (3×200 ml), a saturated sodium bicarbonate solution (3×200 ml) and brine (2×200 ml). The organic layer was dried (MgSO$_4$), filtered and the solvent was removed under reduced pressure. The crude product (Molecule 7.45) was purified by flash chromatography (gradient elution: cyclohexane/ethyl acetate 1/0 to 7/3) to yield Molecule 7.45 (FIG. 9) as a white solid (1.26 g, 54%). 129 mg (3%) of the monoester was obtained as well.

Diester Molecule 7.45:
Formula: $C_{28}H_{40}O_7S$
Molecular weight: 520.68
R$_f$: 0.66 (cyclohexane/ethyl acetate 1:1)
$[\alpha]_D^{20}=-11.5$; $[\alpha]_{365}^{20}=-71.8$ (c=0.96 in chloroform)
IR(KBr): 3075, 2932, 1816, 1743, 1640, 1584, 1480, 1440, 1376, 1282, 1234, 1152, 1067, 1041, 995, 954, 908, 820, 744, 692 cm$^{-1}$
ES-MS: 543=[520+Na]$^+$
$^1$H-NMR (500 MHz, CDCl3): 7.54 (2H, m), 7.28 (3H, m), 5.81 (1H, m), 5.77 (1H, m), 5.00 (2H, m), 4.99 (2H, m), 4.94 (1H, m), 4.52 (1H, d, J=9.7 Hz), 4.13 (1H, m), 3.78 (1H, m), 3.60 (3H, s), 3.53 (1H, dd, app. t, J=9.3 Hz), 3.29 (3H, s), 3.14 (1H, dd, app. t, J=9.6 Hz), 3.06 (1H, dd, app. t, J=6.3 Hz), 2.32 (2H, m), 2.32 (2H, m), 2.05 (2H, m), 2.05 (2H, m), 1.62 (2H, m), 1.62 (2H, m), 1.42 (2H, m), 1.42 (2H, m)
$^{13}$C-NMR (125 MHz, CDCl3): 173.09, 172.03, 138.23, 138.06, 132.96, 132.03, 128.65, 127.54, 114.61, 114.51, 87.05, 85.61, 81.87, 75.70, 69.15, 62.35, 60.69, 60.69, 33.88, 33.68, 33.16, 33.13, 28.15, 28.03, 24.14, 23.99
C,H-analysis: calculated: C 64.59%, H 7.74%
found: C 64.79%, H 7.88%
Monoester:
Formula: $C_{21}H_{30}O_6S$
Molecular weight: 410.52
R$_f$: 0.40 (cyclohexane/ethyl acetate 1:1)
IR(KBr): 3444, 3075, 2934, 2360, 1738, 1659, 1641, 1584, 1480, 1456, 1383, 1285, 1147, 1066, 1025, 956, 913, 823, 746, 692, 588 cm$^{-1}$
ES-MS: 433=[410+Na]$^+$
$^1$H-NMR (500 MHz, CDCl3): 7.54 (2H, m), 7.27 (3H, m), 5.78 (1H, m), 4.96 (2H, m), 4.54 (1H, d, J=9.7 Hz), 4.36 (1H, m), 4.35 (1H, m), 3.66 (3H, s), 3.61 (3H, s), 3.45 (1H, m), 3.36 (1H, dd, app. t, J=9.6 Hz), 3.18 (1H, dd, app. t, J=8.8 Hz), 3.06 (1H, dd, app. t, J=8.8 Hz), 2.35 (2H, m), 2.05 (2H, m), 1.64 (2H, m), 1.42 (2H, m)

EXAMPLE 21

Synthesis of KPE00001016.1 and KPE00001016.2 via Metathesis Reaction

Figure 9:
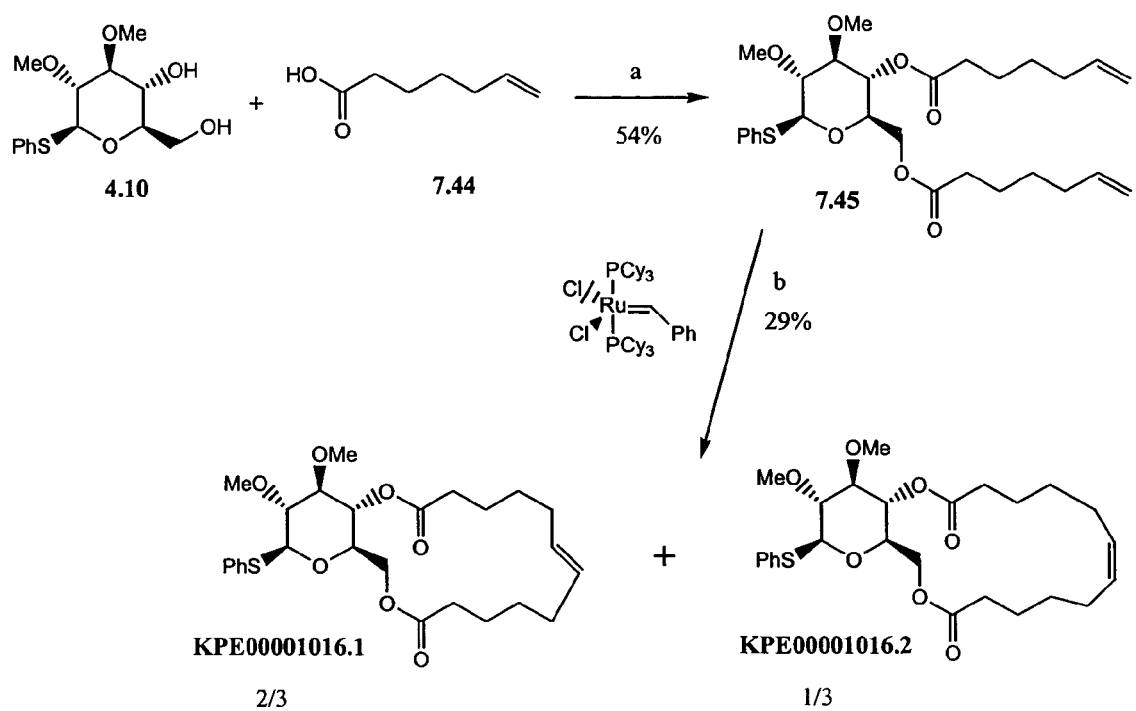
FIG. 9 is a diagrammatical representation of the synthesis scheme of macrolides KPE00001016.1 and KPE000010016.2 of the present invention.

To methylene chloride (100 ml) were added slowly and simultaneously a solution of diene (Molecule 7.45) (1.0 g, 192 mmol) in methylene chloride (100 ml) and a solution of the Grubbs' catalyst (160 mg, 0.192 mmol) in methylene chloride (100 ml). The mixture was stirred at room temperature for 46 hours. The solvent was then removed under reduced pressure. The crude product was purified by flash chromatography (gradient elution: cyclohexane/ethyl acetate 1/0 to 85/15), followed by HPLC (eluent: cyclohexane/ethyl acetate 9/1) to yield 180 mg (21%) of KPE00001016.1 and 70 mg (8%) of KPE00001016.2 (FIG. 9).

Compound KPE00001016.1:
Formula: $C_{26}H_{36}O_7S$
Molecular weight: 492.63
R$_f$: 0.34 (cyclohexane/ethyl acetate 8:2)
Melting point: 60-61° C.
$[\alpha]_D^{20}=-37.4$; $[\alpha]_{365}^{20}=-127.4$ (c=1.07 in chloroform)
IR(KBr): 2932, 2359, 1741, 1584, 1479, 1440, 1382, 1145, 1068, 969, 822, 745, 692 cm$^{-1}$
ES-MS: 510=[492+NH$_4$]$^+$
$^1$H-NMR (500 MHz, CDCl3): 7.52 (2H, m), 7.29 (3H, m), 5.37 (1H, ddd, J=15.3, 9.6, 5.8 Hz), 5.34 (1H, ddd, 15.3, 9.6, 5.8 Hz), 4.96 (1H, dd, app. t, J=9.8 Hz), 4.52 (1H, d, J=9.8 Hz), 4.32 (1H, dd, J=12.1, 8.5 Hz), 4.03 (1H, dd, J=12.1, 7.8 Hz), 3.60 (1H, s), 3.55 (1H, ddd, J=10.0, 6.0, 4.0 Hz), 3.52 (3H, s), 3.31 (1H, dd, app. t, J=9.1 Hz), 3.12 (3H, dd, app. t, J=9.8 Hz), 2.32 (2H, m), 2.25 (2H, m), 2.06 (2H, m), 2.01 (2H, m), 1.62 (2H, m), 1.58 (2H, m), 1.48 (2H, m), 1.37 (2H, m)
$^{13}$C-NMR (125 MHz, CDCl3): 173.25, 172.20, 132.63, 132.31, 132.02, 130.44, 128.72, 127.68, 87.25, 85.49, 81.79, 75.55, 70.74, 63.92, 60.71, 60.62, 34.00, 33.54, 31.21, 31.05, 27.96, 27.73, 23.71, 23.02
C,H-analysis: calculated: C 63.39%, H 7.37%, S 6.50%
found: C 63.01%, H 7.59%, S 6.50%
Compound KPE00001016.2:
Formula: $C_{26}H_{36}O_7S$
Molecular weight: 492.63
R$_f$: 0.34 (cyclohexane/ethyl acetate 8:2)
Melting point: 87-88° C.
$[\alpha]_D^{20}=+48.4$; $[\alpha]_{365}^{20}=-36.0$ (c=0.50 in chloroform)
IR(KBr): 2934, 1740, 1440, 1379, 1226, 1145, 1066, 954, 815, 746, 692 cm$^{-1}$
ES-MS: 510=[492+NH$_4$]$^+$
$^1$H-NMR (500 MHz, CDCl3): 7.53 (2H, m), 7.30 (3H, m), 5.39 (1H, m), 5.34 (1H, m), 5.03 (1H, dd, app. t, J=9.8 Hz), 4.52 (1H, d, J=9.8 Hz), 4.20 (1H, dd, J=12.1, 3.4 Hz), 4.12 (1H, dd, J=12.1, 3.6 Hz), 3.60 (3H, s), 3.56 (1H, ddd, J=3.6, 2.9 Hz), 3.52 (3H, s), 3.29 (1H, dd, app. t, J=8.7 Hz), 3.13 (3H, dd, J=8.8, 8.9 Hz), 2.33 (2H, m), 2.29 (2H, m), 2.09 (2H, m), 2.00 (2H, m), 1.64 (2H, m), 1.57 (2H, m), 1.41 (2H, m), 1.28 (2H, m)
$^{13}$C-NMR (125 MHz, CDCl3): 173.27, 171.95, 132.63, 132.32, 130.12, 129.49, 128.71, 127.69, 87.23, 85.62, 81.74, 75.41, 70.01, 63.50, 60.70, 60.61, 33.75, 33.68, 28.77, 28.60, 26.47, 26.00, 23.87, 23.71
C,H-analysis: calculated: C 63.39%, H 7.37%, S 6.50%
found: C 63.45%, H 7.53%, S 6.59%

EXAMPLE 22

Synthesis of the diether (Molecule 7.9) and the monoether (Molecule 7.10)

Figure 8:
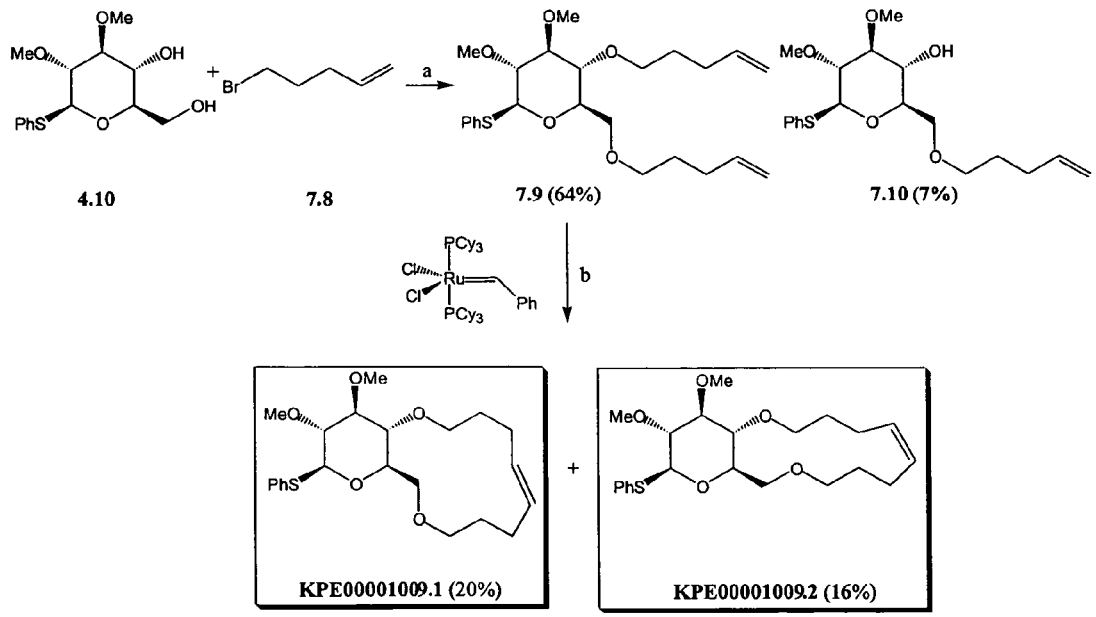
FIG. 8 is a diagrammatical representation of the synthesis scheme of macrolides KPE00001009.1 and KPE00001009.2 of the present invention.

To a solution of diol (Molecule 4.10) (1.0 g, 3.30 mmol) in dry tetrahydrofuran (30 ml) were added at room temperature tetrabutylammoniumiodide (20 mg) and 5-bromo-1-pentene (Molecule 7.8) (1.7 ml, 14.00 mmol). The mixture was cooled at 0° C. and sodiumhydride (500 mg, 60% suspension, 11.86 mmol) was added. The mixture was stirred at room temperature for 42 hours. The reaction mixture was poured into ice water (100 ml) and the two layers were separated. The water layer was extracted with diethylether (3×100 ml). The combined organic layers were dried (MgSO$_4$), filtered and the solvent was removed under reduced pressure. The crude product was purified by flash chromatography (gradient elution: cyclohexane/ethyl acetate 1/0 to 8/2) to yield 923 mg (64%) of a diether (Molecule 7.9; FIG. 8) and 90 mg (7%) of monoether (Molecule 7.10; FIG. 8).

Compound Molecule 7.9:
Formula: $C_{24}H_{36}NO_5S$
Molecular weight: 436.61
$R_f$: 0.53 (cyclohexane/ethyl acetate 8:2)
Melting point: 36-37° C.
$[\alpha]_D^{20}$=−33.24; $[\alpha]_{365}^{20}$=−65.23 (c=3.73; in chloroform)
IR(KBr): 3075, 2935, 2358, 1641, 1584, 1480, 1440, 1378, 1284, 1100, 912, 821, 692 cm$^{-1}$
ES-MS: 459=[436+Na]$^+$
$^1$H-NMR (500 MHz, CDCl3): 7.55 (2H, m), 7.26 (3H, m), 5.82 (2H, m), 5.02 (2H, m), 4.96 (2H, m), 4.48 (1H, d, J=Hz), 3.75 (1H, m), 3.67 (1H, m), 3.63 (3H, s), 3.59 (3H, s), 3.56 (1H, m), 3.49 (1H, m), 3.43 (1H, m), 3.42 (1H, m), 3.32 (1H, m), 3.22 (1H, m), 3.21 (1H, m), 3.04 (1H, m), 2.12 (2H, m), 2.11 (2H, m), 1.68 (2H, m), 1.67 (2H, m)
$^{13}$C-NMR (125 MHz, CDCl3): 138.20, 138.03, 133.71, 131.61, 128.61, 127.14, 114.62, 114.52, 88.51, 86.90, 82.38, 78.40, 77.70, 72.10, 70.73, 69.55, 60.95, 60.60, 30.16, 30.12, 29.39, 28.87
C,H-analysis: calculated: C 66.02%, H 8.31%, S 7.30%
found: C 65.88%, H 8.34%, S 7.35%

Compound Molecule 7.10:
Formula: $C_{19}H_{28}NO_5S$
Molecular weight: 368.49
$R_f$: 0.27 (cyclohexane/ethyl acetate 8:2)
IR(KBr): 3453, 2931, 1641, 1584, 1480, 1440, 1380, 1154, 1098, 913, 742, 691 cm$^{-1}$
ES-MS: 391=[368+Na]$^+$
$^1$H-NMR (500 MHz, CDCl3): 7.51 (2H, m), 7.31 (3H, m), 5.82 (1H, m), 5.04 (1H, m), 4.99 (1H, m), 4.57 (1H, d, J=9.8 Hz), 3.86 (1H, m), 3.79 (1H, m), 3.70 (1H, m), 3.66 (3H, s), 3.63 (3H, s), 3.59 (1H, m), 3.28 (1H, m), 3.26 (1H, dd, J=8.8 Hz), 3.21 (1H, dd, J=9.0 Hz), 3.04 (1H, m), 2.12 (2H, m), 1.97 (1H, m), 1.64 (2H, m)
$^{13}$C-NMR (125 MHz, CDCl3): 137.93, 135.00, 131.65, 128.82, 127.46, 114.70, 88.29, 86.86, 82.58, 79.06, 77.70, 72.22, 62.06, 60.97, 60.72, 30.04, 29.34
C,H-analysis: calculated: C 61.93%, H 7.66%, S 8.70%
found: C 62.17%, H 7.91%, S 8.24%

EXAMPLE 23

Synthesis of KPE00001009.1 and KPE00001009.2 via Metathesis Reaction

To methylene chloride (35 ml) were added slowly and simultaneously a solution of diene (Molecule 7.9) (800 mg, 1.83 mmol) in methylene chloride (35 ml) and a solution of the Grubbs' catalyst (150 mg, 0.183 mmol) in methylene chloride (35 ml). The reaction mixture was stirred at room temperature for 5 hours. An additional amount of catalyst (150 mg) in methylene chloride (35 ml) was added and the mixture was stirred for another 42 hours. The solvent was then removed under reduced pressure. The crude products were purified by flash chromatography (gradient elution: cyclohexane/ethyl acetate 1/0 to 8/2) followed by HPLC (eluent: cyclohexane/ethyl acetate 95/5) to yield 75 mg (20%) of KPE00001009.1 and 59 mg (16%) of KPE00001009.2 (FIG. 8).

Compound KPE00001009.1:
Formula: $C_{22}H_{32}O_5S$
Molecular weight: 408.55
$R_f$: 0.38 (cyclohexane/ethyl acetate 8:2)
$[\alpha]_D^{20}$=+22.6; $[\alpha]_{365}^{20}$=+4.4 (c=1.66 in chloroform)
IR(KBr): 2926, 2362, 2344, 1478, 1440, 1377, 1275, 1148, 1095, 1065, 968, 819, 691 cm$^{-1}$
ES-MS: 431=[408+Na]$^+$
$^1$H-NMR (500 MHz, CDCl3): 7.51 (2H, m), 7.26 (3H, m), 5.51 (1H, dt, J=15.1, 7.2 Hz), 5.33 (1H, dt, J=14.9, 7.2 Hz), 4.46 (1H, d), 3.65 (1H, m), 3.64 (1H, m), 3.63 (3H, s), 3.59 (1H, m), 3.58 (3H, s), 3.57 (1H, m), 3.44 (1H, ddd, J=10.0, 7.2, 2.9 Hz), 3.27 (1H, dd, app. t, J=8.7 Hz), 3.25 (1H, m), 3.18 (1H, dd, app. t, J=8.7 Hz), 3.01 (1H, dd, app. t, J=8.7 Hz), 2.19 (1H, m), 2.09 (2H, m), 2.02 (1H, m), 1.75 (2H, m), 1.69 (2H, m)
$^{13}$C-NMR (125 MHz, CDCl3): 133.74, 132.65, 131.58, 128.59, 128.18, 127.10, 87.92, 87.04, 82.04, 79.03, 77.74, 71.38, 69.76, 69.47, 61.03, 60.61, 31.67, 28.64, 28.02, 27.62

Compound KPE00001009.2:
Formula: $C_{22}H_{32}O_5S$
Molecular weight: 408.55
$R_f$: 0.41 (cyclohexane/ethyl acetate 8:2)
$[\alpha]_D^{20}$=+103.6; $[\alpha]_{365}^{20}$=+33.3 (c=0.45 in chloroform)
IR(KBr): 2929, 2360, 2341, 1477, 1440, 1379, 1275, 1148, 1101, 1065, 961, 811, 729, 691, 668 cm$^{-1}$
ES-MS: 431=[408+Na]$^+$
$^1$H-NMR (500 MHz, CDCl3): 7.51 (2H, m), 7.28 (3H, m), 5.34 (1H, m), 4.50 (1H, d, J=9.8 Hz), 3.73 (1H, m), 3.65 (3H, s), 3.64 (1H, m), 3.59 (3H, s), 3.57 (1H, m), 3.55 (1H, m), 3.42 (1H, m), 3.40 (1H, m), 3.33 (1H, dd, J=Hz), 3.21 (1H, m), 3.20 (1H, m), 3.01 (1H, dd, J=8.7 Hz), 2.45 (2H, m), 2.10 (1H, m), 2.01 (1H, m), 1.77 (2H, m), 1.72 (2H, m)
$^{13}$C-NMR (125 MHz, CDCl3): 133.65, 131.51, 130.62, 129.87, 128.64, 127.13, 88.47, 87.15, 82.15, 79.95, 78.25, 72.00, 70.48, 67.86, 61.04, 60.62, 30.13, 28.48, 23.34, 22.47

EXAMPLE 24

Synthesis of the ester (Molecule 7.13)

Figure 10:
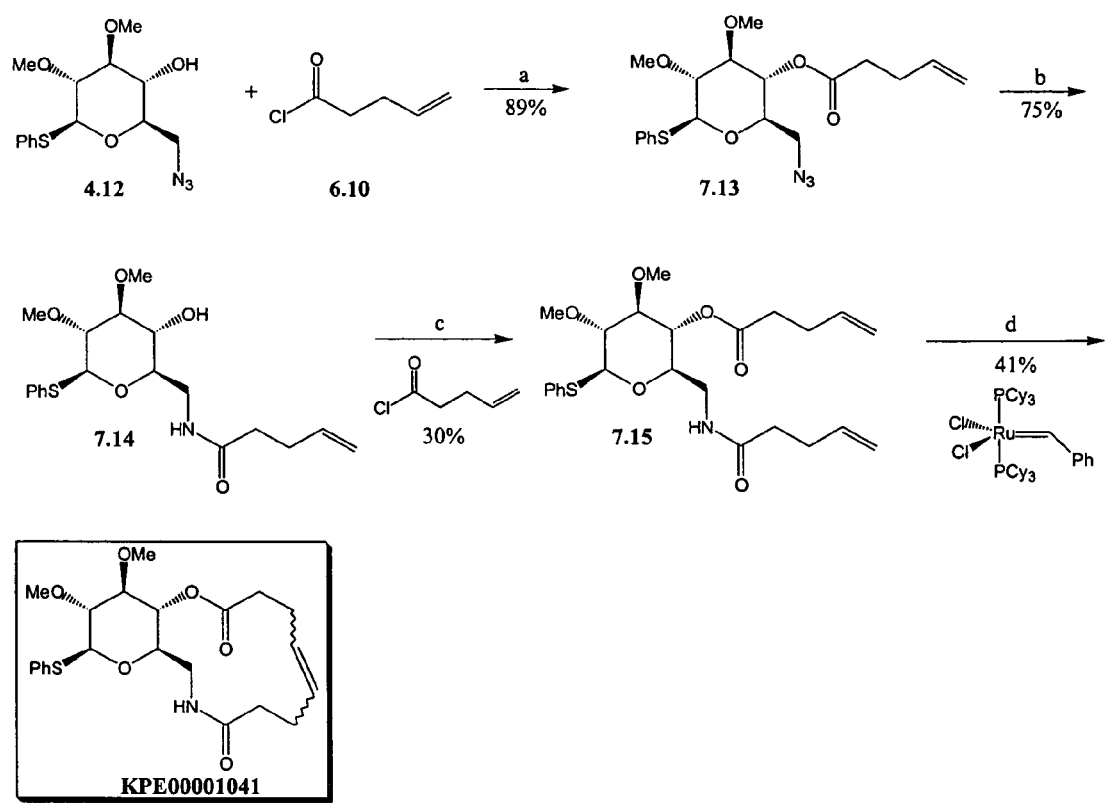
FIG. 10 is a diagrammatical representation of the synthesis scheme of macrolide KPE00001041 of the present invention.

To a solution of alcohol (Molecule 4.12) (1.0 g, 3.07 mmol) in dry methylene chloride (30 ml) were added at room temperature pyridine (0.375 ml, 4.6 mmol), dimethylaminopyridine (20 mg) and 4-pentenoyl chloride (Molecule 6.10) (437 mg, 3.7 mmol). The mixture was stirred at room temperature for 24 hours. The reaction mixture was then diluted with methylene chloride (120 ml), washed with a saturated sodium bicarbonate solution (3×150 ml) and brine (2×150 ml). The organic layer was dried (MgSO$_4$), filtered and the solvent was removed under reduced pressure. The crude product was purified by flash chromatography (eluent: cyclohexane/diethylether 8/2) to yield 1.11 g (89%) of Molecule 7.13 (FIG. 10).

Formula: $C_{19}H_{25}N_3O_5S$
Molecular weight: 407.48
$R_f$: 0.57 (cyclohexane/ethyl acetate 1:1)
$[\alpha]_D^{20}$=−77.4; $[\alpha]_{365}^{20}$=−271.7 (c=1.21 in chloroform)
IR(KBr): 3087, 2934, 2037, 2102, 1747, 1642, 1584, 1480, 1440, 1372, 1297, 1160, 960, 919, 868, 820, 747, 692 cm$^{-1}$
ES-MS: 431=[407+Na]$^+$
$^1$H-NMR (500 MHz, CDCl3): 7.57 (2H, dd, J=7.4, 1.4 Hz), 7.31 (3H, m), 5.81 (1H, ddd, 10.3, 4.0, 1.8 Hz), 5.09 (1H, dd, J=17.2, 1.4 Hz), 5.04 (1H, dd, J=10.4, 0.9 Hz), 4.83 (1H, t, J=9.7 Hz), 4.54 (1H, d, J=9.2 Hz), 3.62 (3H, s), 3.53 (3H, s), 3.47 (1H, ddd, J=9.9, 7.4, 2.5 Hz), 3.32 (1H, dd, J=13.3, 7.3 Hz), 3.29 (1H, t, J=9.2 Hz), 3.22 (1H, dd, J=13.5, 2.4 Hz), 3.13 (1H, t, J=8.8 Hz), 2.44 (2H, m), 2.39 (2H, m)
$^{13}$C-NMR (125 MHz, CDCl3): 171.66, 136.10, 132.69, 132.39, 128.48, 127.91, 115.82, 87.34, 85.45, 81.69, 76.90, 70.57, 60.78, 60.78, 51.45, 33.31, 28.57

C,H-analysis: calculated: C 56.00%, H 6.20%, N 10.30%, S 7.90%
found: C 56.35%, H 6.41%, N 9.43%, S 7.81%

EXAMPLE 25

Staudinger Reaction for the Formation of Molecule 7.14

To a solution of azide (Molecule 7.13) (500 mg, 1.227 mmol) in tetrahydrofuran (30 ml) and water (0.3 ml) was added at room temperature triphenylphosphine on carrier (660 mg, 1.980 mmol, loading 3 mmol/g). The suspension was stirred at room temperature for 48 hours. The suspension was dried ($MgSO_4$), filtered and the residue was washed with methylene chloride (3×25 ml). The solvent was removed under reduced pressure. The crude product was purified by flash chromatography (gradient elution: methylene chloride/methanol 1/0 to 9/1) to yield 350 mg (75%) of Molecule 7.14 (FIG. 10).

Formula: $C_{19}H_{27}NO_5S$
Molecular weight: 381.48
$R_f$: 0.16 (cyclohexane/ethyl acetate 1:1)
Melting point: 107-108° C.
$[\alpha]_D^{20}$=−86.7; $[\alpha]_{365}^{20}$=+463.3 (c=0.98 in chloroform)
IR(KBr): 3319, 3079, 2936, 2832, 1644, 1556, 1478, 1439, 1374, 1335, 1293, 1270, 1234, 1190, 1143, 1064, 1025, 1000, 956, 914, 856, 819, 747, 704, 690 $cm^{-1}$
ES-MS: 404=[381+Na]$^+$
$^1$H-NMR (500 MHz, CDCl3): 7.48 (2H, m), 7.29 (3H, m), 5.97 (1H, bt), 5.80 (1H, m), 5.07 (1H, dd, J=17.1, 1.4 Hz), 5.02 (1H, dd, J=10.1, 0.8 Hz), 4.56 (1H, d, J=9.8 Hz), 4.37 (1H, bs), 3.92 (1H, ddd, J=12.7, 5.7 Hz), 3.66 (3H, s), 3.61 (3H, s), 3.25 (1H, m), 3.22 (1H, m), 3.12 (2H, m), 3.00 (1H, t, J=8.5 Hz), 2.38 (2H, m), 2.30 (2H, m)
$^{13}$C-NMR (125 MHz, CDCl3): 174.23, 136.41, 133.42, 131.43, 128.79, 127.41, 115.84, 87.28, 86.58, 82.23, 78.64, 69.97, 61.00, 60.73, 39.79, 35.37, 29.30
C,H-analysis: calculated: C 59.80%, H 7.10%, N 3.70%
found: C 59.76%, H 7.08%, N 3.51%

EXAMPLE 26

Synthesis of the amide (Molecule 7.15)

To a solution of alcohol (Molecule 7.14) (0.2 g, 0.52 mmol) in dry methylene chloride (16 ml) were added at room temperature triethylamine (0.290 ml, 2.08 mmol) and 4-pentenoyl chloride (Molecule 6.10) (125 mg, 1.05 mmol). The mixture was stirred at room temperature for 24 hours. The reaction mixture was diluted with methylene chloride (35 ml), washed with a saturated sodium bicarbonate solution (2×50 ml), a 1 M HCl solution (2×50 ml) and brine (2×50 ml). The organic layer was dried ($MgSO_4$), filtered and the solvent was removed under reduced pressure. The crude product was purified by flash chromatography (gradient elution: cyclohexane/ethyl acetate 1/0 to 1/1) to yield 70 mg (30%) of Molecule 7.15 (FIG. 10).

Formula: $C_{24}H_{33}NO_6S$
Molecular weight: 463.59
$R_f$: 0.44 (cyclohexane/ethyl acetate 1:1)
Melting point: 106-107° C.
$[\alpha]_D^{20}$=−1.5; $[\alpha]_{365}^{20}$=−22.9 (c=1.04 in chloroform)
IR(KBr): 3310, 3078, 2934, 2360, 1740, 1644, 1548, 1440, 1375, 1170, 1080, 1037, 915, 822, 742, 688 $cm^{-1}$
ES-MS: 486=[463+Na]$^+$, 464=[463+H]$^+$ $^1$H-NMR (500 MHz, CDCl3): 7.50 (2H, dd, J=7.9, 1.3 Hz), 7.30 (3H, m), 5.81 (1H, m), 5.77 (1H, m), 5.71 (1H, bt), 5.05 (2H, dd, J=17.3, 1.3 Hz), 4.99 (2H, dd, J=10.4, 0.9 Hz), 4.76 (1H, t=9.7 Hz), 4.52 (1H, d, J=9.8 Hz), 3.73 (3H, ddd, J=7.8, 7.7, 2.4 Hz), 3.61 (3H, s), 3.53 (3H, s), 3.36 (1H, dd, J=7.9, 2.5 Hz), 3.29 (1H, t, J=9.1 Hz), 3.13 (1H, t, J=9.6 Hz), 2.98 (1H, dd, J=8.3, 3.6 H), 2.46 (2H, m), 2.39 (2H, m), 2.31 (2H, m), 2.17 (2H, m)
$^{13}$C-NMR (125 MHz, CDCl3): 171.93, 171.90, 136.61, 136.19, 132.65, 132.26, 128.87, 127.82, 115.67, 115.39, 86.69, 85.47, 82.36, 76.57, 70.60, 60.81, 60.81, 39.72, 35.54, 33.32, 29.26, 28.53
C,H-analysis: calculated: C 62.20%, H 7.20%, N 3.00%, S 6.90%
found: C 61.95%, H 7.43%, N 2.62%, S 5.90%

EXAMPLE 27

Synthesis of KPE00001041 via Metathesis Reaction

To methylene chloride (12 ml) were added slowly and simultaneously a solution of diene (Molecule 7.15) (80 mg, 0.172 mmol) in methylene chloride (12 ml) and a solution of the Grubbs' catalyst (86 mg, 0.104 mmol) in methylene chloride (12 ml). The mixture was stirred under reflux for 16 hours. The solvent was removed under reduced pressure. The crude product was purified by flash chromatography (gradient elution: cyclohexane/ethyl acetate 1/0 to 1/1) to yield 29 mg (41%) of KPE00001041 (FIG. 10).

Formula: $C_{22}H_{29}NO_6S$
Molecular weight: 435.53
$R_f$: 0.14 (cyclohexane/ethyl acetate 1:1)
IR(KBr): 3274, 2929, 2852, 1948, 1738, 1642, 1549, 1441, 1382, 1177, 1145, 1071, 967, 913, 822, 739, 691 $cm^{-1}$
ES-MS: 322=[435+Na]$^+$
$^1$H-NMR (500 MHz, CDCl3): 7.51 (2H, m), 7.31 (3H, m), 5.69 (1H, m), 5.54 (1H, m), 5.54 (1H, m), 4.82 (1H, dd, app. t, J=9.6, 9.5 Hz), 4.55 (1H, d, J=9.9 Hz), 3.96 (1H, m), 3.61 (3H, s), 3.59 (1H, m), 3.54 (3H, s), 3.30 (1H, dd, app. t, J=9.0, 8.9 Hz), 3.11 (1H, dd, app. t, J=9.7, 8.8 Hz), 3.07 (1H, m), 2.50 (2H, m), 2.32 (2H, m), 2.28 (2H, m), 2.22 (2H, m)
$^{13}$C-NMR (125 MHz, CDCl3): 134.43, 133.50, 132.49, 131.80, 130.40, 129.22, 88.85, 87.26, 83.87, 75.82, 75.39, 62.42, 62.25, 44.16, 38.39, 35.71, 30.32, 29.24, 28.06

EXAMPLE 28

Synthesis of the ether (Molecule 7.18)

Figure 11:
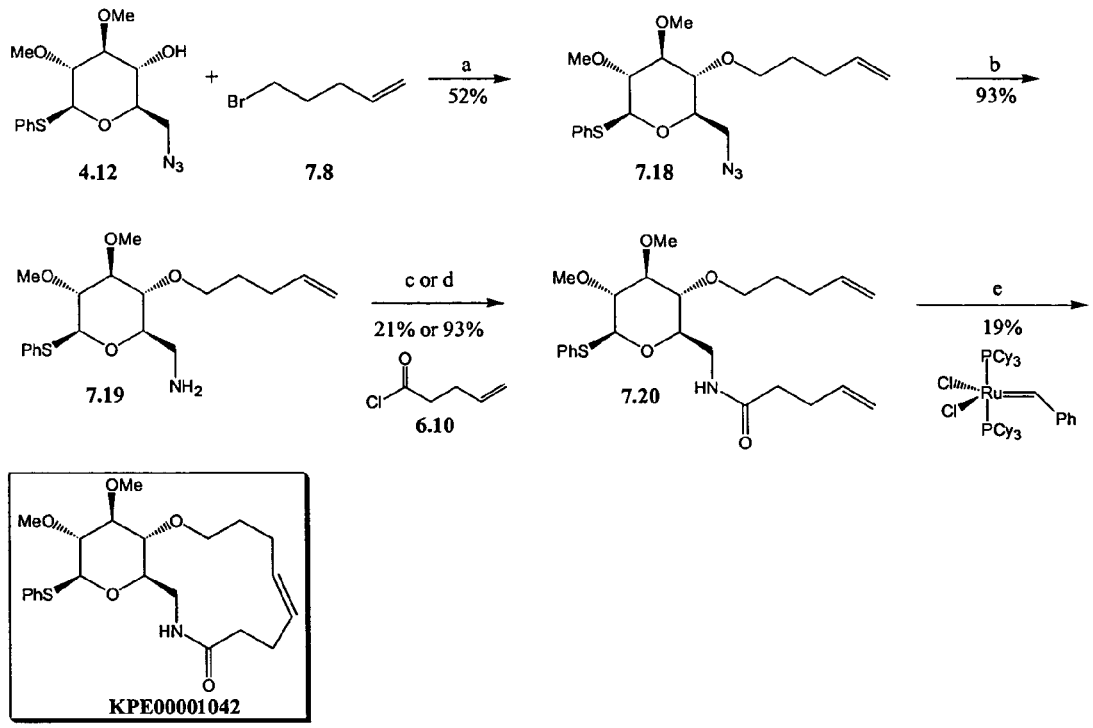
FIG. 11 is a diagrammatical representation of the synthesis scheme of macrolide KPE00001042 of the present invention.

To a solution of alcohol (Molecule 4.12) (1.0 g, 3.07 mmol) in dry tetrahydrofuran (30 ml) were added at room temperature tetrabutylammoniumiodide (30 mg) and 5-bromo-1-pentene (Molecule 7.8) (0.55 ml, 4.61 mmol). The mixture was cooled to 0° C. and sodiumhydride (250 mg, 6.14 mmol) was added. The suspension was stirred at 0° C. for 15 minutes and at room temperature for 24 hours. The mixture was poured into ice water (200 ml) and the two layers were separated. The water layer was extracted with ethyl acetate (3×200 ml). The combined organic layers were dried ($MgSO_4$), filtered and the solvent was removed under reduced pressure. The crude product was purified by flash chromatography (gradient elution: cyclohexane/ethyl acetate 1/0 to 85/15) to yield 627 mg (52%) of Molecule 7.18 (FIG. 11).

Formula: $C_{19}H_{27}N_3O_4S$
Molecular weight: 393.50
$R_f$: 0.41 (cyclohexane/ethyl acetate 8:2)
$[\alpha]_D^{20}$=−21.4; $[\alpha]_{365}^{20}$=−110.4 (c=1.52 in chloroform)

IR(KBr): 2933, 2360, 2104, 1641, 1584, 1479, 1440, 1382, 1293, 1155, 1098, 1025, 961, 914, 869, 818, 747, 692 cm$^{-1}$

ES-MS: 411=[393+NH$_4$]$^+$ $^1$H-NMR (500 MHz, CDCl3): 7.55 (1H, m), 7.29 (1H, m), 5.79 (1H, m), 5.02 (1H, m), 4.96 (1H, m), 4.48 (1H, d, J=4.48 Hz), 3.78 (1H, m), 3.62 (3H, s), 3.60 (3H, s), 3.52 (2H, m), 3.36 (1H, m), 3.32 (1H, m), 3.19 (1H, dd, app. t, J=8.9 Hz), 3.13 (1H, dd, app. t, J=9.2 Hz), 3.02 (2H, dd, J=9.7, 8.6 Hz), 2.09 (2H, m), 1.64 (2H, m)

$^{13}$C-NMR (125 MHz, CDCl3): 137.64, 132.64, 132.38, 128.52, 127.48, 114.57, 88.14, 86.92, 82.10, 77.94, 77.74, 72.07, 60.72, 60.48, 51.07, 29.83, 29.12

C,H-analysis: calculated: C 58.00%, H 6.90%, N 10.70%, S 8.10% found: C 58.37%, H 6.94%, N 10.93%, S 8.78%

EXAMPLE 29

Staudinger Reaction to Form Molecule 7.19

To a solution of azide (Molecule 7.18) (494 mg, 1.25 mmol) in a mixture of tetrahydrofuran (15 ml) and water (0.15 ml) was added at room temperature triphenylphosphine (395 mg, 1.51 mmol). The mixture was stirred at room temperature for 48 hours. The suspension was then dried (MgSO$_4$), filtered and the solvent was removed under reduced pressure. The crude product was purified by flash chromatography (gradient elution: methylene chloride/methanol 1/0 to 95/5) to yield 424 mg (93%) of Molecule 7.19 (FIG. 11).

Formula: C$_{19}$H$_{29}$NO$_4$S

Molecular weight: 367.50

R$_f$: 0.49 (dichloormethaan/methanol 9:1)

Melting point: 74-75° C.

$[\alpha]_D^{20}$=+89.3; $[\alpha]_{365}^{20}$=+79.7 (c=0.75 in chloroform)

IR(KBr): 3380, 2932, 2360, 2342, 1640, 1584, 1479, 1439, 1380, 1153, 1094, 912, 745, 722, 693, 668, 542 cm$^{-1}$

ES-MS: 368=[367+H]$^+$ $^1$H-NMR (500 MHz, CDCl3): 7.50 (3H, m), 7.28 (2H, m), 5.80 (1H, m), 5.01 (1H, dd, J=15.4, 1.8 Hz), 4.96 (1H, dd, J=8.4, 1.9 Hz), 4.52 (1H, d, J=9.9 Hz), 3.77 (1H, ddd, J=12.9, 6.5, 3.9 Hz), 3.63 (3H, s), 3.61 (3H, s), 3.52 (2H, ddd, J=13.4, 6.7, 4.3 Hz), 3.22 (1H, dd, app. t, J=8.8 Hz), 3.15 (1H, ddd, J=9.9, 7.3, 2.3 Hz), 3.04 (2H, m), 3.01 (1H, m), 2.77 (1H, dd, J=13.3, 7.5 Hz), 2.10 (2H, m), 1.65 (2H, m), 1.36 (2H, bs)

$^{13}$C-NMR (125 MHz, CDCl3): 137.90, 133.16, 131.75, 128.70, 127.34, 114.65, 88.38, 86.62, 82.77, 80.73, 79.32, 72.24, 60.89, 60.64, 43.17, 30.02, 29.35

EXAMPLE 30

Synthesis of the amide (Molecule 7.20)

To a solution of amine (Molecule 7.19) (115 mg, 0.313 mmol) in dry methylene chloride (6 ml) were added at 0° C. pyridine (0.051 ml, 0.626 mmol), dimethylaminopyridine (20 mg) and 4-pentenoyl chloride (0.042 ml, 0.376 mmol). The mixture was stirred at 0° C. for 20 min and at room temperature for 2 hours. The suspension was then diluted with methylene chloride (95 ml), washed with a saturated sodium bicarbonate solution (2×100 ml) and brine (2×100 ml). The organic layer was dried (MgSO$_4$), filtered and the solvent was removed under reduced pressure to yield 131 mg (93%) of Molecule 7.20 as a white solid (FIG. 11). The crude product was used without purification in the next step.

Formula: C$_{24}$H$_{35}$NO$_5$S

Molecular weight: 449.60

R$_f$: 0.12 (cyclohexane/ethyl acetate 8:2)

Melting point: 111-112° C.

$[\alpha]_D^{20}$=−10.5; $[\alpha]_{365}^{20}$=−86.8 (c=0.62 in chloroform)

IR(KBr): 3309, 3078, 2934, 2359, 2341, 1645, 1553, 1439, 1375, 1155, 1098, 993, 912, 820, 747, 689, 668 cm$^{-1}$

ES-MS: 450=[449+H]$^+$ $^1$H-NMR (500 MHz, CDCl3): 7.50 (2H, m), 7.30 (3H, m), 5.80 (1H, m), 5.78 (1H, m), 5.61 (1H, bt), 5.03 (2H, m), 4.97 (2H, m), 4.51 (1H, d, J=9.8 Hz), 3.76 (1H, m), 3.71 (1H, m), 3.62 (3H, s), 3.61 (3H, s), 3.54 (1H, m), 3.24 (2H, m), 3.20 (1H, dd, app. t, J=8.8 Hz), 3.01 (1H, dd, app. t, J=8.9 Hz), 2.97 (1H, dd, app. t, J=9.1 Hz), 2.32 (2H, m), 2.16 (2H, m), 2.11 (2H, m), 1.65 (2H, m)

$^{13}$C-NMR (125 MHz, CDCl3): 171.70, 137.97, 136.72, 132.85, 132.04, 128.78, 127.63, 115.39, 114.59, 88.09, 86.39, 82.68, 79.47, 77.08, 72.44, 60.98, 60.68, 40.01, 35.58, 29.99, 29.33, 29.31

C,H-analysis: calculated: C 64.11%, H 7.85%, N 3.12% found: C 64.15%, H 8.12%, N 2.88%

EXAMPLE 31

Synthesis of KPE00001042 via Metathesis Reaction

To methylene chloride (15 ml) were added slowly and simultaneously a solution of diene (Molecule 7.20) (130 mg, 0.289 mmol) in methylene chloride (15 ml) and a solution of the Grubbs' catalyst (50 mg, 0.058 mmol) in methylene chloride (15 ml). The mixture was stirred under reflux for 18 hours. The solvent was removed under reduced pressure. The crude product was purified by flash chromatography (gradient elution: cyclohexane/ethyl acetate 1/0 to 1/1), followed by HPLC (eluent: cyclohexane/ethyl acetate 1/1) to yield 23 mg (19%) of KPE00001042 (FIG. 11).

Formula: C$_{22}$H$_{31}$NO$_5$S

Molecular weight: 421.55

R$_f$: 0.18 (cyclohexane/ethyl acetate 1:1)

IR(KBr): 3301, 2931, 2360, 1641, 1534, 1440, 1382, 1259, 1152, 1080, 974, 912, 819, 740, 692 cm$^{-1}$

ES-MS: 444=[421+Na]$^+$; 422=[421+H]$^+$ $^1$H-NMR (500 MHz, CDCl3): 7.49 (2H, m), 7.29 (3H, m), 6.32 (1H, m), 5.55 (1H, ddd, J=14.8 Hz), 5.36 (1H, ddd, J=13.9 Hz), 4.48 (1H, d, J=9.9 Hz), 4.09 (1H, m), 3.80 (1H, m), 3.64 (3H, s), 3.63 (3H, s), 3.61 (1H, m), 3.19 (2H, m), 3.16 (1H, m), 3.01 (1H, m), 3.00 (1H, m), 2.41 (2H, m), 2.27 (2H, m), 2.13 (2H, m), 1.74 (2H, m)

$^{13}$C-NMR (125 MHz, CDCl3): 172.30, 133.46, 132.16, 132.11, 129.05, 128.79, 127.67, 88.09, 87.33, 82.75, 79.89, 77.11, 71.00, 61.19, 60.78, 41.44, 35.47, 29.44, 28.16

EXAMPLE 32

Synthesis of the diether (Molecule 7.25)

Figure 12:
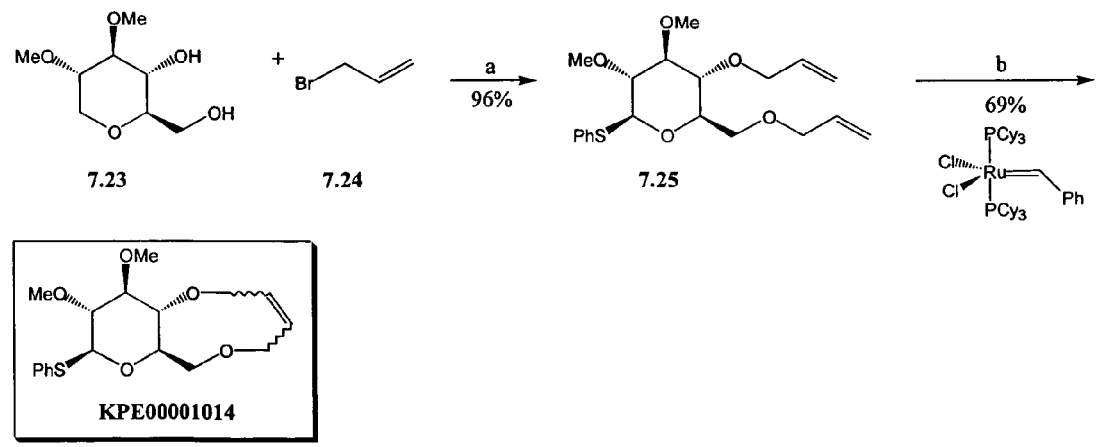
FIG. 12 is a diagrammatical representation of the synthesis scheme of macrolide KPE00001014 of the present invention.

To a solution of diol (Molecule 7.23) (2.68 g, 13.94 mmol) in dry tetrahydrofuran (140 ml) were added at room temperature tetrabutylammoniumiodide (300 mg) and allylbromide (Molecule 7.24) (3.8 ml, 43.12 mmol). The mixture was cooled to 0° C. and sodiumhydride (1.4 g, 60% suspension, 33.46 mmol) was added. The suspension was stirred at room temperature for 18 hours. The mixture was then poured into ice water (100 ml) and both layers were separated. The water layer was extracted with ethyl acetate (3×100 ml). The combined organic layers were dried (MgSO$_4$), filtered and the solvent was removed under reduced pressure. The crude product was purified by flash chromatography (gradient elution: cyclohexane/ethyl acetate 1/0 to 8/2) to yield 3.68 g (96%) of Molecule 7.25 (FIG. 12).

Formula: $C_{14}H_{24}O_5$
Molecular weight: 272.34
$R_f$: 0.16 (cyclohexane/ethyl acetate 8:2)
$[\alpha]_D^{20}=+41.9$; $[\alpha]_{365}^{20}=+124.9$ (c≈0.63 in chloroform)
IR(KBr): 3079, 2978, 2931, 2061, 1854, 1647, 1462, 1425, 1371, 1324, 1271, 1098, 996, 921, 860, 651, 588, 560 cm$^{-1}$
ES-MS: 295=[272+Na]$^+$
$^1$H-NMR (500 MHz, CDCl3): 7.55 (2H, m), 7.26 (3H, m), 5.82 (2H, m), 5.02 (2H, m), 4.96 (2H, m), 4.48 (1H, m), 3.75 (1H, m), 3.67 (1H, m), 3.63 (3H, s), 3.59 (3H, s), 3.56 (1H, m), 3.49 (1H, m), 3.43 (1H, m), 3.42 (1H, m), 3.32 (1H, m), 3.22 (1H, m), 3.21 (1H, m), 3.04 (1H, m), 2.12 (2H, m), 2.11 (2H, m), 1.68 (2H, m), 1.67 (2H, m)
$^{13}$C-NMR(125 MHz, CDCl3): 134.76, 134.36, 117.26, 116.69, 87.80, 79.84, 79.00, 73.39, 73.59, 73.35, 68.84, 67.56, 60.73, 58.62

EXAMPLE 33

Synthesis of KPE00001014 via Metathesis Reaction

To methylene chloride (100 ml) were added slowly and simultaneously a solution of diene (Molecule 7.25) (545 mg, 2.00 mmol) in methylene chloride (100 ml) and a solution of the Grubbs' catalyst (165 mg, 0.20 mmol) in methylene chloride (100 ml). The mixture was stirred at room temperature for 48 hours and the solvent was removed under reduced pressure. The crude product was purified by flash chromatography (gradient elution: cyclohexane/ethyl acetate 1/0 to 1/1) to yield 335 mg (69%) of KPE00001014 (FIG. 12).

Formula: $C_{12}H_{20}O_5$
Molecular weight: 244.29
$R_f$: 0.040 (cyclohexane/ethyl acetate 1:1)
IR(KBr): 3436, 2930, 2851, 1462, 1367, 1325, 1272, 1185, 1159, 1092, 1092, 1026, 979, 856, 728 cm$^{-1}$
ES-MS: 506=[2×244+Na]$^+$
$^1$H-NMR (500 MHz, CDCl3): 7.51 (2H, m), 7.28 (3H, m), 5.34 (1H, m), 4.50 (1H, d, J=9.8 Hz), 3.73 (1H, m), 3.65 (3H, s), 3.64 (1H, m), 3.59 (3H, s), 3.57 (1H, m), 3.55 (1H, m), 3.42 (1H, m), 3.40 (1H, m), 3.33 (1H, dd, J=Hz), 3.21 (1H, m), 3.20 (1H, m), 3.01 (1H, dd, J=8.7 Hz), 2.45 (2H, m), 2.10 (1H, m), 2.01 (1H, m), 1.77 (2H, m), 1.72 (2H, m)
$^{13}$C-NMR (125 MHz, CDCl3): 131.07, 130.18, 129.97, 128.49, 88.28, 87.83, 79.77, 79.75, 78.78, 78.65, 78.57, 77.11, 76.78, 74.99, 72.58, 71.78, 71.28, 70.83, 68.21, 67.01, 60.57, 60.54, 58.59, 58.56

EXAMPLE 34

Synthesis of the diester (Molecule 7.33)

To a solution of diol (Molecule 7.32) (300 mg, 1.120 mmol) in dimethylformamide (10 ml) were added at 0° C. pyridine (0.2 ml, 2.46 mmol) and 4-pentenoyl chloride (Molecule 6.10) (291 mg, 2.460 mmol). The mixture was stirred at room temperature for 3 hours and at 95° C. for 2 hours. The suspension was poured into water (50 ml) and the two layers were separated. The water layer was extracted with diethylether (3×50 ml). The combined organic layers were dried (MgSO$_4$), filtered and the solvent was removed under reduced pressure. The crude product was purified by flash chromatography (eluent: cyclohexane/ethyl acetate 9/1) to yield Molecule 7.33 (FIG. 13) as a white solid (157 mg, 32%).

Formula: $C_{24}H_{32}O_7$
Molecular weight: 432.51
$R_f$: 0.18 (cyclohexane/ethyl acetate 9:1)
$[\alpha]_D^{20}=-28.9$; $[\alpha]_{365}^{20}=-35.9$ (c=0.46 in chloroform)
IR(KBr): 3078, 2935, 2361, 1743, 1642, 1496, 1454, 1369, 1241, 1153, 1114, 1072, 1050, 1029, 916, 763, 700 cm$^{-1}$
ES-MS: 450=[432+NH$_4$]$^+$
$^1$H-NMR (500 MHz, CDCl3): 7.37 (2H, m), 7.33 (3H, m), 5.84 (1H, m), 5.79 (1H, m), 5.06 (2H, dd), 5.03 (2H, dd), 4.95 (1H, dd, app. t, J=10.2, 8.8 Hz), 4.20 (1H, dd), 4.15 (1H, dd, J=Hz), 4.12 (1H, d, J=9.5 Hz), 3.66 (1H, ddd, J=Hz), 3.54 (3H, s), 3.38 (1H, dd, app. t, J=9.1 Hz), 3.17 (1H, dd, app. t, J=9.2 Hz), 2.99 (3H, s), 2.45 (2H, m), 2.42 (2H, m), 2.38 (2H, m), 2.34 (2H, m)
$^{13}$C-NMR (125 MHz, CDCl3): 172.63, 171.60, 138.32, 136.50, 136.20, 128.16, 128.11, 127.13, 115.57, 115.22, 85.48, 85.39, 81.32, 75.90, 69.74, 62.57, 60.61, 60.11, 33.34, 33.10, 28.56, 28.48

EXAMPLE 35

Synthesis of KPE00001018 via Metathesis Reaction

Figure 13:
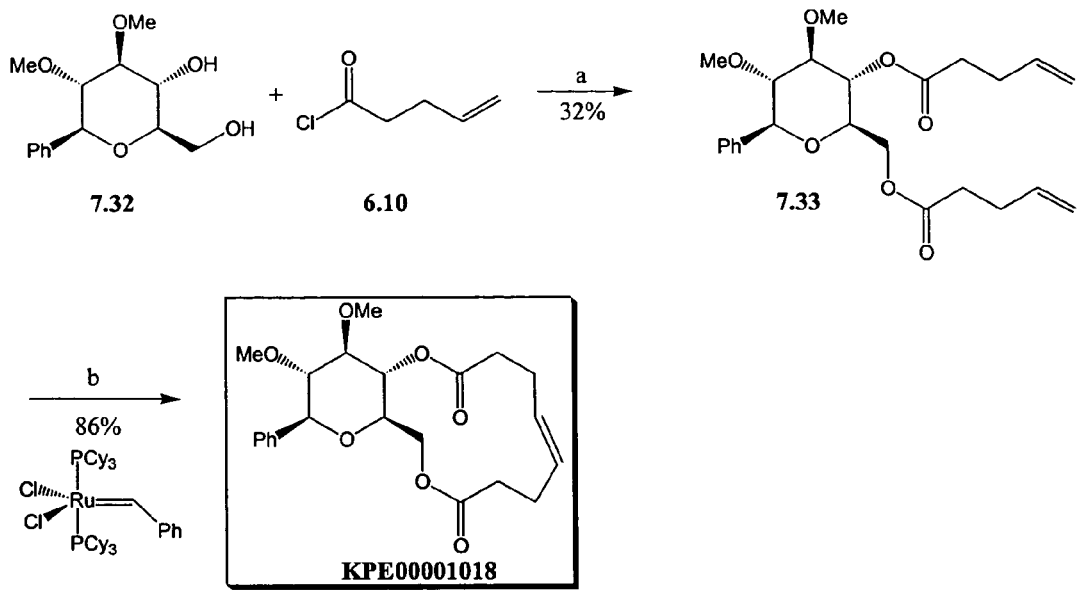
FIG. 13 is a diagrammatical representation of the synthesis scheme of macrolide KPE00001018 of the present invention.

To methylene chloride (5 ml) were added slowly and simultaneously a solution of diene (Molecule 7.33) (100 mg, 0.231 mmol) in methylene chloride (5 ml) and a solution of the Grubbs' catalyst (50 mg, 0.058 mmol) in methylene chloride (5 ml). The mixture was stirred at room temperature for 72 hours. The solvent was then removed under reduced pressure. The crude product was purified by flash chromatography (eluent: cyclohexane/ethyl acetate 8/2) to yield 80 mg (86%) of KPE00001018 (FIG. 13).

Formula: $C_{22}H_{28}O_7$
Molecular weight: 404.46
$R_f$: 0.20 (cyclohexane/ethyl acetate 8:2)
Melting point: 146-147° C.
$[\alpha]_D^{20}=-3.2$; $[\alpha]_{365}^{20}=-6.7$ (c=0.60 in chloroform)
IR(KBr): 2983, 2928, 2359, 1746, 1728, 1443, 1423, 1356, 1338, 1240, 1176, 1084, 1071, 1050, 1029, 994, 964, 964, 871, 768, 702 cm$^{-1}$
ES-MS: 422=[404+NH$_4$]$^+$
$^1$H-NMR (500 MHz, CDCl3): 7.39 (2H, m), 7.33 (3H, m), 5.56 (1H, ddd, J=15.1, 8.0, 5.0 Hz), 5.37 (3H, ddd, J=14.8, 8.8, 5.0 Hz), 5.19 (1H, dd, app. t, J=9.8 Hz), 4.30 (1H, dd, J=12.5, 9.6 Hz), 4.15 (1H, d, J=9.5 Hz), 4.08 (1H, dd, J=12.6, 9.9 Hz), 3.72 (1H, ddd, J=10.0, 7.1, 2.9 Hz), 3.53 (3H, s), 3.37 (1H, dd, app. t, J=9.6 Hz), 3.28 (1H, dd, app. t, J=9.4 Hz), 3.03 (3H, s), 2.50 (2H, m), 2.35 (2H, m), 2.26 (2H, m), 2.17 (2H, m)
$^{13}$C-NMR (125 MHz, CDCl3): 173.44, 170.99, 138.35, 131.68, 128.92, 128.24, 128.20, 127.21, 85.81, 85.47, 82.36, 75.68, 70.47, 63.94, 60.43, 60.21, 34.56, 33.63, 28.73, 26.64
C,H-analysis: calculated: C 65.30%, H 7.00%
found: C 65.00%, H 6.90%

EXAMPLE 36

Synthesis of the diester (Molecule 7.42)

To a solution of diol (Molecule 7.41) (100 mg, 0.354 mmol) in dry methylene chloride (5 ml) were added at 0° C. pyridine (0.24 ml, 2.84 mmol), dimethylaminopyridine (12 mg, 0.1 mmol) and 4-pentenoyl chloride (Molecule 6.10) (0.24 ml, 2.12 mmol). The solution was stirred at room temperature for 12 hours. The mixture was diluted with methylene chloride (45 ml), washed with a saturated sodium bicarbonate solution (2×50 ml) and brine (2×50 ml). The organic layer was dried (MgSO$_4$), filtered and the solvent was removed under reduced pressure. The crude product was purified by flash chromatography (gradient eluent: cyclohexane/ethyl acetate 1/0 to 9/1) to yield Molecule 7.42 (FIG. 14) as a yellow oil (155 mg, 98%).

Formula: $C_{25}H_{34}O_7$
Molecular weight: 446.54
$R_f$: 0.59 (cyclohexane/ethyl acetate 1:1)
$[\alpha]_D^{20}$=−10.0; $[\alpha]_{365}^{20}$=−11.1 (c=0.45 in chloroform)
IR(KBr): 2931, 2360, 1744, 1642, 1496, 1454, 1362, 1241, 1163, 1086, 953, 916, 754, 701, 628 cm$^{-1}$
ES-MS: 464=[446+NH$_4$]$^+$
$^1$H-NMR (500 MHz, CDCl3): 7.27 (2H, m), 7.26 (2H, m), 7.19 (1H, m), 5.82 (1H, m), 5.78 (1H, m), 5.06 (2H, m), 4.99 (2H, m), 4.87 (1H, dd, app. t, J=9.6 Hz), 4.10 (1H, dd, J=12.0, 6.1 Hz), 4.02 (1H, dd, J=12.1, 2.3 Hz), 3.59 (3H, s), 3.52 (3H, s), 3.39 (1H, m), 3.34 (1H, ddd, J=11.3, 9.2, 2.1 Hz), 3.28 (1H, dd, app. t, J=9.1 Hz), 3.08 (1H, dd, J=14.3, 2.1 Hz), 2.98 (1H, dd, app. t, J=9.1 Hz), 2.72 (1H, dd, J=14.3, 8.8 Hz), 2.43 (2H, m), 2.40 (2H, m), 2.36 (2H, m), 2.31 (2H, m)
$^{13}$C-NMR (125 MHz, CDCl3): 172.56, 171.66, 138.22, 136.55, 136.20, 129.52, 127.89, 126.09, 115.65, 115.24, 86.18, 82.95, 79.80, 75.42, 70.28, 62.62, 60.64, 60.46, 37.43, 33.35, 33.10, 28.55, 28.48
C,H-analysis: calculated: C 67.20%, H 7.70%
found: C 67.46%, H 7.28%

EXAMPLE 37

Synthesis of KPE00001022 via Metathesis Reaction

Figure 14:
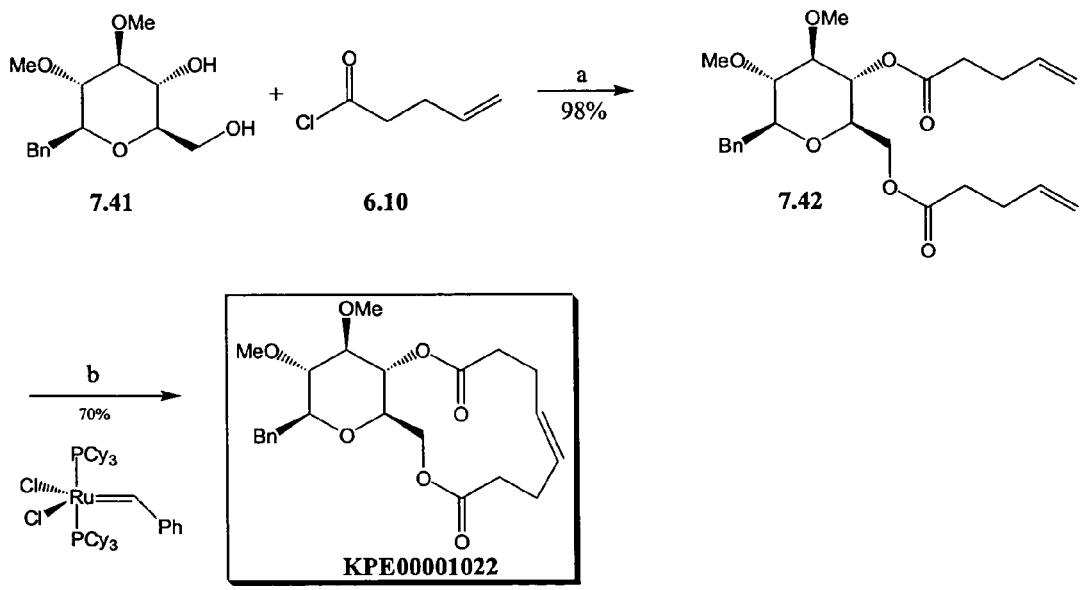
FIG. 14 is a diagrammatical representation of the synthesis scheme of macrolide KPE00001022 of the present invention.

To methylene chloride (12 ml) were added slowly and simultaneously a solution of diene (Molecule 7.42) (120 mg, 0.268 mmol) in methylene chloride (12 ml) and a solution of the Grubbs' catalyst (25 mg, 0.027 mmol) in methylene chloride (12 ml). The mixture was stirred at room temperature for 24 hours. The solvent was then removed under reduced pressure. The crude product was purified by flash chromatography (gradient elution: cyclohexane/ethyl acetate 97.5/2.5 tot 8/2), followed by HPLC (eluent: cyclohexane/ethyl acetate 8/2) to yield 78 mg (70%) of KPE00001022 (FIG. 14).

Formula: $C_{23}H_{30}O_7$
Molecular weight: 418.49
$R_f$: 0.17 (cyclohexane/ethyl acetate 8:2)
$[\alpha]_D^{20}$=−24.1; $[\alpha]_{365}^{20}$=−103.3 (c=0.46 in chloroform)
IR(KBr): 2929, 2360, 1738, 1496, 1444, 1384, 1350, 1236, 1172, 1140, 1086, 996, 958, 754, 701, 534 cm$^{-1}$
ES-MS: 436=[418+NH$_4$]$^+$
$^1$H-NMR (500 MHz, CDCl3): 7.27 (2H, m), 7.20 (3H, m), 5.52 (1H, ddd, J=14.9, 7.0, 3.0 Hz), 5.34 (1H, ddd, J=14.2, 8.4, 5.1 Hz), 5.01 (1H, dd, apt.t, J=9.8 Hz), 4.15 (1H, dd, J=12.4, 2.9 Hz), 3.60 (3H, s), 3.50 (3H, s), 3.39 (1H, m), 3.43 (1H, ddd, J=9.8, 5.9, 3.0 Hz), 3.26 (1H, dd, app. t, J=9.5 Hz), 3.08 (1H, dd, J=14.2, 1.9 Hz), 3.04 (1H, dd, app. t, J=9.0 Hz), 2.71 (1H, dd, J=14.2, 8.9 Hz), 2.44 (2H, m), 2.31 (2H, m), 2.28 (2H, m), 2.25 (1H, m), 2.10 (1H, m)
$^{13}$C-NMR (125 MHz, CDCl3): 143.47, 170.99, 138.23, 131.46, 129.38, 128.92, 127.94, 126.07, 85.56, 83.15, 80.81, 75.07, 71.00, 64.14, 60.66, 60.23, 37.70, 34.64, 33.62, 28.67, 26.49
C,H-analysis: calculated: C 66.00%, H 7.20%
found: C 65.47%, H 7.01%

EXAMPLE 38

Synthesis of the diester (Molecule 7.49)

To a solution of diol (Molecule 7.31) (228 mg, 0.850 mmol) in dry methylene chloride (15 ml) were added at 0° C. pyridine (0.275 ml, 3.40 mmol), dimethylaminopyridine (10 mg, 0.085 mmol) and 6-heptenoyl chloride (Molecule 7.48) (375 mg, 2.55 mmol). The suspension was stirred at room temperature for 18 hours. The mixture was then diluted with methylene chloride (140 ml), washed with a saturated sodium bicarbonate solution (3×150 ml) and brine (3×150 ml). The organic layer was dried (MgSO$_4$), filtered and the solvent was removed under reduced pressure. The crude product was purified by flash chromatography (gradient elution: cyclohexane/ethyl acetate 1/0 to 9/1) to yield Molecule 7.49 (FIG. 15) as a yellow solid (344 mg, 80%).

Formula: $C_{28}H_{40}O_7$
Molecular weight: 488.62
$R_f$: 0.65 (cyclohexane/ethyl acetate 1:1)
Melting point: 34-35° C.
$[\alpha]_D^{20}$=+17.0; $[\alpha]_{365}^{20}$=+6.1 (c=0.98 in chloroform)
IR(KBr): 3074, 2934, 2861, 1743, 1640, 1497, 1455, 1416, 1375, 1152, 1114, 1072, 1029, 996, 956, 912, 763, 700 cm$^{-1}$
ES-MS: 506=[488+NH$_4$]$^+$
$^1$H-NMR (500 MHz, CDCl3): 7.39 (2H, m), 7.34 (2H, m), 5.82 (1H, m), 5.76 (1H, m), 5.06 (1H, dd, J=9.8, 9.7 Hz), 5.02 (2H, m), 4.95 (2H, m), 4.19 (1H, dd, J=12.3, 5.1 Hz), 4.14 (1H, m), 4.14 (1H, d, J=9.7 Hz), 3.67 (1H, ddd, J=7.3, 5.0, 2.3 Hz), 3.55 (3H, s), 3.38 (3H, dd, J=9.2, 9.1 Hz), 3.17 (1H, dd, J=9.3, 9.1 Hz), 3.00 (3H, s), 2.34 (4H, m), 2.06 (4H, m), 1.65 (4H, m), 1.43 (4H, m)
$^{13}$C-NMR (125 MHz, CDCl3): 173.24, 172.16, 138.36, 138.28, 138.11, 128.14, 128.08, 127.12, 114.58, 114.41, 85.52, 85.42, 81.32, 75.96, 69.61, 62.46, 60.55, 60.08, 33.97, 33.70, 33.15, 33.15, 28.07, 28.07, 24.20, 24.03
C,H-analysis: calculated: C 68.83%, H 8.25%
found: C 68.20%, H 8.25%

EXAMPLE 39

Synthesis of KPE00001040E and KPE00001040Z via Metathesis Reaction

Figure 15:
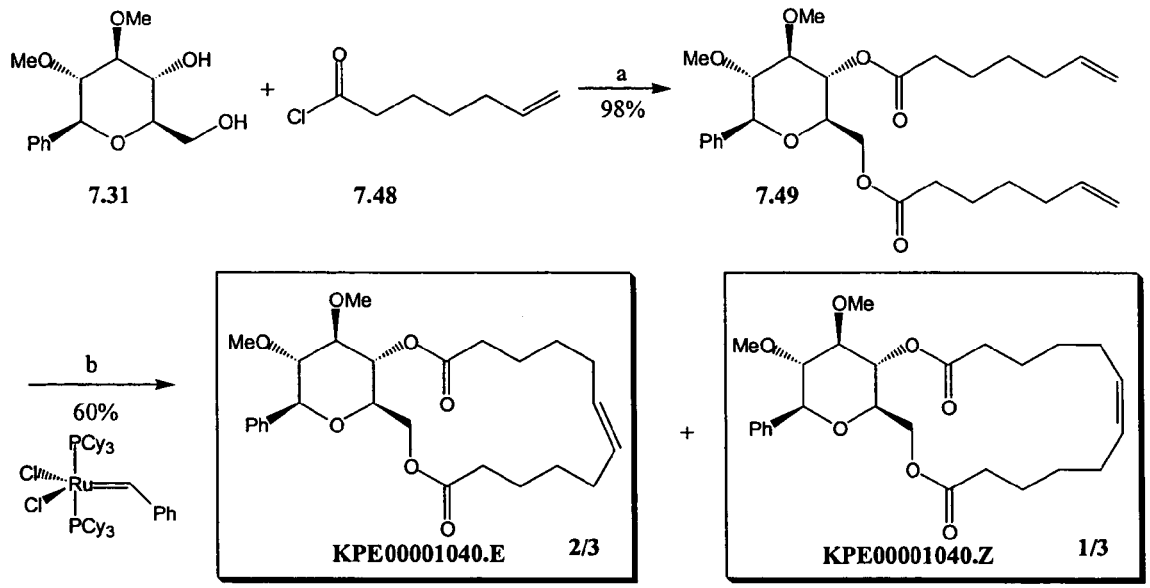
FIG. 15 is a diagrammatical representation of the synthesis scheme of macrolides KPE00001040.E and KPE00000040.Z of the present invention.

To methylene chloride (30 ml) were added slowly and simultaneously a solution of diene (Molecule 7.49) (245 mg, 0.50 mmol) in methylene chloride (30 ml) and a solution of the Grubbs' catalyst (82 mg, 0.10 mmol) in methylene chloride (30 ml). The mixture was stirred at room temperature for 46 hours. The solvent was then removed under reduced pressure. The crude products were purified by flash chromatography (gradient elution: cyclohexane/ethyl acetate 1/0 to 8/2) to yield 137 mg (60%) of KPE00001040E and KPE00001040Z (FIG. 15).

Formula: $C_{26}H_{36}O_7$
Molecular weight: 460.57
$R_f$: 0.34 (cyclohexane/ethyl acetate 8:2)
IR(KBr): 2931, 2360, 2842, 1739, 1455, 1379, 1256, 1226, 1149, 1092, 1067, 1026, 964, 913, 764, 728, 703 cm$^{-1}$
ES-MS: 461=[460+H]$^+$, 478=[460+NH$_4$]$^+$
$^1$H-NMR (500 MHz, CDCl3): 7.36 (5H, m), 5.39 (1H, m), 5.38 (1H, m), 5.12 (1H, dd, J=9.8, 9.7 Hz), 4.30 (1H, dd, J=12.2, 3.6 Hz), 4.15 (1H, d, J=9.5 Hz), 4.07 (1H, dd, J=12.1, 4.1 Hz), 3.69 (1H, m), 3.55 (3H, s), 3.39 (1H, dd, app. t, J=9.2 Hz), 3.19 (1H, dd, app. t, J=9.1 Hz), 3.01 (3H, s), 2.34 (4H, m), 2.05 (4H, m), 1.63 (4H, m), 1.42 (4H, m)
$^{13}$C-NMR (125 MHz, CDCl3): 173.95, 172.99, 138.93, 131.64, 131.06, 128.76, 127.73, 86.02, 82.16, 76.50, 71.70, 71.26, 65.00, 61.14, 60.73, 34.59, 34.36, 31.83, 29.40, 28.59, 27.09, 24.52, 24.34

EXAMPLE 40

Synthesis of the epoxide (KPE00001039)

Figure 16:
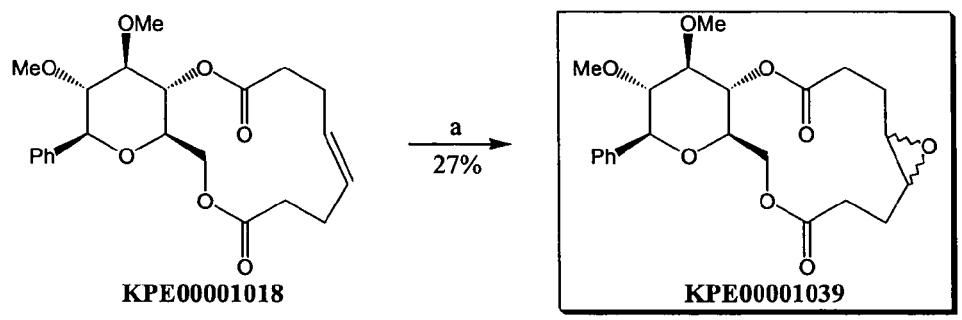
FIG. 16 is a diagrammatical representation of the synthesis scheme of macrolide KPE00001039 of the present invention.

To a solution of alkene (KPE00001018) (18 mg, 0.044 mmol) in dry methylene chloride (1 ml) was added at room temperature m-chloroperbenzoic acid. The mixture was stirred at room temperature for 72 hours. The solution was diluted with methylene chloride (30 ml) and washed with brine (3×30 ml). The organic layer was dried (MgSO$_4$), filtered and the solvent was removed under reduced pressure. The crude product was purified by flash chromatography (gradient elution: cyclohexane/ethyl acetate 1/0 to 6/4) to yield 5 mg (27%) of Molecule KPE00001039 (FIG. 16).

Formula: $C_{22}H_{28}O_8$
Molecular weight: 420.46
R$_f$: 0.37 (cyclohexane/ethyl acetate 1:1)
IR(KBr): 3456, 2924, 1744, 1450, 1417, 1378, 1222, 1180, 1067, 978, 872, 767, 700 cm$^{-1}$
ES-MS: 421=[420+H]$^+$, 438=[470+NH$_4$]$^+$
$^1$H-NMR (500 MHz, CDCl3): 7.44 (2H, m), 7.37 (3H, m), 5.30 (1H, dd, app. t, J=9.9 Hz), 5.03 (1H, dd, J=12.8, 2.7 Hz), 4.16 (1H, d, J=9.5 Hz), 3.83 (1H, m), 3.75 (1H, dd, J=9.9, 2.7 Hz), 3.54 (3H, s), 3.38 (3H, dd, J=9.7, 8.8 Hz), 3.29 (1H, dd, J=9.3, 8.8 Hz), 3.02 (3H, s), 2.90 (1H, m), 2.70 (1H, m), 2.54 (4H, m), 2.35 (4H, m)
$^{13}$C-NMR (125 MHz, CDCl3): 171.82, 171.82, 138.82, 128.86, 127.83, 127.66, 86.41, 86.04, 83.04, 76.94, 69.68, 62.82, 61.16, 60.79, 59.79, 58.72, 29.81, 29.56, 27.10, 26.71

EXAMPLE 41

Synthesis of the diester (Molecule 7.59)

To a solution of diol (Molecule 7.41) (100 mg, 0.354 mmol) in dry methylene chloride (6 ml) were added at 0° C. pyridine (0.09 ml, 1.06 mmol), dimethylaminopyridine (10 mg) and 10-undecenoyl chloride (Molecule 7.52, FIG. 17) (0.170 ml, 0.779 mmol). The solution was stirred at room temperature for 18 hours. The mixture was then diluted with methylene chloride (30 ml), washed with a saturated sodium bicarbonate solution (3×100 ml) and brine (3×100 ml). The organic layer was dried (MgSO$_4$), filtered and the solvent was removed under reduced pressure. The crude product was purified by flash chromatography (gradient elution: cyclohexane/ethyl acetate 1/0 to 9/1) to yield Molecule 7.59(FIG. 17) as a yellow solid (173 mg, 80%).

Formula: $C_{37}H_{58}O_7$
Molecular weight: 614.86
R$_f$: 0.68 (cyclohexane/ethyl acetate 1:1)
$[\alpha]_D^{20}$=-12.1; $[\alpha]_{365}^{20}$=-35.7 (c=1.00 in chloroform)
IR(KBr): 3076, 2927, 2855, 1746, 1640, 1604, 1496, 1455, 1379, 1236, 1152, 1086, 1024, 954, 909, 753, 700, 628, 496 cm$^{-1}$
ES-MS: 632=[614+NH$_4$]$^+$
$^1$H-NMR (500 MHz, CDCl3): 7.28 (4H, m), 7.22 (1H, m), 5.83 (1H, m), 5.81 (1H, m), 5.00 (2H, m), 4.94 (2H, m), 4.89 (1H, dd, app. t, J=9.7 Hz), 4.11 (1H, dd, J=12.1, 6.2 Hz), 4.03 (1H, dd, J=12.0, 2.4 Hz), 3.61 (3H, s), 3.54 (3H, s), 3.41 (1H, ddd, J=12.4, 6.1, 2.3 Hz), 3.35 (1H, ddd, J=11.3, 9.2, 2.2 Hz), 3.30 (1H, dd, app. t, J=9.1 Hz), 3.10 (1H, dd, J=14.3, 2.1 Hz), 3.00 (1H, dd, app. t, J=9.2 Hz), 2.75 (1H, dd, J=14.3, 8.8 Hz), 2.33 (2H, m), 2.24 (2H, m), 2.05 (4H, m), 1.60 (4H, m), 1.38 (4H, m), 1.29 (4H, m), 1.29 (4H, m), 1.29 (4H, m), 1.29 (4H, m)
$^{13}$C-NMR (125 MHz, CDCl3): 173.32, 172.33, 139.02, 139.02, 138.22, 129.50, 127.84, 126.02, 113.98, 113.98, 86.20, 82.91, 79.74, 75.44, 70.07, 62.48, 60.60, 60.39, 37.38, 34.14, 33.89, 33.61, 29.16, 29.04, 28.69, 24.72, 24.54
C,H-analysis: calculated: C 72.28%, H 9.51%
found: C 72.09%, H 9.15%

EXAMPLE 42

Synthesis of KPE00001031E and KPE00001031Z via Metathesis Reaction

Figure 17:
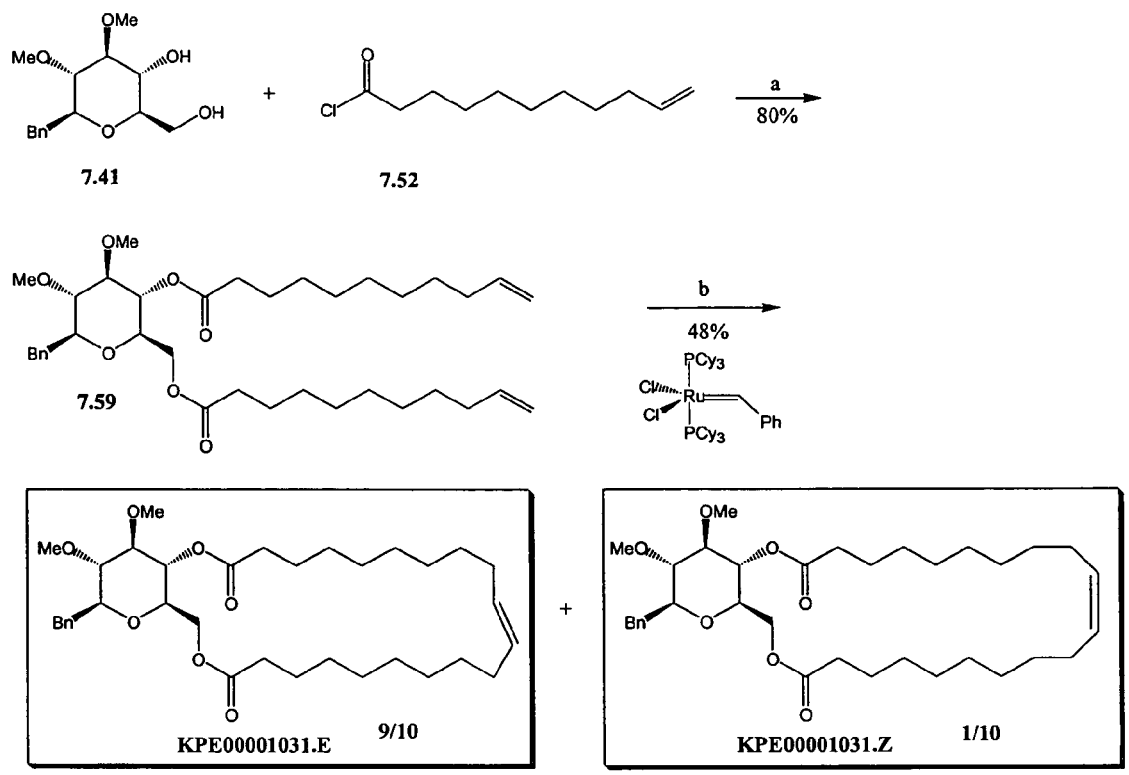
FIG. 17 is a diagrammatical representation of the synthesis scheme of macrolides KPE00001031.E and KPE000010031.Z of the present invention.
Figure 18:
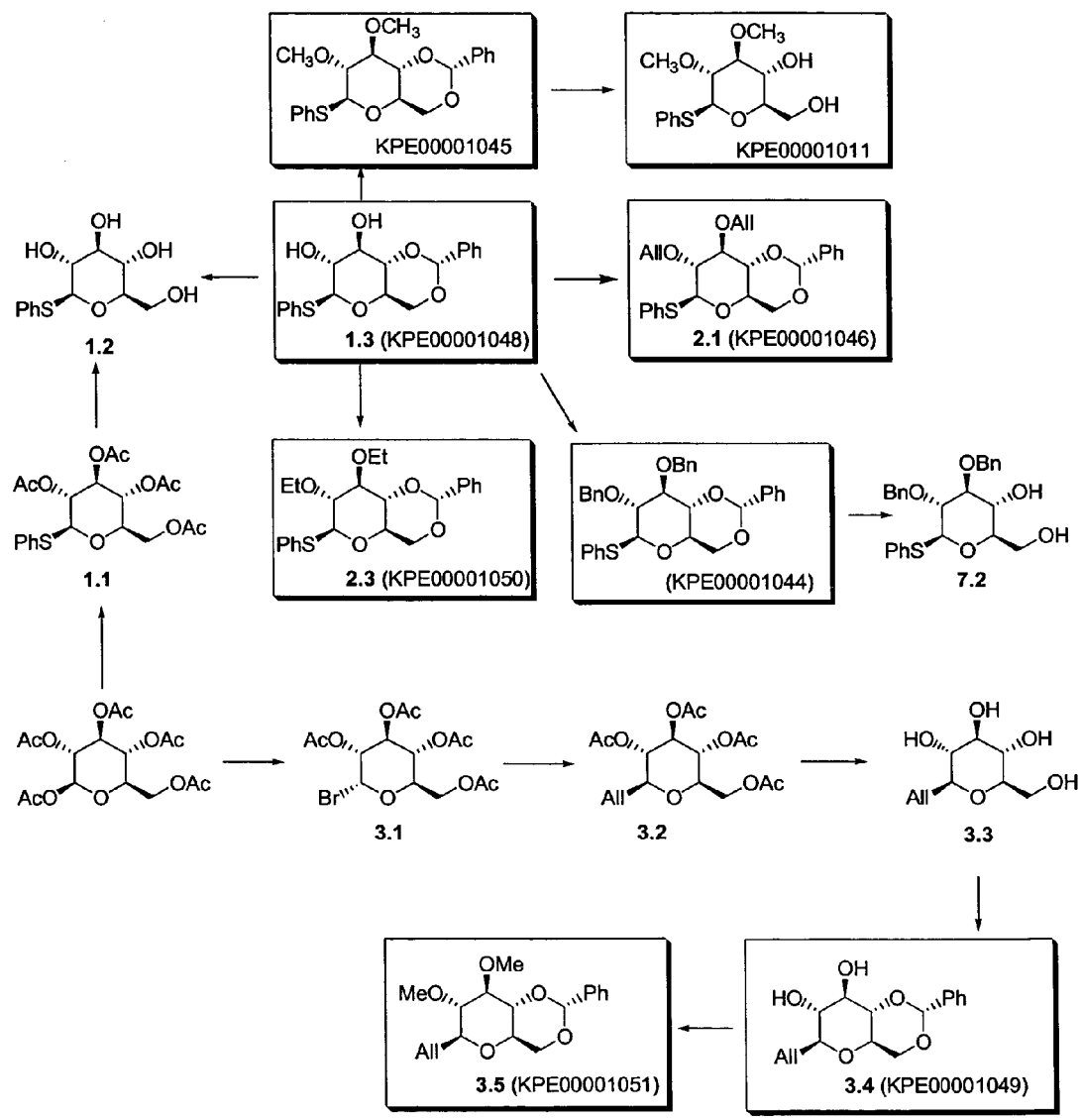
FIG. 18 is a diagrammatical representation of the synthesis scheme of macrolides KPE00001011 and KPE00001044 through KPE00001051 of the present invention.
Figure 19:
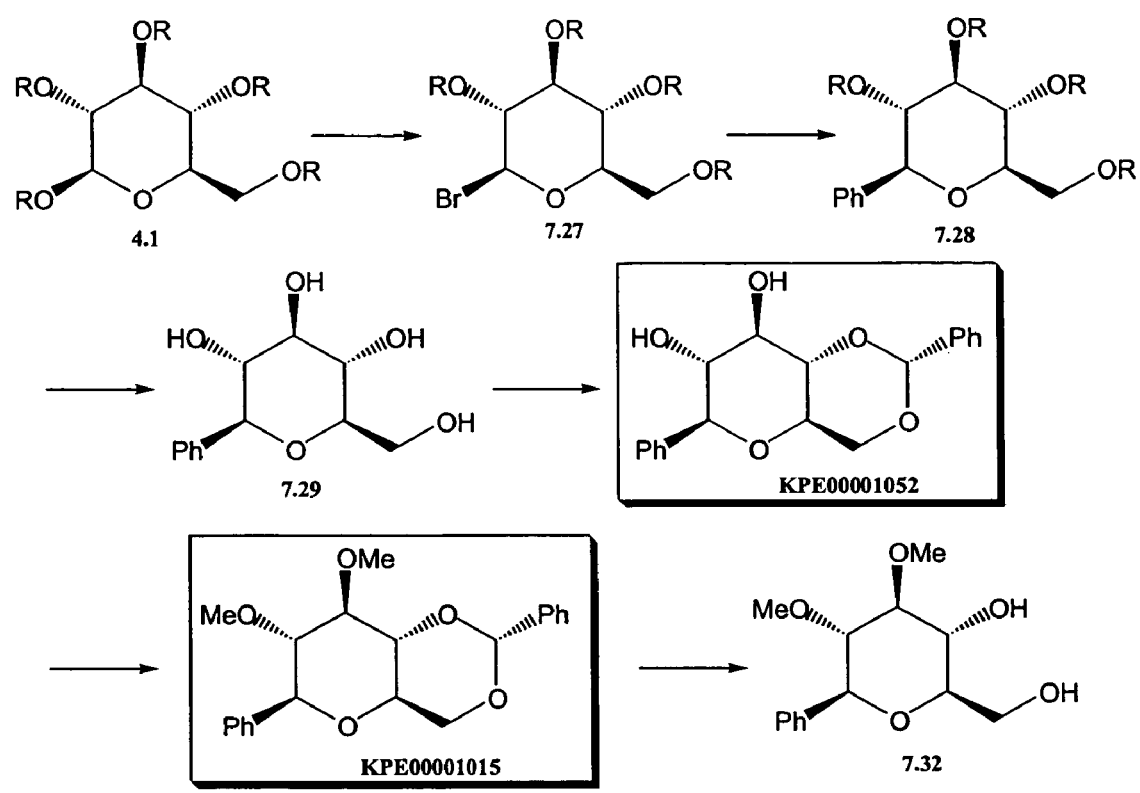
FIG. 19 is a diagrammatical representation of the synthesis scheme of macrolides KPE00001015 and KPE00001052 of the present invention.
Figure 20:
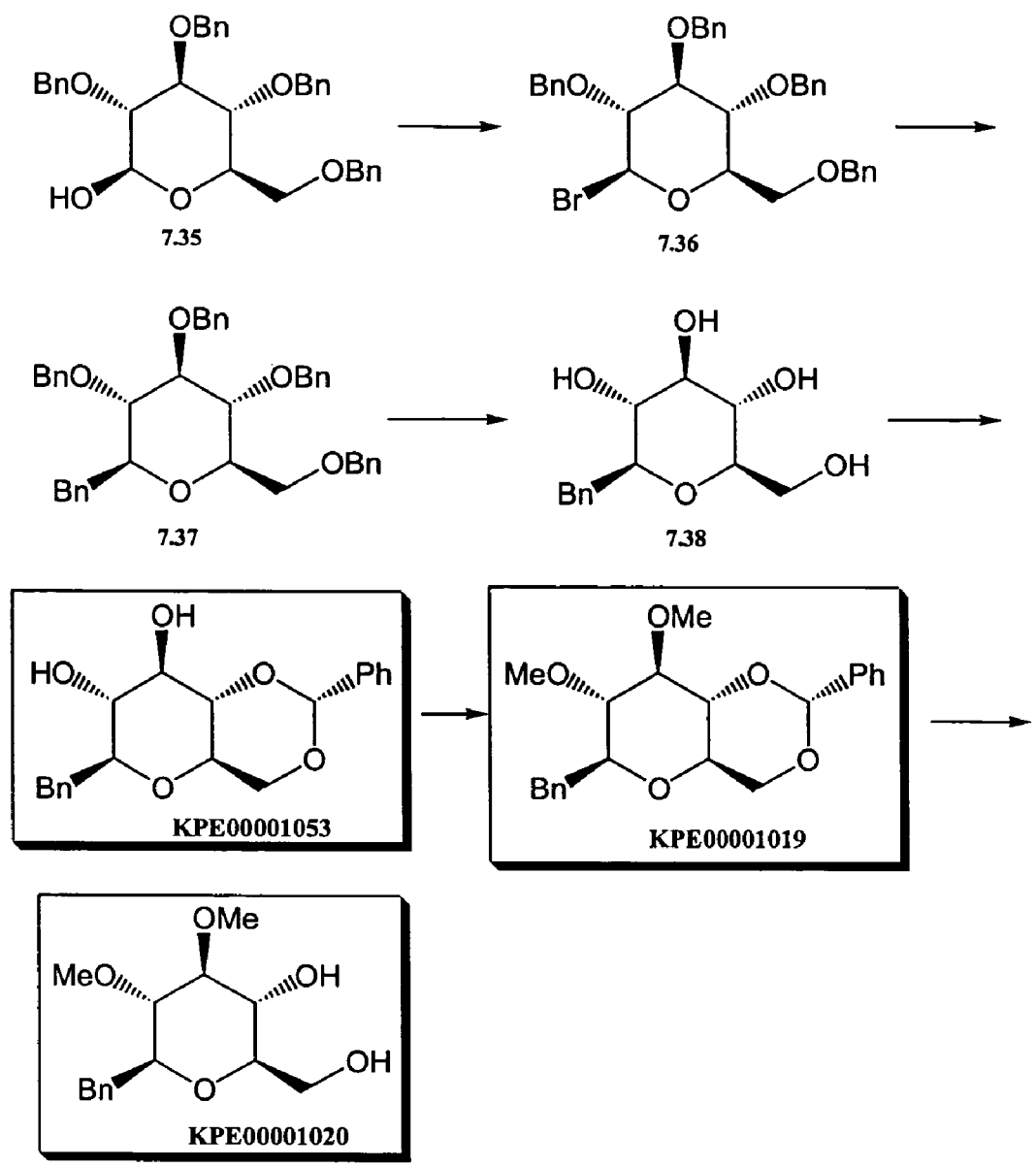
FIG. 20 is a diagrammatical representation of the synthesis scheme of macrolides KPE0000119, KPE00001020 through KPE00001053 of the present invention.

To methylene chloride (12 ml) were added slowly and simultaneously a solution of diene (Molecule 7.59) (120 mg, 0.195 mmol) in methylene chloride (12 ml) and a solution of the Grubbs' catalyst (40 mg, 0.05 mmol) in methylene chloride (12 ml). The mixture was stirred at room temperature for 18 hours. The solvent was then removed under reduced pressure. The crude products were purified by HPLC (eluent: cyclohexane/ethyl acetate 85/15) to yield 48 mg (43%) of KPE00001031E and 6 mg (5%) of KPE00001031Z (FIG. 17).

Compound KPE00001031E:
Formula: $C_{35}H_{54}O_7$
Molecular weight: 586.81
R$_f$: 0.36 (cyclohexane/ethyl acetate 8:2)
Melting point: 45-46° C.
$[\alpha]_D^{20}$=-6.1; $[\alpha]_{365}^{20}$=-5.8 (c=1.30 in chloroform)
IR(KBr): 2925, 2853, 2361, 2343, 1743, 1456, 1376, 1261, 1086, 1027, 958, 803, 701 cm$^{-1}$
ES-MS: 604=[586+NH$_4$]$^+$
$^1$H-NMR (500 MHz, CDCl3): 7.28 (4H, m), 7.22 (1H, m), 5.83 (1H, m), 5.81 (1H, m), 5.00 (2H, m), 4.94 (2H, m), 4.89 (1H, dd, app. t, J=9.7 Hz), 4.11 (1H, dd, J=12.1, 6.2 Hz), 4.03 (1H, dd, J=12.0, 2.4 Hz), 3.61 (3H, s), 3.54 (3H, s), 3.41 (1H, ddd, J=12.4, 6.1, 2.3 Hz), 3.35 (1H, ddd, J=11.3, 9.2, 2.2 Hz), 3.30 (1H, dd, app. t, J=9.1 Hz), 3.10 (1H, dd, J=14.3, 2.1 Hz), 3.00 (1H, dd, app. t, J=9.2 Hz), 2.75 (1H, dd, J=14.3, 8.8 Hz), 2.33 (2H, m), 2.24 (2H, m), 2.05 (4H, m), 1.60 (4H, m), 1.38 (4H, m), 1.29 (4H, m), 1.29 (4H, m), 1.29 (4H, m), 1.29 (4H, m)
$^{13}$C-NMR (125 MHz, CDCl3): 173.25, 172.24, 138.21, 130.68, 129.83, 129.48, 127.86, 126.02, 86.23, 82.80, 79.92, 75.32, 70.70, 63.20, 60.56, 60.30, 37.43, 34.15, 33.99, 31.91, 29.51, 29.21, 29.17, 29.06, 28.52, 28.31, 27.87, 27.71, 27.55, 26.71, 26.62, 26.38, 24.42

Compound KPE00001031Z:
Formula: $C_{35}H_{54}O_7$
Molecular weight: 586.81
R$_f$: 0.36 (cyclohexane/ethyl acetate 8:2)
Melting point: 84-85° C.
$[\alpha]_D^{20}$=+23.2; $[\alpha]_{365}^{20}$=+18.1 (c=0.47 in chloroform)
IR(KBr): 2919, 2850, 1741, 1654, 1468, 1387, 1244, 1183, 1102, 964, 752, 699 cm$^{-1}$
ES-MS: 604=[586+NH$_4$]$^+$
$^1$H-NMR (500 MHz, CDCl3): 7.28 (4H, m), 7.22 (1H, m), 5.83 (1H, m), 5.81 (1H, m), 5.00 (2H, m), 4.94 (2H, m), 4.89 (1H, dd, app. t, J=9.7 Hz), 4.11 (1H, dd, J=12.1, 6.2 Hz), 4.03 (1H, dd, J=12.0, 2.4 Hz), 3.61 (3H, s), 3.54 (3H, s), 3.41 (1H, ddd, J=12.4, 6.1, 2.3 Hz), 3.35 (1H, ddd, J=11.3, 9.2, 2.2 Hz), 3.30 (1H, dd, app. t, J=9.1 Hz), 3.10 (1H, dd, J=14.3, 2.1 Hz), 3.00 (1H, dd, app. t, J=9.2 Hz), 2.75 (1H, dd, J=14.3, 8.8 Hz), 2.33 (2H, m), 2.24 (2H, m), 2.05 (4H, m), 1.60 (4H, m), 1.38 (4H, m), 1.29 (4H, m), 1.29 (4H, m), 1.29 (4H, m), 1.29 (4H, m)
$^{13}$C-NMR (125 MHz, CDCl3): 173.27, 172.24, 138.22, 130.14, 129.68, 129.48, 127.83, 126.00, 86.22, 82.84, 79.81, 75.44, 70.11, 62.52, 60.55, 60.32, 37.40, 34.08, 33.82, 32.36, 29.52, 29.36, 29.04, 28.88, 27.00, 24.65, 24.48

EXAMPLE 43

Synthesis of KPE00001048

-D-1-Deoxy-1-phenylthio-glucopyranosyl tetraacetate (1.1)

To a solution of -D-glucose pentaacetate (150.0 g, 0.384 mol) in dry methylene chloride (1.65 l) were added thiophenol (43.5 ml, 0.423 mol) and tin(IV)chloride (50.0 ml, 0.268 mmol) at 0° C. The mixture was stirred at 0° C. for 15 minutes and at room temperature for 24 hours. Then it was diluted with methylene chloride (0.5 l), washed with a 1N hydrogen chloride solution (2×2 l), a saturated sodium bicarbonate solution (2×2 l) and brine (2×2 l). The organic layer was dried (MgSO$_4$), filtered and the solvent was removed under reduced pressure. The crude product was purified by recrystallization from dichloromethane/pentane to yield 1.1 (131.2 g, 78%) as a white solid.

Formula: $C_{20}H_{24}O_9S$

Molecular weight: 440.46

$R_f$: 0.31 (hexane/ethyl acetate 6/4)

Melting point: 113-114° C.

$[\alpha]_D^{20}$=−100.9; $[\alpha]_{365}^{20}$=−153.7 (c=1.12 in chloroform)

IR(KBr): 1749, 1477, 1437, 1369, 1226, 1087, 1036, 908, 826, 744, 687 cm$^{-1}$

ES-MS: 463=[440+Na]$^+$ $^1$H-NMR (500 MHz, CDCl$_3$): 7.49 (2H, m), 7.31 (3H, m), 5.22 (1H, dd, app.t, J=9.4 Hz), 5.04 (1H, dd, app.t, J=9.8 Hz), 4.97 (1H, dd, app.t, J=9.7 Hz), 4.70 (1H, d, J=10.1 Hz), 4.22 (1H, dd, J=12.3, 5.1 Hz), 4.18 (1H, dd, J=12.3, 2.5 Hz), 3.73 (1H, ddd, J=10.1, 5.1, 2.5 Hz), 2.09 (3H, s), 2.08 (3H, s), 2.01 (3H, s), 1.99 (3H, s)

$^{13}$C-NMR (125 MHz, CDCl$_3$): 170.41, 170.03, 169.25, 169.10, 133.04, 131.56, 128.82, 128.30, 85.65, 75.73, 73.89, 69.89, 68.17, 62.06, 20.59, 20.43

C,H-analysis: calculated: C 54.54%, H 5.49% found: C 54.56%, H 5.01%

-D-1-Deoxy-1-phenylthioglucopyranose (1.2)

-D-1-Deoxy-1-phenylthio-glucopyranosyl tetraacetate 1.1 (440.5 g, 0.346 mol) was dissolved in a mixture of tetrahydrofuran and methanol (1:1, 1800 ml). To this solution potassium carbonate (11.0 g, 0.079 mol) was added at room temperature. The mixture was stirred at room temperature for 5 hours and filtered over silicagel. The residue was washed with methylene chloride/methanol (1:1, 1000 ml) and the solvent was removed to yield 1.2 (94.0 g, 99%) as a white solid.

Formula: $C_{12}H_{16}O_5S$

Molecular weight: 272.31

$R_f$: 0.50 (dichloromethane/methanol 8/2)

Melting point: 104-105° C.

$[\alpha]_D^{20}$=−106.4; $[\alpha]_{365}^{20}$=−236.1 (c=1.30 in chloroform)

IR(KBr): 3405, 1583, 1480, 1439, 1274, 1024, 879, 819, 742, 691 cm$^{-1}$

ES-MS: 295=[272+Na]$^+$ $^1$H-NMR (500 MHz, CD$_3$OD): 7.56 (2H, m), 7.26 (3H, m), 4.59 (1H, d, J=9.8 Hz), 3.86 (1H, dd, J=12.0, 1.8 Hz), 3.38 (1H, dd, app.t, J=8.6 Hz), 3.30 (2H, m), 3.26 (1H, dd, J=12.0, 5.4 Hz), 3.21 (1H, dd, J=9.7, 8.7 Hz)

$^{13}$C-NMR (125 MHz, CDCl$_3$): 135.26, 132.75, 129.66, 128.32, 89.42, 82.05, 79.71, 73.79, 71.40, 62.70

C,H-analysis: calculated: C 52.93%, H 5.92% found: C 49.95%, H 5.54%

Benzylidene acetal 1.3 (KPE00001048)

To a solution of a -D-1-deoxy-1-phenylthioglucopyranose 1.2 (81.2 g, 0.298 mol) in dry dimethylformamide (325 ml) were added camphorsulfonic acid (17.3 g, 0.074 mol) and benzaldehyde dimethyl acetal (50.0 ml, 0.358 mol) at room temperature. The mixture was heated at 110° C. and stirred for 48 hours. The reaction mixture was cooled to room temperature, diluted with ethyl acetate (1000 ml), washed with a 1N sodium hydroxide solution (2×500 ml), a saturated sodium bicarbonate solution (2×500 ml) and brine (2×500 ml). The organic layer was dried (MgSO$_4$), filtered and the solvent was removed under reduced pressure. The crude product was purified by recrystallization from ethyl acetate/hexane to yield 1.3 (79.4 g, 74%) as a white solid.

Formula: $C_{19}H_{20}O_5S$

Molecular weight: 360.42

$R_f$: 0.16 (dichloromethane/methanol 98:2)

Melting point: 172-174° C.

$[\alpha]_D^{20}$=+27.8; $[\alpha]_{365}^{20}$=−60.4 (c=1.07 in chloroform)

IR(KBr): 3372, 2880, 1652, 1440, 1370, 1296, 1277, 1215, 1166, 1106, 1070, 1010, 986, 831, 743, 698, 654 cm$^{-1}$

ES-MS: 383=[360+Na]$^+$ $^1$H-NMR (500 MHz, CDCl$_3$): 7.52 (2H, m), 7.50 (2H, m), 7.32 (6H, m), 5.56 (1H, s), 4.70 (1H, d, J=9.8 Hz), 4.27 (1H, dd, J=10.3, 4.8 Hz), 3.76 (1H, dd, app. t, J=10.0 Hz), 3.65 (1H, dd, app.t, J=8.9, 8.7 Hz), 3.50 (1H, dd, app.t, J=9.7, 4.9 Hz), 3.43 (2H, m)

$^{13}$C-NMR (125 MHz, CDCl$_3$): 136.78, 132.95, 131.26, 129.21, 129.01, 128.34, 128.24, 126.17, 101.72, 88.49, 80.11, 74.50, 72.53, 70.45, 66.47

C,H-analysis: calculated: C 63.32%, H 5.59% found: C 62.14%, H 5.29%

EXAMPLE 44

Synthesis of -D-1-deoxy-1-phenylthioglucopyranose benzylidene acetal Derivatives Diallylether 2.1 (KPE0001046)

A solution of 1.3 (218 mg, 0.605 mmol) in dry dimethylformamide (3 ml) was cooled to 0° C. and pure NaH (56 mg, 2.3 mmol) was added. This mixture was stirred at 0° C., and after 10 min allyl bromide (118 l, 1.364 mmol) was added dropwise. After 5 min at 0° C., the reaction mixture was allowed to reach room temperature. The reaction mixture was stirred at room temperature for 1.5 h. Next, the reaction was quenched by adding MeOH (1 ml). Distilled water and ether were added, followed by separation of the two layers. The aqueous layer was extracted with 3×20 ml of ether. The combined organic layers were dried (MgSO$_4$), concentrated under reduced pressure and further dried in vacuo. Purification of the crude product (325 mg) by recrystallization from ethanol yielded 2.1 (190 mg, 71%) as a clear white solid.

Formula: $C_{25}H_{28}O_5S$

Molecular weight: 440.55

$R_f$: 0.66 (cyclohexane/ethyl acetate 1/1)

Melting point: 111-113° C.

$[\alpha]_D^{20}$=−50.8 ; $[\alpha]_{365}^{20}$=−146.6 (c=0.99 in dichloromethane)

IR (KBr): 3067, 3015, 2985, 2903, 2879, 1641, 1586, 1481, 1370, 1345, 1273, 1149, 1088, 1031, 994, 964, 927, 750, 734, 697 cm$^{-1}$

MS (m/z): 41 (100), 81 (27), 149 (4), 203 (2), 273 (2), 331 (1), 383 (<1), [M−57], 440 (<1) [M+]

$^1$H-NMR (500 MHz, CDCl$_3$): 7.53 (2H, m), 7.50 (2H, m), 7.35 (6H, m), 5.98 (2H, m), 5.55 (1H, s), 5.30 (2H, dd, app. t., J=15.7 Hz), 5.18 (2H, dd, J=17.1 Hz, 10.4 Hz), 4.68 (1H, d, J=9.8 Hz), 4.36 (4H, m), 4.25 (1H, dd, J=12.5 Hz, 5.8 Hz), 3.78 (1H, dd, app. t., J=10.2 Hz), 3.65 (1H, dd, app. t., J=9.1 Hz, 8.4 Hz), 3.60 (1H, dd, app. t., J=9.1 Hz, 9.3 Hz), 3.43 (1H, m), 3.34 (1H, dd, app. t., J=8.5 Hz, 9.4 Hz)

$^{13}$C-NMR (125 MHz, CDCl$_3$): 137.31, 135.00, 134.78, 133.21, 132.32, 129.04, 128.30, 127.87, 126.04, 117.42, 117.12, 101.17, 88.28, 82.60, 81.20, 80.21, 74.80, 74.17, 70.32, 68.73

Diethyl ether 2.3 (KPE00001050)

A solution of 1.3 (220 mg, 0.610 mmol) in dry dimethylformamide (3 ml) was cooled to 0° C., and pure sodium hydride (59 mg, 2.44 mmol) was added. The reaction mixture was stirred at 0° C., and after 10 min, ethyl bromide (105 l, 1.403 mmol) was added dropwise. The mixture was stirred at 0° C. under argon atmosphere for another 10 min and was then allowed to reach room temperature while stirring overnight. The reaction was quenched by adding MeOH (1 ml) and the reaction mixture was concentrated in vacuo. Water and Et$_2$O were added, the layers were separated and the aqueous layer was extracted with Et$_2$O (3 ×25 ml). The combined organic layers were washed with brine (50 ml) and dried over MgSO$_4$. After filtration, the solvent was removed in vacuo, and the residue (235 mg) was purified by column chromatography (230-400 mesh silica; cyclohexane/ethyl acetate 92/8), yielding 2.3 as a white solid (192 mg, 76%)

Formula: C$_{23}$H$_{28}$O$_5$S
Molecular weight: 416.54
R$_f$: 0.68 (cyclohexane/ethyl acetate 1/1)
Melting point: 135-136° C.
$[\alpha]_D^{20}$=−45.8; $[\alpha]_{365}^{20}$=−133.5 (c=1.03 in chloroform)
IR (KBr): 3060, 2972, 2898, 1585, 1480, 1383, 1370, 1362, 1339, 1273, 1170, 1084, 1077, 1030, 994, 962, 916, 737, 696
ES-MS: (m/z) 439 [M+Na+]

$^1$H-NMR (500 MHz, CDCl$_3$): 7.53 (2H, m), 7.48 (2H, m), 7.33 (6H, m), 5.55 (1H, s), 4.66 (1H, d, J=9.8 Hz), 4.35 (1H, dd, J=10.5 Hz, 5.0 Hz), 3.92 (1H, m), 3.86 (2H, dq, J=7.1 Hz, 1.9 Hz), 3.78 (2H, m), 3.54 (2H, m), 3.42 (1H, m), 3.24 (1H, m), 1.26 (3H, t, J=7.0 Hz), 1.22 (3H, t, J=7.1 Hz)

$^{13}$C-NMR (125 MHz, CDCl$_3$): 137.12, 133.46, 132.17, 129.00, 128.97, 128.27, 127.74, 126.05, 101.13, 88.45, 83.12, 81.10, 80.89, 70.42, 69.46, 68.87, 68.74, 15.82

Dibenzyl Ether (KPE00001044)

To a solution of diol KPE00001048 (5.0 g, 13.8 mmol) in tetrahydrofuran (60 ml) was added at 0° C. sodiumhydride (1.67 g, 69.36 mmol). The mixture was stirred at 0° C. for 30 minutes and benzylbromide (5.5 ml, 45.78 mmol) was added. The suspension was allowed to warm up to room temperature and tetrabutylammonium iodide (11.2 g, 30.36 mmol) was added. The mixture was stirred at room temperature for 48 hours and then poured into ice water (100 ml). The two layers were separated and the water layer was extracted with diethylether (2×100 ml). The combined organic layers were dried (MgSO$_4$), filtered and the solvent was removed under reduced pressure. The crude product 7.1 was purified by recrystallization from methylene chloride and hexane to yield 4.23 g (57%) of a white solid KPE00001044.

Formula: C$_{33}$H$_{32}$O$_5$S
Molecular weight: 540.67
R$_f$: 0.62 (cyclohexane/ethyl acetate 1:1)
Melting point: 143-144° C.
$[\alpha]_D^{20}$=−92.0; $[\alpha]_{365}^{20}$=−128.7 (c=1.28 in chloroform)
IR(KBr): 2869, 2364, 1584, 1497, 1453, 1366, 1272, 1091, 1028, 748, 697, 657 cm$^{-1}$
ES-MS: 563=[540+Na]+

$^1$H-NMR (500 MHz, CDCl$_3$): 7.55 (2H, m), 7.50 (2H, m), 7.41 (3H, m), 7.38 (3H, m), 7.36 (2H, m), 7.34 (2H, m), 7.32 (3H, m), 7.31 (3H, m), 5.60 (1H, s), 4.95 (1H, d, J=11.1 Hz), 4.87 (1H, d, J=10.3 Hz), 4.84 (1H, d, J=10.2 H), 4.80 (1H, d, J=6.9 Hz), 4.78 (1H, d, J=10.0 Hz), 4.40 (1H, dd, J=10.5, 5.5 Hz), 3.85 (1H, dd, J=9.7 Hz), 3.82 (1H, dd, app. t, J=10.0 Hz), 3.72 (1H, dd, J=10.0 Hz), 3.52 (1H, dd, J=9.7 Hz), 3.48 (1H, ddd, J=14.6, 9.8, 5.1 Hz)

$^{13}$C-NMR (125 MHz, CDCl$_3$): 138.14, 137.87, 137.10, 132.94, 132.21, 128.88, 128.27, 128.13, 128.09, 127.99, 127.75, 127.65, 125.85, 100.99, 88.13, 82.87, 81.31, 80.30, 75.77, 75.19, 70.10, 68.56

C,H-analysis: calculated: C 73.31%, H 5.97%
found: C 72.92%, H 6.13%

Dimethyl ether (KPE00001045)

To a solution of diol KPE00001048 (12.1 g, 0.034 mol) in dry dimethyl ethylene glycol (150 ml) was added sodium hydride (4.0 g, 0.167 mol) at 0° C. The suspension was stirred at 0° C. for 30 minutes. Iodomethane (7 ml, 0.112 mol) was added at 0° C. and the mixture was stirred at room temperature for 24 hours. Then the mixture was poured into ice water and extracted with diethylether (3×200 ml). The combined organic layers were dried (MgSO$_4$), filtered and the solvent was removed under reduced pressure. The crude product was purified by recrystallization from methylene chloride/hexane to yield a white solid KPE00001045 (8.9 g, 98%).

Formula: C$_{21}$H$_{24}$O$_5$S
Molecular weight: 388.48
R$_f$: 0.66 (hexane/ethyl acetate 1:1)
Melting point: 136-137° C.
$[\alpha]_D^{20}$=−345.8; $[\alpha]_{365}^{20}$=−435.3 (c=1.11 in chloroform)
IR(KBr): 1642, 1584, 1499, 1481, 1450, 1407, 1371, 1330, 1276, 1173, 1120, 1094, 1078, 1035, 995, 956, 833, 740, 694, 654 cm$^{-1}$
ES-MS; 389=[388+H]+; 406=[388+NH$_4$]+; 427=[388+K]+

$^1$H-NMR (500 MHz, CDCl$_3$): 7.53 (2H, m), 7.48 (2H, m), 7.36 (3H, m), 7.31 (3H, m), 5.54 (1H, s), 4.63 (1H, d, J=9.7 Hz), 4.35 (1H, dd, J=10.5, 5.0 Hz), 3.78 (1H, dd, apt.t, J=10.3, 10.2 Hz), 3.65 (3H, s), 3.64 (3H, s), 3.56 (1H, dd, apt.t, J=9.4, 9.3 Hz), 3.44 (1H, dd, apt.t, J=9.2, 8.4 Hz), 3.43 (1H, ddd, J=9.8, 9.7, 5.0 Hz), 3.12 (1H, dd, J=9.7, 8.3 Hz)

$^{13}$C-NMR (125 MHz, CDCl$_3$): 137.17, 132.97, 132.20, 128.85, 128.11, 127.70, 125.95, 101.09, 87.87, 84.71, 82.16, 81.09, 70.07, 68.58, 61.14, 60.88

C,H-analysis: calculated: C 64.93%, H 6.23, S 8.25%
found: C 64.77%, H 6.15, S 8.66%

EXAMPLE 45

Synthesis of diol 7.2

To a suspension of acetal KPE00001044 (1.0 g, 1.85 mmol) in methanol (20 ml) was added at room temperature camphorsulfonic acid (214 mg, 0.925 mmol). The mixture was stirred at room temperature for 48 hours. Triethylamine (3 ml) was added and the solvent was removed under reduced pressure. The crude product was purified by flash chromatography (eluens: cyclohexane/ethyl acetate 1/1) to yield 814 mg (97%) of a white solid 7.2.

Formula: $C_{26}H_{28}O_5S$
Molecular weight: 452.56
$R_f$: 0.30 (cyclohexane/ethyl acetate 1:1)
Melting point: 91-92° C.
$[\alpha]_D^{20}$=+29.5; $[\alpha]_{365}^{20}$=+105.3 (c=1.12 in chloroform)
IR(KBr): 3332, 3061, 3029, 2873, 2360, 1584, 1497, 1480, 1454, 1439, 1399, 1353, 1278, 1212, 1126, 1062, 1027, 911, 815, 738, 697, 635, 580, 530, 461 cm$^{-1}$
ES-MS: 475=[452+Na]$^+$
$^1$H-NMR (500 MHz, CDCl$_3$): 7.53 (2H, m), 7.51 (2H, m), 7.42 (2H, m), 7.38 (3H, m), 7.36 (3H, m), 7.33 (3H, m), 7.32 (3H, m), 4.97 (1H, d, J=2.6 Hz), 4.95 (1H, s), 4.73 (3H, m), 3.88 (1H, m), 3.75 (1H, m), 3.58 (1H, dd, J=9.2, 2.3 Hz), 3.53 (1H, t, J=8.6 Hz), 3.49 (1H, t, J=8.6 Hz), 3.36 (1H, ddd, J=9.0, 6.0, 1.8 Hz), 2.28 (1H, d, J=2.5 Hz), 2.04 (1H, t, J=6.6 Hz)
$^{13}$C-NMR (125 MHz, CDCl$_3$): 138.16, 137.65, 133.39, 131.62, 128.95, 128.61, 128.37, 128.16, 127.99, 127.88, 127.79, 127.58, 87.62, 85.92, 80.75, 79.00, 75.31, 75.31, 70.28, 62.62
C,H-analysis: calculated: C 69.00%, H 6.20%
found: C 68.73%, H 5.95%

Synthesis KPE00001011

To a suspension of the benzylidene acetal KPE00001045 (10.4 g, 26.720 mmol) in methanol (175 ml) was added camphorsulfonic acid (2.1 g, 8.817 mmol). The mixture was stirred at room temperature for 24 hours. Triethylamine (2 ml) was added and the solution was concentrated to a volume of 100 ml. The residue was diluted with methylene chloride (200 ml) and filtered over silicagel. The filter was washed with methylene chloride and methanol (1:1, 3×50 ml) and the solvent was removed under reduced pressure. The crude product was purified by recrystallization from methylene chloride/pentane to yield a white solid KPE00001011 (8.0 g, 99%).

Formula: $C_{14}H_{20}O_5S$
Molecular weight: 300.37
$R_f$: 0.08 (hexane/ethyl acetate 1:1)
Melting point: 145-146° C.
$[\alpha]_D^{20}$=−80.7; $[\alpha]_{365}^{20}$=−206.6 (c=1.00 in chloroform)
IR(KBr): 3405, 2935, 1738, 1584, 1480, 1445, 1285, 1190, 1142, 1107, 1060, 1024, 954, 871, 742, 692, 614 cm$^{-1}$
ES-MS ; 323=[300+Na]$^+$
$^1$H-NMR (500 MHz, CDCl$_3$): 7.50 (2H, m), 7.29 (3H, m), 4.60 (1H, d, J=9.7 Hz), 3.89 (1H, m), 3.76 (1H, m), 3.67 (3H, s), 3.62 (3H, s), 3.50 (1H, m), 3.32 (1H, m), 3.19 (1H, dd, app. t, J=8.9 Hz), 3.08 (1H, dd, app. t, J=9.0 Hz)
$^{13}$C-NMR (125 MHz, CDCl$_3$):133.34, 131.69, 128.89, 127.54, 87.77, 87.35, 82.66, 78.93, 70.28, 62.87, 61.04, 60.49
C,H-analysis: calculated: C 55.98%, H 6.71, S 10.68%
found: C 55.70%, H 6.57, S 10.66%

EXAMPLE 46

Synthesis of -D-1-allyl-1-deoxy-glucopyranose benzylidene acetal Derivatives

-D-2,3,4,6-Tetra-O-acetyl-glucopyranosyl bromide 3.1

To -D-glucose pentaacetate a solution of HBr (33 wt % in acetic acid) was added. A dark golden color appeared. The reaction mixture was stirred at room temperature under argon atmosphere for 30 min. Next the solvent was removed in vacuo, to yield 3.1 as a sticky orange residue. This residue was used in the next reaction step without further purification.

-D-1-Allyl-1-deoxy-glucopyranose tetraacetate 3.2

A solution of allylmagnesium bromide (25.6 mmol) in Et$_2$O (60 ml) was cooled to 0° C. and a solution of bromide 3.1 (1.05 g theoretical mass, 2.56 mmol) in Et$_2$O (15 ml) was added dropwise via a canula. The green color observed in the allylmagnesium bromide solution disappeared directly after addition of 3.1, and solid white particles were formed. The reaction mixture was stirred at room temperature under argon atmosphere for 23 h. Next the reaction was quenched by adding water (100 ml) and acetic acid (10 ml). The layers were separated and the organic layer was extracted with water (3 ×30 ml). The combined aqueous layers were concentrated in vacuo to obtain a solid greasy residue. This residue was dissolved in pyridine (25 ml) and acetic anhydride (20 ml). The mixture was stirred overnight at room temperature. The solvent was removed under reduced pressure and ethyl acetate and saturated NaHCO$_3$-solution were added. After separation of both layers, the organic phase was washed with a 1N HCl-solution and brine. The organic layer was dried (MgSO$_4$) and concentrated in vacuo. The residue was purified by column chromatography (230-400 silica; cyclohexane/ethyl acetate 75/25), yielding 3.2 (482 mg) as a white solid. An impure fraction was further purified by column chromatography (230-400 mesh silica; cyclohexane/ethyl acetate 8/2). This second purification yielded another 124 mg of 3.2 (total yield: 63.6% from the pentaacetate).

Formula: $C_{17}H_{24}O_9$
Molecular weight: 372.37
$R_f$: 0.46 (cyclohexane/ethyl acetate 1/1)
Melting point: 70-72° C.
$[\alpha]_D^{20}$=−7.7; $[\alpha]_{365}^{20}$=−21.5 (c=1.01 in chloroform)
IR (KBr): 3085, 2951, 2869, 1754, 1644, 1434, 1367, 1225, 1101, 1033, 981, 906
MS: (m/z) 43 (100), 109 (4), 137 (3), 169 (3), 331 (<1) [M-41]
$^1$H-NMR (500 MHz, CDCl$_3$): 5.81 (1H, m), 5.16 (1H, dd, app. t., J=9.4 Hz), 5.05 (3H, m), 4.91 (1H, dd, app. t., J=9.6 Hz, 9.5 Hz), 4.23 (1H, dd, J=12.3 Hz, 5.0 Hz), 4.09 (1H, dd, J=12.3 Hz, 2.3 Hz), 3.62 (1H, ddd, J=10.0 Hz, 5.0 Hz, 2.3 Hz), 3.49 (1H, ddd, J=11.2 Hz, 7.2 Hz, 4.2 Hz), 2.28 (2H, m), 2.07 (3H, s), 2.02 (3H, s), 2.01 (3H, s), 1.99 (3H, s)
$^{13}$C-NMR (125 MHz, CDCl$_3$): 170.76, 170.49, 169.61, 169.55, 133.00, 117.74, 76.83, 75.67, 74.44, 71.68, 68.68, 62.34, 35.88, 20.81, 20.78, 20.70, 20.67

-D-1-Allyl-1-deoxy-glucopyranose (3.3)

To a solution of 3.2 (400 mg, 1.074 mmol) in THF (5 ml) and MeOH (5 ml), anhydrous K$_2$CO$_3$ (37 mg, 0.25 eq) was added. The reaction mixture was stirred overnight at room temperature. Next, the reaction mixture was concentrated under reduced pressure. The residue was purified by column chromatography (230-400 mesh silica; dichloromethane/methanol 85/15), yielding 3.3 (227 mg, >100%) as a yellow oil.

Formula: $C_9H_{16}O_5$
Molecular weight: 204.22
$R_f$: 0.26 (dichloromethane/methanol 85/15)
$[\alpha]_D^{20}$=−12.2; $[\alpha]_{365}^{20}$=−17.8 (c=0.55 in methanol)
IR (KBr): 3354, 2916, 2840, 1642, 1414, 1362, 1086, 1046, 1004, 917, 837
ES-MS: (m/z) 227 [M+Na$^+$]

$^1$H-NMR (500 MHz, CD$_3$OD): 5.97 (1H, ddt, J=17.2 Hz, 10.3 Hz, 6.9 Hz), 5.11 (1H, ddd, J=17.2 Hz, 3.5 Hz, 1.5 Hz), 5.02 (1H, dd, app. dt, J=10.2 Hz, 3.5 Hz), 3.83 (1H, dd, J=11.9 Hz, 2.3 Hz), 3.62 (1H, dd, J=11.9 Hz, 5.7 Hz), 3.32 (1H, m), 3.24 (1H, dd, app. t., J=9.5 Hz, 8.7 Hz), 3.19 (2H, m), 3.09 (1H, dd, app. t., J=9.1 Hz), 2.58 (1H, ddt, J=14.7 Hz, 6.9 Hz, 1.4 Hz), 2.22 (1H, ddt, J=14.7 Hz, 6.9 Hz, 0.9 Hz)

$^{13}$C-NMR (125 MHz, CD$_3$OD): 134.99, 115.61, 80.29, 79.26, 78.48, 73.51, 70.60, 61.73, 35.70

Benzylidene acetal 3.4 (KPE00001049)

To a solution of 3.3 (200 mg, 0.979 mmol) in dry dimethylformamide (1 ml) were added camphorsulfonic acid (57 mg, 0.245 mmol) and benzaldehyde dimethyl acetal (221 l, 1.469 mmol). The reaction mixture was stirred under argon atmosphere at room temperature and after 15 min the temperature was gradually raised to 110° C. After 19 h another 57 mg of CSA and 221 l of benzaldehyde dimethyl acetal were added to the reaction mixture, which was further stirred at 110° C. for 3 hours. The reaction was quenched with 1 ml NH$_3$ in H$_2$O, and concentrated in vacuo. Purification by column chromatography (230-400 mesh silica; cyclohexane/ethyl acetate 6/4), yielded 3.4 (146 mg, 51%) as a white solid.

Formula: C$_{16}$H$_{20}$O$_5$
Molecular weight: 292.33
R$_f$: 0.75 (dichloromethane/methanol 9/1)
Melting point: 122-123° C.
$[\alpha]_D^{20}$=−27.8; $[\alpha]_{365}^{20}$=−83.2 (c=0.76 in chloroform)
IR (KBr): 3406, 3071, 2977, 2872, 1642, 1457, 1385, 1314, 1297, 1267, 1215, 1161, 1100, 1008, 916, 762, 699 cm$^{-1}$
MS: (m/z) 41 (95), 73 (85), 105 (100), 127 (12), 158 (12), 221 (4) [M-71], 251 (5) [M-41], 292 (15) [M$^+$]
$^1$H-NMR (500 MHz, CDCl$_3$): 7.49 (2H, m), 7.38 (3H, m), 5.88 (1H, ddt, J=17.1 Hz, 10.2 Hz, 6.9 Hz), 5.50 (1H, s), 5.14 (1H, dd, J=17.2 Hz, 1.8 Hz), 5.07 (1H, dd, J=10.2 Hz, 1.8 Hz), 4.31 (1H, dd, J=10.3 Hz, 4.5 Hz), 3.69 (2H, m), 3.4 (4H, m), 3.21 (1H, br. s), 2.58 (1H, m), 2.27 (1H, m), 1.76 (1H, br. s)
$^{13}$C-NMR (125 MHz, CDCl$_3$): 137.12, 134.14, 129.39, 129.09, 128.45, 127.04, 126.34, 117.53, 101.89, 81.137, 79.29, 75.31, 73.94, 70.24, 68.93, 62.41, 36.09

Dimethyl ether 3.5 (KPE00001051)

A solution of 3.4 (97 mg, 0.332 mmol) in dry dimethylformamide (3.2 ml) was cooled to 0° C. and pure NaH (32 mg, 1.33 mmol) was added. After stirring the reaction mixture at 0° C. for 35 min, MeI (104 l, 1.66 mmol) was added dropwise. The reaction mixture was stirred at 0° C. for another 5 min and was then allowed to reach room temperature while stirring overnight. The reaction was quenched by pouring out the mixture in water (25 ml). Et$_2$O was added, both layers were separated and the aqueous layer was extracted with Et$_2$O (3×25 ml). The combined organic layers were washed with brine (25 ml), and dried over MgSO$_4$. After filtration, the solvent was removed in vacuo and the resulting white residue was purified by column chromatography (230-400 mesh silica; cyclohexane/ethyl acetate 92/8), yielding 3.5 (90 mg, 85%) as a white solid.

Formula: C$_{18}$H$_{24}$O$_5$
Molecular weight: 320.38
R$_f$: 0.60 (cyclohexane/ethyl acetate 6/4)
Melting point: 105-107° C.
$[\alpha]_D^{20}$=−35.5 ; $[\alpha]_{365}^{20}$=−101.1 (c=1.01 in chloroform)
IR (KBr): 2982, 2929, 2879, 2831, 1450, 1389, 1375, 1339, 1278, 1122, 1092, 1036, 996, 976, 922, 754, 699 cm$^{-1}$
MS: (m/z) 45 (85), 77 (77), 105 (100), 145 (10), 173 (3), 191 (5), 279 (9) [M-41], 320 (5) [M$^+$]
$^1$H-NMR (500 MHz, CDCl$_3$): 7.50 (2H, m), 7.37 (3H, m), 5.88 (1H, ddt, J=17.2 Hz, 10.2 Hz, 7.0 Hz), 5.54 (1H, s), 5.12 (2H, m), 4.32 (1H, dd, J=10.4 Hz, 5.0 Hz), 3.68 (1H, dd, app. t., J=10.3 Hz), 3.66 (3H, s), 3.59 (3H, s), 3.51 (1H, dd, app. t., J=9.2 Hz), 3.44 (1H, dd, app.t., J=8.4 Hz), 3.36 (2H, m), 2.99 (1H, dd, J=9.5 Hz, 8.5 Hz), 2.57 (1H, m), 2.28 (1H, m)
$^{13}$C-NMR (125 MHz, CDCl$_3$): 137.50, 134.36, 128.96, 128.28, 126.08, 117.37, 101.11, 85.04, 82.89, 82.26, 79.27, 70.20, 68.99, 60.98, 60.85, 36.16

EXAMPLE 47

Synthesis of KPE00001015

Bromide 7.27

To (β)-D-glucose pentaacetate 4.1 (12.0 g, 30.74 mmol) was added a solution of hydrogenbromide in acetic acid (33 wt %, 50 ml) at room temperature. The solution turned dark brown. The mixture was stirred at room temperature for 30 minutes. The solvent was removed under reduced pressure to yield a brown solid 7.27 (14.03 g, 99%). This product was used without purification in the next step.

Formula: C$_{14}$H$_{19}$O$_9$Br
Molecular weight: 411.20
R$_f$: 0.46 (cyclohexane/ethyl acetate 1:1)
IR(KBr): 2962, 2360, 2342, 1748, 1435, 1369, 1218, 1162, 1112, 1079, 1042, 911, 752, 668, 601, 563 cm$^{-1}$
ES-MS: 433=[411+Na]$^+$
$^1$H-NMR (500 MHz, CDCl$_3$): 6.61 (1H, d, J=4.0 Hz), 5.56 (1H, dd, app. t, J=9.7 Hz), 5.16 (1H, dd, app. t, J=9.7 Hz), 4.84 (1H, dd, J=10.0, 4.0 Hz), 4.33 (1H, m), 4.30 (1H, m), 4.13 (1H, dd, J=12.3, 1.5 Hz), 2.11 (3H, s), 2.10 (3H, s), 2.05 (3H, s), 2.03 (3H, s)
$^{13}$C-NMR (125 MHz, CDCl$_3$): 170.37, 169.70, 169.64, 169.31, 86.34, 71.91, 70.39, 69.94, 66.94, 60.76, 20.48, 20.48, 20.38, 20.38

Grignard Reaction 7.28

To a solution of phenylmagnesiumbromide (291 mmol, 97 ml of a 3M solution in diethylether) in dry diethylether (250 ml) was added at 0° C. a solution of bromide 7.27 (12.64 g, 30.740 mmol) in dry diethylether (250 ml) via a double-tipped needle. The reaction was stirred at room temperature for 48 hours. Then the mixture was poured into water (1000 ml) and acetic acid (100 ml) was added. The two layers were separated and the organic layer was washed with water (3×250 ml). The water layers were combined and the water was removed under reduced pressure to a brown solid. This product was then dissolved in pyridine (250 ml) and acetic acid (170 ml) was added. After stirring for 10 minutes a brown precipitate was formed. The mixture was stirred at room temperature for another 24 hours and poured into water (1800 ml). The brown precipitate was filtered and recrystallized from 2-propanol to yield a slightly brown colored product 7.28 (5.7 g, 45%).

Formula: C$_{20}$H$_{24}$O$_9$
Molecular weight: 408.40
R$_f$: 0.42 (cyclohexane/ethyl acetate 1:1)
Melting point: 149-150° C.
IR(KBr): 2956, 1753, 1433, 1368, 1224, 1104, 1036, 978, 916, 764, 738, 702, 603 cm$^{-1}$
ES-MS: 431=[408+Na]$^+$ ¹H-NMR (500 MHz, CDCl₃): 7.39 (5H, m), 5.24 (1H, dd, app. t, J=9.4 Hz), 5.24 (1H, dd, app. t, J=9.8 Hz), 5.14 (1H, dd, app. t, J=9.8 Hz), 4.40 (1H, d, J=9.9 Hz), 4.30 (1H, dd, J=17.2, 4.7 Hz), 4.16 (1H, dd, J=12.2, 1.5 Hz), 3.85 (1H, m), 2.09 (3H, s), 2.06 (3H, s), 2.01 (3H, s), 1.80 (3H, s)

¹³C-NMR (125 MHz, CDCl₃): 170.60, 170.25, 169.36, 168.70, 136.01, 128.75, 128.28, 126.96, 80.08, 75.94, 74.06, 72.44, 68.39, 62.17, 20.61, 20.48, 20.21

Deprotection 7.29

To a suspension of tetraacetate 7.28 (5.7 g, 13.960 mmol) in tetrahydrofuran (60 ml) and methanol (60 ml) was added (di)potassium carbonate at room temperature. The mixture was stirred at room temperaure for 18 hours. Silicagel (10 g) was added and the solvent was removed under reduced pressure. The crude product was purified by flash chromatography (gradient elution: methylene chloride/methanol 1/0 to 9/1) to yield 3.31 g (99%) of product 7.29.

Formula: $C_{12}H_{16}O_5$
Molecular weight: 240.26
$R_f$: 0.12 (dichloormethane/methanol 9:1)
IR(KBr): 3368, 2919, 2360, 1636, 1496, 1455, 1082, 1042, 891, 764, 701, 595 cm⁻¹
ES-MS: 258=[240+NH₄]⁺, 263=[240+Na]⁺

¹H-NMR (500 MHz, CDCl₃): 7.44 (2H, d, J=7.1 Hz), 7.35 (2H, dd, app. t, J=7.6 Hz), 7.30 (1H, m), 4.15 (1H, d, J=9.4 Hz), 3.90 (1H, dd, J=12.1, 1.6 Hz), 3.72 (1H, dd, J=12.0, 5.2 Hz), 3.51 (1H, dd, app. t, J=8.7 Hz), 3.45 (1H, dd, app. t, J=9.4 Hz), 3.43 (3H, m), 3.43 (3H, m), 3.40 (1H, dd, app. t, J=9.2 Hz)

¹³C-NMR (125 MHz, CDCl₃): 139.30, 127.43, 82.41, 80.70, 78.23, 74.98, 70.40, 61.41

Benzylidene acetal KPE00001052

To a solution of tetrol 7.29 (70 mg, 0.291 mmol) in dimethylformamide (3 ml) were added at room temperature camphorsulfonic acid (20 mg, 0.087 mmol) and benzaldehyde dimethyl acetal (0.06 ml, 0.437 mmol). The mixture was stirred at room temperature for 5 hours. It was then diluted with ethyl acetate (17 ml), washed with a 1M sodiumhydroxide solution (2×20 ml), a saturated sodium bicarbonate solution (2×20 ml) and brine (2×20 ml). The organic layer was dried (MgSO₄), filtered and the solvent was removed under reduced pressure. The crude product was purified by flash chromatography (eluent: cyclohexane/ethyl acetate 1/1) to yield 88 mg (92%) of a white solid KPE00001052.

Formula: $C_{19}H_{20}O_5$
Molecular weight: 328.36
$R_f$: 0.27 (cyclohexane/ethyl acetate 1:1)
Melting point: 114-115° C.
$[\alpha]_D^{20}$=+9.3; $[\alpha]_{365}^{20}$=+10.0 (c=1.13 in chloroform)
IR(KBr): 3433, 2874, 2357, 1651, 1496, 1455, 1385, 1313, 1272, 1211, 1109, 1029, 1009, 913, 765, 733, 700 cm⁻¹
ES-MS: 346=[328+NH₄]⁺

¹H-NMR (500 MHz, CDCl₃): 7.53 (2H, m), 7.40 (5H, m), 7.39 (3H, m), 5.59 (1H, s), 4.37 (1H, dd, J=10.3, 5.9 Hz), 4.30 (1H, d, J=9.3 Hz), 3.91 (1H, dd, app. t, J=8.6 Hz), 3.79 (1H, dd, app. t, J=10.3 Hz), 3.67 (1H, dd, app. t, J=9.3 Hz), 3.65 (1H, m), 3.63 (1H, m)

¹³C-NMR (125 MHz, CDCl₃): 137.50, 136.84, 129.14, 128.65, 128.52, 128.20, 127.29, 126.12, 101.73, 82.41, 80.90, 75.43, 74.60, 70.60, 68.70

C,H-analysis: calculated: C 69.50%, H 6.14%
found: C 70.79%, H 6.11%

Dimethyl ether KPE00001015

To a solution of diol KPE00001052 (2.5 g, 7.6 mmol) in dry dimethyl ethylene glycol (80 ml) was added at 0° C. sodium-hydride (913 mg, 22.850 mmol). This mixture was stirred at 0° C. for 30 minutes. Iodomethane (1.6 ml, 25.12 mmol) was added at 0° C. and the mixture was stirred at room temperature for 2 hours. The reaction mixture was then poured into water (170 ml), the two layers were separated and the water layer was extracted with diethylether (3×350 ml). The combined organic layers were dried (MgSO₄), filtered and the solvent was removed under reduced pressure to yield 3.0 g (99%) of a yellow solid KPE00001015.

Formula: $C_{21}H_{24}O_5$
Molecular weight: 356.42
$R_f$: 0.59 (cyclohexane/ethyl acetate 8:2)
Melting point: 97-98° C.
$[\alpha]_D^{20}$=−21.0; $[\alpha]_{365}^{20}$=−67.0 (c=0.80 in chloroform)
IR(KBr): 3035, 2925, 2851, 2360, 1497, 1455, 1378, 1276, 1173, 1104, 1030, 999, 959, 916, 765, 699 cm⁻¹
ES-MS: 357=[356+H]⁺

¹H-NMR (500 MHz, CDCl₃): 7.53 (2H, m), 7.40 (3H, m), 7.38 (5H, m), 5.60 (1H, s), 4.37 (1H, dd, J=10.4, 4.9 Hz), 4.26 (1H, d, J=9.5 Hz), 3.78 (1H, dd, app. t, J=10.2 Hz), 3.69 (1H, dd, J=9.4, 9.2 Hz), 3.68 (3H, s), 3.58 (1H, ddd, J=9.9, 9.9, 4.9 Hz), 3.55 (1H, dd, J=9.1, 9.0 Hz), 3.20 (1H, dd, app. t, J=9.5, 8.5 Hz), 3.07 (3H, s)

¹³C-NMR (125 MHz, CDCl₃): 138.51, 137.19, 128.77, 128.23, 128.06, 127.25, 125.88, 100.99, 85.28, 84.25, 82.17, 81.86, 70.16, 68.78, 60.84, 60.58

C,H-analysis: calculated: C 70.77%, H 6.79%
found: C 73.68%, H 8.40%

Deprotection 7.32

To a solution of acetal KPE0000115 (2.8 g, 7.860 mmol) in methanol (80 ml) was added at room temperature camphorsulfonic acid (600 mg, 2.590 mmol). The mixture was stirred at room temperature for 3 hours. Triethylamine (2 ml) was added and the solvent was removed under reduced pressure. The crude product 7.32 was purified by flash chromatography (gradient elution: cyclohexane/ethyl acetate 1/0 to 4/6) to yield 1.85 g (88%) of a yellow oil 7.32.

Formula: $C_{14}H_{20}O_5$
Molecular weight: 268.31
$R_f$: 0.10 (cyclohexane/ethyl acetate 1:1)
$[\alpha]_D^{20}$=−172.1; $[\alpha]_{365}^{20}$=−190.1 (c=0.81 in chloroform)
IR(KBr): 3405, 2926, 1731, 1496, 1455, 1382, 1287, 1256, 1192, 1145, 1069, 1036, 975, 953, 884, 764, 701 cm⁻¹
ES-MS: 286=[268+NH₄]⁺

¹H-NMR (500 MHz, CDCl₃): 7.38 (3H, m), 7.35 (2H, m), 4.18 (1H, d, J=9.4 Hz), 3.92 (1H, dd, J=11.8, 8.4 Hz), 3.80 (1H, dd, J=11.8, 6.7 Hz), 3.68 (1H, s), 3.60 (1H, dd, app. t, J=9.3 Hz), 3.48 (1H, ddd, J=9.5, 6.0, 4.4 Hz), 3.28 (1H, dd, app. t, J=9.0 Hz), 3.11 (1H, dd, app. t, J=9.2 Hz), 2.94 (3H, s)

¹³C-NMR (125 MHz, CDCl₃): 138.63, 128.18, 127.27, 87.48, 85.80, 81.45, 78.90, 70.55, 62.69, 60.89, 59.74

C,H-analysis: calculated: C 62.67%, H 7.51%
found: C 63.06%, H 8.78%

EXAMPLE 48

Synthesis of KPE00001019 and KPE00001020

Bromide 7.36

To a solution of 2,3,4,6-tetra-O-benzyl-D-glucopyranose 7.35 (4.0 g, 7.4 mmol) in dry methylene chloride (50 ml) and dimethylformamide (2.5 ml) was added at room temperature a solution of oxalylbromide (1 ml, 10 mmol) in dry methylene chloride (1 ml). The mixture was stirred at room temperature for 1 hour and then poured into icewater (50 ml). The two layers were separated and the organic layer was washed with cold water (2×50 ml), dried (MgSO$_4$) and filtered. The solvent was removed under reduced pressure to a orange colored oil. The crude product 7.36 was used in the next step.

Formula: $C_{34}H_{35}BrO_5$
Molecular weight: 603.55
$R_f$: 0.53 (cyclohexane/ethyl acetate 85:15)
$^1$H-NMR (500 MHz, CDCl$_3$): 7.37 (3H, m), 7.33 (5H, m), 7.31 (5H, m), 7.28 (5H, m), 7.15 (2H, m), 6.43 (1H, d, J=3.7 Hz), 4.98 (1H, d, J=5.0 Hz), 4.83 (2H, dd, app. t, J=10.9 Hz), 4.58 (1H, d, J=12.1 Hz), 4.50 (1H, d, J=10.7 Hz), 4.46 (2H, d, J=12.1 Hz), 4.06 (1H, m), 4.03 (1H, dd, app. t, J=9.2 Hz), 3.80 (1H, m), 3.78 (1H, m), 3.76 (1H, d, J=4.6 Hz), 3.65 (1H, dd, J=11.0, 2.0 Hz), 3.54 (1H, dd, J=9.2, 3.7 Hz)

Grignard Reaction 7.37

To a solution of bromide 7.36 (4.47 g, 7.4 mmol) in dry diethylether (100 ml) was added at 0° C. benzylmagnesiumbromide (60 ml of a 1M solution in diethylether, 60 mmol). The mixture was stirred at 0° C. for 1 hour and at room temperature for 18 hours. Then the reaction mixture was poured into water (200 ml) and acetic acid (10 ml) was added. The two layers were separated and the organic layer was washed with a saturated sodium bicarbonate solution (3×250 ml) and brine (2×250 ml). The organic layer was dried (MgSO$_4$), filtered and the solvent was removed under reduced pressure. The crude product was purified by flash chromatography (gradient elution: cyclohexane/ethyl acetate 95/5 to 85/15), followed by HPLC (eluent: cyclohexane/diethylether 9/1) to yield 2.2 g (48%) of a colorless oil 7.37.

Formula: $C_{41}H_{42}O_5$
Molecular weight: 614.78
$R_f$: 0.15 (cyclohexane/diethylether 9:1)
$[\alpha]_D^{20}$=+85.3; $[\alpha]_{365}^{20}$=+88.1(c=0.60 in chloroform)
IR(KBr): 2862, 2360, 1604, 1496, 1454, 1360, 1209, 1085, 1028, 735, 697, 668 cm$^{-1}$
ES-MS: 632=[614+NH$_4$]$^+$
$^1$H-NMR (500 MHz, CDCl$_3$): 7.36 (5H, m), 7.34 (5H, m), 7.31 (5H, m), 7.29 (5H, m), 7.26 (2H, m), 7.22 (3H, m), 4.96 (1H, d, J=11.0 Hz), 4.95 (1H, d, J=11.0 Hz), 4.91 (1H, d, J=11.0 Hz), 4.84 (1H, d, J=10.8 Hz), 4.69 (1H, d, J=11.0 Hz), 4.62 (1H, d, J=10.8 Hz), 4.59 (1H, d, J=12.2 Hz), 4.52 (1H, d, J=12.2 Hz), 3.74 (1H, dd, app. t, J=9.0 Hz), 3.69 (1H, m), 3.68 (1H, m), 3.66 (1H, dd, app. t, J=9.3 Hz), 3.52 (1H, ddd, J=18.3, 9.2, 2.3 Hz), 3.37 (1H, dd, app. t, J=9.0 Hz), 3.36 (1H, m), 3.17 (1H, dd, J=14.3, 2.0 Hz), 2.75 (1H, dd, J=14.3, 8.8 Hz)
$^{13}$C-NMR (125 MHz, CDCl$_3$): 138.68, 138.41, 138.22, 138.04, 138.01, 129.49, 128.35, 128.31, 128.26, 128.15, 127.91, 127.77, 127.69, 127.56, 127.50, 127.33, 125.95, 87.26, 81.59, 79.86, 78.80, 78.47, 75.41, 74.99, 74.81, 73.22, 68.77, 37.72
C,H-analysis: calculated: C 80.10%, H 6.90%
found: C 79.38%, H 7.09%

Deprotection 7.38

To a solution of 7.37 (2.0 g, 3.25 mmol) in ethanol (80 ml) was added at room temperature palladium on carbon (Pd-C, 200 mg). The mixture was shaken (Parr apparatus) at room temperature for 2 hours under a hydrogen pressure of 4 atm. The suspension was filtered over celite, the filter was washed with ethanol and tetrahydrofuran, and the solvent was removed under reduced pressure. The crude product was purified by flash chromatography (eluent: methylene chloride/methanol 9/1) to yield 1.15 g (99%) of product 7.38.

Formula: $C_{13}H_{18}O_5$
Molecular weight: 254.28
$R_f$: 0.14 (dichloormethane/methanol 9:1)
IR(KBr): 3381, 2922, 2360, 2341, 1641, 1603, 1496, 1454, 1379, 1308, 1226, 1079, 1031, 897, 754, 701, 668 cm$^{-1}$
ES-MS: 272=[254+NH$_4$]$^+$
$^1$H-NMR (500 MHz, CDCl$_3$): 7.29 (2H, d, J=7.0 Hz), 7.22 (2H, dd, app. t, J=7.3 Hz), 7.14 (1H, m), 3.75 (1H, dd, J=11.9, 2.4 Hz), 3.60 (1H, dd, J=11.8, 5.4 Hz), 3.35 (1H, m), 3.32 (1H, m), 3.25 (1H, dd, app. t, J=9.4 Hz), 3.15 (1H, m), 3.12 (1H, m), 3.09 (1H, dd, app. t, J=9.3 Hz), 2.69 (1H, dd, J=14.5, 8.5 Hz)
$^{13}$C-NMR (125 MHz, CDCl$_3$): 140.50, 130.71, 128.96, 126.97, 81.73, 81.40, 79.91, 74.91, 71.90, 62.98, 38.73
C,H-analysis: calculated: C 61.40%, H 7.10%
found: C 58.92%, H 7.15%

Benzylidene acetal KPE00001053

To a solution of tetrol 7.38 (1.0 g, 3.93 mmol) in dimethylformamide (40 ml) were added at room temperature camphorsulfonic acid (274 mg, 1.18 mmol) and benzaldehyde dimethyl acetal (0.652 ml, 4.72 mmol). The mixture was stirred at 110° C. for 6 hours. It was then diluted with ethyl acetate (100 ml), washed with a 1M sodiumhydroxide solution (2×150 ml), a saturated sodium bicarbonate solution (2×150 ml) and brine (2×150 ml). The organic layer was dried (MgSO$_4$), filtered and the solvent was removed under reduced pressure. The crude product was purified by flash chromatography (gradient elution: cyclohexane/ethyl acetate 9/1 to 6/4) to yield 950 mg (71%) of a white solid KPE00001053.

Formula: $C_{20}H_{22}O_5$
Molecular weight: 342.39
$R_f$: 0.20 (cyclohexane/ethyl acetate 6:4)
Melting point: 43-44° C.
$[\alpha]_D^{20}$=-6.9; $[\alpha]_{365}^{20}$=-10.7 (c=0.60 in chloroform)
IR(KBr): 3478, 3031, 2871, 2360, 1604, 1497, 1454, 1385, 1317, 1299, 1271, 1212, 1124, 1099, 1077, 998, 973, 919, 673, 699, 668, 655, 625, 552, 510 cm$^{-1}$
ES-MS: 343=[342+H]$^+$
$^1$H-NMR (500 MHz, CDCl$_3$): 7.49 (2H, m), 7.38 (3H, m), 7.31 (2H, m), 7.28 (2H, m), 7.25 (1H, m), 5.51 (1H, s), 4.28 (1H, dd, J=10.5, 4.8 Hz), 3.74 (1H, dd, app. t, J=8.7 Hz), 3.68 (1H, dd, app. t, J=10.0 Hz), 3.58 (1H, ddd, J=9.6, 8.2, 2.6 Hz), 3.43 (1H, dd, app. t, J=9.2 Hz), 3.39 (1H, m), 3.38 (1H, dd, J=10.5, 4.0 Hz), 3.18 (1H, dd, J=14.4, 2.5 Hz), 2.93 (1H, bs), 2.79 (1H, dd, J=14.4, 7.9 Hz), 2.69 (1H, bs)
$^{13}$C-NMR (125 MHz, CDCl$_3$): 137.84, 136.93, 129.63, 129.20, 128.26, 128.02, 126.20, 126.15, 101.69, 80.90, 80.14, 75.24, 73.58, 69.94, 68.71, 37.71

C,H-analysis: calculated: C 70.20%, H 6.50%
found: C 68.84%, H 6.59%

Dimethylether KPE00001019

To a solution of diol KPE00001053 (920 mg, 2.69 mmol) in dry dimethyl ethylene glycol (30 ml) was added at 0° C. sodiumhydride (650 mg, 16.12 mmol). The mixture was stirred at 0° C. for 30 minutes. Iodomethane (0.67 ml, 10.75 mmol) was added at 0° C. and the reaction mixture was stirred at room temperature for 16 hours. It was then poured into water (50 ml) and the two layers were separated. The water layer was extracted with ethyl acetate (3×50 ml). The combined organic layers were dried (MgSO$_4$), filtered and the solvent was removed under reduced pressure. The crude product was purified by flash chromatography (gradient elution: cyclohexane/ethyl acetate 95/5 to 7/3) to yield 907 mg (91%) of a white solid KPE00001019.

Formula: $C_{22}H_{26}O_5$
Molecular weight: 370.44
$R_f$: 0.63 (cyclohexane/ethyl acetate 6:4)
Melting point: 103-104° C.
IR(KBr): 3027, 2982, 2891, 2831, 1603, 1496, 1455, 1380, 1323, 1277, 1232, 1167, 1141, 1121, 1094, 1030, 989, 958, 875, 754, 698, 654, 622, 580, 543, 502 cm$^{-1}$
ES-MS: 371=[370+H]$^+$
$^1$H-NMR (500 MHz, CDCl$_3$): 7.49 (2H, m), 7.35 (3H, m), 7.29 (2H, m), 7.25 (3H, m), 5.53 (1H, s), 4.25 (1H, dd, J=10.5, 5.0 Hz), 3.67 (1H, dd, J=10.3, 5.0 Hz), 3.66 (3H, s), 3.63 (3H, s), 3.51 (1H, m), 3.49 (1H, dd, app. t, J=8.8 Hz), 3.47 (1H, m), 3.30 (1H, ddd, J=14.4, 9.5, 5.0 Hz), 3.14 (1H, dd, J=14.4, 2.1 Hz), 2.98 (1H, dd, app. t, J=8.8 Hz), 2.73 (1H, dd, J=14.3, 8.4 Hz)
$^{13}$C-NMR (125 MHz, CDCl$_3$): 138.20, 137.32, 129.51, 128.74, 128.06, 127.98, 126.10, 125.89, 100.92, 84.92, 82.83, 82.10, 80.23, 69.88, 68.77, 60.77, 60.59, 37.97
C,H-analysis: calculated: C 71.30%, H 7.10%
found: C 71.26%, H 7.45%

Deprotection KPE00001020

To a suspension of acetal KPE00001019 (860 mg, 2.32 mmol) in methanol (25 ml) was added at room temperature camphorsulfonic acid (180 mg, 0.774 mmol). The mixture was stirred at room temperature for 2 hours. Triethylamine (0.2 ml) was added and the solvent was removed under reduced pressure. The crude product was purified by flash chromatography (gradient elution: cyclohexane/ethyl acetate 9/1 to 7/3) to yield 655 mg (99%) of a white solid KPE00001020.

Formula: $C_{15}H_{22}O_5$
Molecular weight: 282.34
$R_f$: 0.11 (cyclohexane/ethyl acetate 1:1)
IR(KBr): 3320, 2921, 2358, 1682, 1651, 1556, 1454, 1372, 1177, 1136, 1090, 1027, 957, 934, 833, 752, 696, 624, 525 cm$^{-1}$
ES-MS: 300=[282+NH$_4$]$^+$ $^1$H-NMR (500 MHz, CDCl$_3$): 7.28 (2H, m), 7.24 (3H, m), 3.78 (1H, m), 3.67 (3H, s), 3.65 (1H, ddd, J=11.3, 5.8 Hz), 3.60 (3H, s), 3.44 (1H, ddd, J=9.5, 9.4, 2.3 Hz), 3.41 (1H, ddd, J=9.5, 9.4, 2.3 Hz), 3.19 (1H, ddd, J=13.0, 9.2, 3.5 Hz), 3.18 (1H, dd, app. t, J=9.0 Hz), 3.13 (1H, dd, J=14.5, 2.3 Hz), 2.91 (1H, dd, app. t, J=9.1 Hz), 2.71 (1H, m), 2.68 (1H, dd, J=14.2, 9.2 Hz), 1.98 (1H, m)
$^{13}$C-NMR (125 MHz, CDCl$_3$): 138.28, 129.26, 128.04, 126.13, 88.24, 83.66, 79.58, 78.34, 70.86, 62.70, 60.84, 60.37, 37.71
C,H-analysis: calculated: C 63.80%, H 7.90%
found: C 64.59%, H 7.78%

Although the invention has been described with respect to a preferred embodiment thereof, it is to be also understood that it is not to be so limited since changes and modifications can be made therein which are within the full intended scope of this invention as defined by the appended claims.

We claim:
1. A compound of the formula:

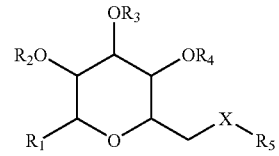

wherein
R$_1$ is —H, -Ph, -PhS, —All, or -Bn;
R$_2$ is, —H, -Me, or -Bn;
R$_3$ is, —H, -Me, or -Bn; and
R$_4$ and R$_5$ are each —OH.
2. A compound as defined in claim 1, wherein R$_1$ is —SPh and R$_2$ and R$_3$ are each -Me.
3. A compound as defined in claim 1, wherein R$_1$ is -Bn and R$_2$ and R$_3$ are each -Me.
4. A compound of the formula:

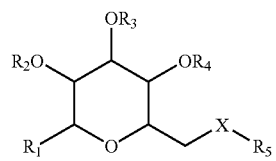

wherein, R1 is selected from of —H, —SPh, and -Bn;
R2 and R3 are selected from the group consisting of -Me and -Bn;
R4 is selected from the group consisting of —H, and alkyl;
X is selected from the group consisting of O, N$_3$ and NH; and
R5 is alkyl.

* * * * *